(12) United States Patent
Ghilardi et al.

(10) Patent No.: US 7,303,896 B2
(45) Date of Patent: Dec. 4, 2007

(54) NUCLEIC ACID ENCODING NOVEL TYPE-1 CYTOKINE RECEPTOR GLM-R

(75) Inventors: Nico P. Ghilardi, Millbrae, CA (US); Frederic J. de Sauvage, Foster City, CA (US); Audrey Goddard, San Francisco, CA (US); Paul J. Godowski, Hillsborough, CA (US); J. Christopher Grimaldi, San Francisco, CA (US); Austin Gurney, Belmont, CA (US); William I. Wood, Hillsborough, CA (US)

(73) Assignee: Genentech, Inc., So. San Francisco, CA (US)

( * ) Notice: Subject to any disclaimer, the term of this patent is extended or adjusted under 35 U.S.C. 154(b) by 0 days.

(21) Appl. No.: 10/373,512

(22) Filed: Feb. 24, 2003

(65) Prior Publication Data

US 2007/0174922 A1 Jul. 26, 2007

Related U.S. Application Data

(60) Provisional application No. 60/359,806, filed on Feb. 25, 2002.

(51) Int. Cl.
*C12P 21/06* (2006.01)

(52) U.S. Cl. ............... 435/69.1; 435/320.1; 435/252.3; 435/325; 435/6; 536/23.5; 530/350

(58) Field of Classification Search ............... 435/69.1, 435/320.1, 252.3, 325, 6; 536/23.5; 530/350
See application file for complete search history.

(56) References Cited

U.S. PATENT DOCUMENTS 5,776,731 A * 7/1998 Parnet et al. ............... 435/69.1
2003/0096339 A1 * 5/2003 Sprecher et al. ........... 435/69.1

FOREIGN PATENT DOCUMENTS

WO 02/00721 A2 1/2002

OTHER PUBLICATIONS

Reznikov et al. IL—18 binding protein increase spontaneous and IL—1-induced prostaglandin production via inhibition of IFN-gamma. Proc. Natl. Acad. Sci., 2000, 97(5): 2174-79.*
Gordon et al, "Monocyte and Macrophage Heterogeneity" *Nature Reviews —Immunology* 5:953-964 (Dec. 2005).
Ghilardi Nico et al, "A novel type I Cytokine receptor is expressed on monocytes, signals proliferation, and activates STAT-3 and STAT-5" *J Biol Chem.* 277(19) :16831-16836 (May 10, 2002).
Bazan, J. Fernando, "Haemopoietic Receptors and Helical Cytokines" *Immunology Today* 11 (10) :350-354 (1990).
Bazan, J. Fernando, "Structural Design and Molecular Evolution of a Cytokine Receptor Superfamily" *Proc. Natl. Acad. Sci. USA* 87:6934-6938 (Sep. 1990).
Bunting et al., "Reduced Lymphomyeloid Repopulating Activity from Adult Bone Marrow and Fetal Liver of Mice Lacking Expression of STATS" *Blood* 99(2) :479-487 (Jan. 2002).
Darnell, James E., "STATs and Gene Regulation" *Science* 277:1630-1635 (Sep. 1997).
de Sauvage et al. , "Stimulation of Megakaryocytopoiesis and Thrombopoiesis by the c-Mpl Ligand"*Nature* 369:533-538 (Jun. 16, 1994).
de Vos et al., "Human Growth Hormone and Extracellular Domain of its Receptor: Crystal Structure of the Complex" *Science* 255:306-312 (1992).
Feldman et al. , "STAT5A-Deficient Mice Demonstrate a Defect in Granulocyte-Macrophage Colony-Stimulating Factor-Induced Proliferation and Gene Expression" *Blood* 90 (5) :1768-1776 (Sep. 1997).
Greenberger et al. , "Demonstration of Permanent Factor-Dependent Multipotential (Erthroid/Neutrophil/Basophil) Hematopoietic Progenitor Cell Lines" *Proc. Natl. Acad. Sci. USA* 80 (10) :2931-2935 (May 1983).
Hibi et al. , "Molecular Cloning and Expression of an IL-6 Signal Transducer, gp130"*Cell* 63 (6) :1149-1157 (Dec. 1990).
Ho et al., "Site-Directed Mutagensis by Overlap Extension Using the Polymerase Chain Reaction" *Gene* 77 (1) :51-59 (1989).
Ihle et al., "Jaks and Stats in Cytokine Signaling" *Stem Cell* (Suppl. 1, Discussion p. 112) 15:105-112 (1997).
Ihle, James N., "Cytokine Receptor Signalling" *Nature* 377:591-594 (Oct. 1995).
Ihle, James N. , "STATs: Signal Transducers and Activators of Transcription" *Cell* 84:331-334 (Feb. 1996).
Ihel, James N. , "The Stat Family in Cytokine Signaling" *Current Opin. Cell. Biol.* 13(2) :212-217 (2001).
Itoh et al., "Cloning of an Interleukin-3 Receptor Gene: A Member of a Distinct Receptor Gene Family"*Science* 247:324-327 (1990).
Kawashima et al. , "STATS Induces Macrophage Differentiation of M1 Leukemia Cells Through Activation of IL-6 Production Mediated by NP-KB p65[1]" *J. Immunol.* 167(7) :3652-3660 (2001).
Kuhn et al., "Interleukin-10-Deficient Mice Develop Chronic Enterocolitis" *Cell* 75(2) :263-274 (Oct. 1993).
Larsen et al., "Expression Cloning of a Human Granulocyte Colony-Stimulating Factor Receptor: A Structural Mosaic of Hematopoietin Receptor, Immunoglobulin, and Fibronectin Domains" *Journal of Experimental Medicine* 172(6) :1559-1570 (Dec. 1990).

(Continued)

*Primary Examiner*—Gary B. Nickol
*Assistant Examiner*—Dong Jiang
(74) *Attorney, Agent, or Firm*—Craig G. Svoboda

(57) ABSTRACT

The present invention is directed to novel polypeptides and variants thereof of GLM-R polypeptides and to nucleic acid molecules encoding those polypeptides. Also provided herein are vectors and host cells comprising those nucleic acid sequences, chimeric polypeptide molecules comprising the polypeptides of the present invention fused to heterologous polypeptide sequences, antibodies which bind to the polypeptides of the present invention and to methods for producing the polypeptides of the present invention. Also provided are methods for detecting agents that modulate the activity of GLM-R. Also provided are methods for diagnosing and for treating disorders characterized by the over or under abundance of monocytes or macrophages.

15 Claims, 7 Drawing Sheets

OTHER PUBLICATIONS

Levy et al., "Cytoplasmic Activation of ISGP3, the Positive Regulator of Interferon-α -Stimulated Transcription, Reconstituted In Vitro" *Genes & Development* 3:1362-1371 (1989).

Lok et al., "Cloning and Expression of Murine Thrombopoietin cDNA and Stimulation of Platelet Production in vivo" *Nature* 369:565-568 (Jun. 16, 1994).

Mu et al., "Megakaryocyte Growth and Development Factor and Interleukin-3 Induce Patterns of Protein-Tyrosine Phosphorylation That Correlate with Dominant Differentiation Over Proliferation of mpl-Transfected 32D Cells" *Blood* 86 (12) :4532-4543 (Dec. 1995).

Nosaka et al., "STATS as a Molecular Regulator of Proliferation, Differentiation and Apoptosis in Hematopoietic Cells" *EMBO Journal* 18 (17) :4754-4765 (1999).

O'Farrell et al., "IL-10 Inhibits Macrophage Activation and Proliferation by Distinct Signaling Mechanisms: Evidence for STAT3-Dependent and -Independent Pathways" *EMBO Journal* 17 (4) : 1006-1018 (1998).

Pallard et al., "Interleukin-3, Erythropoietin, and Prolactin Activate a STATS-Like Factor in Lymphoid Cells" *Journal of Biological Chemistry* 270 (27) :15942-5 (Jul. 1995).

Parrish-Novak et al., "Interleukin 21 and its Receptor are Involved in NK Cell Expansion and Regulation of Lymphocyte Function" *Nature* 408:57-63 (Nov. 2000).

Presky et al., "A Functional Interleukin 12 Receptor Complex is Composed of Two β-Type Cytokine Receptor Subunits" *Proc. Natl. Acad. Sci. USA* 93 (24) :14002-14007 (Nov. 1996).

Reich et al., "Interferon-Induced Transcription of a Gene Encoding a 15-kDa Protein Depends on an Upstream Enhancer Element" *Proc. Natl. Acad. Sci. USA* 85 (18) :6394-8 (Sep. 1987).

Riley et al., "Interleukin-10 Receptor Signaling Through the JAK-STAT Pathway" *Journal of Biological Chemistry* 274 (23) :16513-16521 (Jun. 1999).

Rozwarski et al., "Structural Comparisons Among the Short-Chain Helical Cytokines" *Structure* 2:159-173 (Mar. 1994).

Schmitt-Ney et al., "β-Casein Gene Promoter Activity Is Regulated by the Hormone-Mediated Relief of Tanscriptional Repression and a Mammary-Gland-Specific Nuclear Factor" *Molecular & Cellular Biology* 11 (7) :3745-3755 (Jul. 1991).

Takeda et al., "Enhanced Thi Activity and Development of Chronic Enterocolitis in Mice Devoid of Stat3 in Macrophages and Neutrophils" *Immunity* 10 (1):39-49 (Jan. 1999).

Wagner et al., "The SIP Binding Element Confers sis/PDGF Inducibility onto the c-fos Promoter" *EMBO Journal* 9 (13) :4477-4484 (1990).

* cited by examiner

CATGTGTCTGTGAATGTCCGCAAAACATTCTCTCTCCCCAGCCTTCATGTGTTAACCTGG
GGATGATGTGGACCTGGGCACTGTGGATGCTCCCTTCACTCTGCAAATTCAGCCTGGCAG
CTCTGCCAGCTAAGCCTGAGAACATTTCCTGTGTCTACTACTATAGGAAAAATTTAACCT
GCACTTGGAGTCCAGGAAAGGAAACCAGTTATACCCAGTACACAGTTAAGAGAACTTACG
CTTTTGGAGAAAAACATGATAATTGTACAACCAATAGTTCTACAAGTGAAAATCGTGCTT
CGTGCTCTTTTTTCCTTCCAAGAATAACGATCCCAGATAATTATACCATTGAGGTGGAAG
CTGAAAATGGAGATGGTGTAATTAAATCTCATATGACATACTGGAGATTAGAGAACATAG
CGAAAACTGAACCACCTAAGATTTTCCGTGTGAAACCAGTTTTGGGCATCAAACGAATGA
TTCAAATTGAATGGATAAAGCCTGAGTTGGCGCCTGTTTCATCTGATTTAAAATACACAC
TTCGATTCAGGACAGTCAACAGTACCAGCTGGATGGAAGTCAACTTCGCTAAGAACCGTA
AGGATAAAAACCAAACGTACAACCTCACGGGGCTGCAGCCTTTTACAGAATATGTCATAG
CTCTGCGATGTGCGGTCAAGGAGTCAAAGTTCTGGAGTGACTGGAGCCAAGAAAAAATGG
GAATGACTGAGGAAGAAGCTCCATGTGGCCTGGAACTGTGGAGAGTCCTGAAACCAGCTG
AGGCGGATGGAAGAAGGCCAGTGCGGTTGTTATGGAAGAAGGCAAGAGGAGCCCCAGTCC
TAGAGAAAACACTTGGCTACAACATATGGTACTATCCAGAAAGCAACACTAACCTCACAG
AAACAATGAACACTACTAACCAGCAGCTTGAACTGCATCTGGGAGGCGAGAGCTTTTGGG
TGTCTATGATTTCTTATAATTCTCTTGGGAAGTCTCCAGTGGCCACCCTGAGGATTCCAG
CTATTCAAGAAAATCATTTCAGTGCATTGAGGTCATGCAGGCCTGCGTTGCTGAGGACC
AGCTAGTGGTGAAGTGGCAAAGCTCTGCTCTAGACGTGAACACTTGGATGATTGAATGGT
TTCCGGATGTGGACTCAGAGCCCACCACCCTTTCCTGGGAATCTGTGTCTCAGGCCACGA
ACTGGACGATCCAGCAAGATAAATTAAAACCTTTCTGGTGCTATAACATCTCTGTGTATC
CAATGTTGCATGACAAAGTTGGCGAGCCATATTCCATCCAGGCTTATGCCAAAGAAGGCG
TTCCATCAGAAGGTCCTGAGACCAAGGTGGAGAACATTGGCGTGAAGACGGTCACGATCA
CATGGAAAGAGATTCCCAAGAGTGAGAGAAAGGGGATCATCTGCAACTACACCATCTTTT
ACCAAGCTGAAGGTGGAAAAGGATTCTCCAAGACAGTCAATTCCAGCATCTTGCAGTACG
GCCTGGAGTCCCTGAAACGAAAGACCTCTTACATTGTTCAGGTCATGGCCAGCACCAGTG
CTGGGGAACCAACGGGACCAGCATAAATTTCAAGACATTGTCATTCAGTGTCTTTGAGA
TTATCCTCATAACTTCTCTGATTGGTGGAGGCCTTCTTATTCTCATTATCCTGACAGTGG
CATATGGTCTCAAAAAACCCAACAAATTGACTCATCTGTGTTGGCCCACCGTTCCCAACC
CTGCTGAAAGTAGTATAGCCACATGGCATGGAGATGATTTCAAGGATAAGCTAAACCTGA
AGGAGTCTGATGACTCTGTGAACACAGAAGACAGGATCTTAAAACCATGTTCCACCCCCA
GTGACAAGTTGGTGATTGACAAGTTGGTGGTGAACTTTGGGAATGTTCTGCAAGAAATTT
TCACAGATGAAGCCAGAACGGGTCAGGAAAACAATTTAGGAGGGGAAAAGAATGGGTATG
TGACCTGCCCCTTCAGGCCTGATTGTCCCCTGGGGAAAAGTTTTGAGGAGCTCCCAGTTT
CACCTGAGATTCCGCCCAGAAAATCCCAATACCTACGTTCGAGGATGCCAGAGGGGACCC
GCCCAGAAGCCAAAGAGCAGCTTCTCTTTTCTGGTCAAAGTTTAGTACCAGATCATCTGT
GTGAGGAAGGAGCCCCAAATCCATATTTGAAAAATTCAGTGACAGCCAGGGAATTTCTTG
TGTCTGAAAAACTTCCAGAGCACACCAAGGGAGAAGTCTAAATGCGACCATAGCATGAGA
CCCTCGGGGCCTCAGTGTGGATGGCCCTTGCCAGAGAAGATGTCAAGACTCGGCATGCAG
CGCTTGCTTGGCCCTGCCACATCCTGCCTAGGTTAAAGTTTCCCCTGCCCCTTGAGCTGC
CAGTTGAACTTGGTCGGCAAAGATGCGACCTTGTACTGGGAAGAAGGGATGGTGATAAGC
CCGAGTTTTGTAAAGGAAAAA

MMWTWALWMLPSLCKFSLAALPAKPENISCVYYYRKNLTCTWSPGKETSYTQYTVKRTYA
FGEKHDNCTTNSSTSENRASCSFFLPRITIPDNYTIEVEAENGDGVIKSHMTYWRLENIA
KTEPPKIFRVKPVLGIKRMIQIEWIKPELAPVSSDLKYTLRFRTVNSTSWMEVNFAKNRK
DKNQTYNLTGLQPFTEYVIALRCAVKESKFWSDWSQEKMGMTEEEAPCGLELWRVLKPAE
ADGRRPVRLLWKKARGAPVLEKTLGYNIWYYPESNTNLTETMNTTNQQLELHLGGESFWV
SMISYNSLGKSPVATLRIPAIQEKSFQCIEVMQACVAEDQLVVKWQSSALDVNTWMIEWF
PDVDSEPTTLSWESVSQATNWTIQQDKLKPFWCYNISVYPMLHDKVGEPYSIQAYAKEGV
PSEGPETKVENIGVKTVTITWKEIPKSERKGIICNYTIFYQAEGGKGFSKTVNSSILQYG
LESLKRKTSYIVQVMASTSAGGTNGTSINFKTLSFSVFEIILITSLIGGGLLILIILTVA
YGLKKPNKLTHLCWPTVPNPAESSIATWHGDDFKDKLNLKESDDSVNTEDRILKPCSTPS
DKLVIDKLVVNFGNVLQEIFTDEARTGQENNLGGEKNGYVTCPFRPDCPLGKSFEELPVS
PEIPPRKSQYLRSRMPEGTRPEAKEQLLFSGQSLVPDHLCEEGAPNPYLKNSVTAREFLV
SEKLPEHTKGEV

Important features of the protein:
Signal peptide:

1-19

Transmembrane domain:

515-539

N-glycosylation site.

27-31
  37-41
  67-71
  71-75
  93-97
  166-170
  183-187
  187-191
  277-281
  283-287

FIG. 2B 380-384
395-399
455-459
473-477
504-508 cAMP- and cGMP-dependent protein kinase phosphorylation site.
485-489
486-490

N-myristoylation site.
105-111
451-457
501-507
502-508
505-511
627-633
633-639

Amidation site
242-246

Growth factor and cytokines receptors family signature 1
30-43

Growth factor and cytokines receptors family proteins
211-219

Fibronectin type III domain
122-215

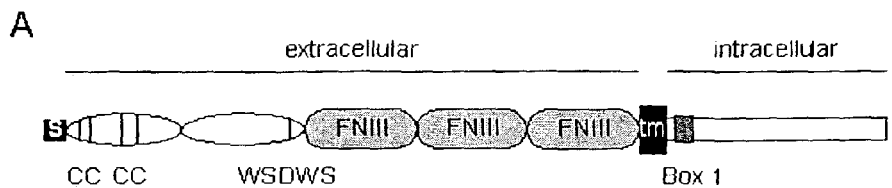

A extracellular | intracellular

CC CC    WSDWS    FNIII FNIII FNIII    Box 1

B

```
hu   1 MMWTWALWMLPSLCKFSLAALPAKPENISCVYYYRKNLTCTWSPGKETSY
mo   1 MWTLALWAFSFLCKFSLAVLPTKPENISCVFYFDRNLTCTWRPEKETND hu  51 TQYTVKRTYAFGEKHDNCTTNSSTSENRASCSFFLPRITIPDNYTIEVEA
mo  50 TSYIVTLTYSYGK------SNYSDNATEASYSFPRSCAMPPDICSVEVQA hu 101 ENGDGVIKSHMTYWRLENIAKTEPPKIFRVKPVLGIKRMIQIEWIKPELA
mo  94 QNGDGKVKSDITYWHLISIAKTEPPIILSVNPIC--NRMFQIQWK-PREK hu 151 PVSSDLKYTLRFRTVNSTSWMEVNFAKNRKDKNQTYNLTGLQPFTEYVIA
mo 141 TRGFPLVCMLRFRTVNSSRWTEVNFENCK----QVCNLTGLQAFTEYVLA hu 201 LRCAVKESKFWSDWSQEKMGMTEEEAPCGLELWRVLKPAEADGRRPVRLL
mo 187 LRFRFNDSRYWSKWSKEETRVTMEEVPHVLDLWRILEPADMNGDRKVRLL hu 251 WKKARGAPVLEKTLGYNIWYYPESNTNLTETMNTTNQQLELHLGGESFWV
mo 237 WKKARGAPVLEKTFGYHIQYFAENWTNLTEINNITTQQYELLLMSQAHSV hu 301 SMISYNSLGKSPVATLRIPAIQEKSFQCIEVMQACVAEDQLVVKWQSSAL
mo 287 SVTSFNSLGKSQETILRIPDVHEKTFQYIKSMQAYIWEPLLVVNWQSSIP hu 351 DVNTWMIEWFPDVD-SEPTTLSWESVSQATNWTIQQDKLKPFWCYNISVY
mo 337 AVDTWIVEWLPEAAMSKFPADWSWESVSQVTNWTIEQDKLKPFTCYNISVY hu 400 PMLHDKVGEPYSIQAYAKEGVPSEGPETKVENIGVKTVTITWKEIPKSER
mo 387 PVLGHRVGEPYSIQAYAKEGTPLKGPETRVENIGLRTATITWKEIPKSAR hu 450 KGIICNYTIFYQAEGGKGFSKTVNSSIIQWGLESLKRKTSYIVQVMASTS
mo 437 NGFINNYTVFYQAEGGKELSKTVNSHALQCDLESLTRRTSYTVWVMASTR hu 500 AGGTNGKSINFKTLSFSVFEIILIWSLIGGGLLILIILTVAYGLKKPNKL
mo 487 AGGTNGVRINFKTISISVFEIVLLTSLVGGGLLLLSIKTVTFGLRKPNRL hu 550 THLCWPTVPNPAESSIATWHGDDFKDKLNLKESDDSVNTEDRILKPCSTP
mo 537 TPLCCPDVPNPAESSLATWLGDGFK-KSNMKETGNSGNTEDVVLKPCVP hu 600 SDKLVIDKLVVNFGNVLQEIFTDEARTGQENNLGGEKNGYVTCPFRPDCP
mo 586 AD--LIDKLVVNFENFLEVVLTEEAGKGQASILGGEANEYVTSPSRPDGP hu 650 LGKSFEELPVSPEIPPRKSQYLRSRMPEGTRPEAKEQLLFSGQSLVPDHL
mo 634 PGKSFKEPSILTEVASEDSHSTCSRMADEAYSELARQPSSSCQSPGLSPP hu 700 CEEGAPNPYLKNSVTAREFLVSEKLPEHTKGEV
mo 684 REDQAQNPYLKNSVTTREFLVHENIPEHSKGEV
```

C

| receptor | % identity | human chr. | mouse chr. |
|---|---|---|---|
| GLM-R | 100.00 | 5q11.2 | 13 |
| gp13 | 24.73 | 5q11 | 13 |
| βCSF-R | 23.94 | 1p35-p34.3 | 4 |
| IL12-Rβ2 | 20.09 | 1p31.3-p31.2 | 6 |

*FIG. 3*

SEQUENCE LISTING

<160> NUMBER OF SEQ ID NOS: 15

<210> SEQ ID NO 1
<211> LENGTH: 2481
<212> TYPE: DNA
<213> ORGANISM: Homo sapien

<400> SEQUENCE: 1

| | | | | | |
|---|---|---|---|---|---|
| catgtgtctg | tgaatgtccg | caaaacattc | tctctcccca | gccttcatgt | 50 |
| gttaacctgg | ggatgatgtg | gacctgggca | ctgtggatgc | tcccttcact | 100 |
| ctgcaaattc | agcctggcag | ctctgccagc | taagcctgag | aacatttcct | 150 |
| gtgtctacta | ctataggaaa | aatttaacct | gcacttggag | tccaggaaag | 200 |
| gaaaccagtt | atacccagta | cacagttaag | agaacttacg | cttttggaga | 250 |
| aaaacatgat | aattgtacaa | ccaatagttc | tacaagtgaa | aatcgtgctt | 300 |
| cgtgctcttt | tttccttcca | agaataacga | tcccagataa | ttataccatt | 350 |
| gaggtggaag | ctgaaaatgg | agatggtgta | attaaatctc | atatgacata | 400 |
| ctggagatta | gagaacatag | cgaaaactga | accacctaag | attttccgtg | 450 |
| tgaaaccagt | tttgggcatc | aaacgaatga | ttcaaattga | atggataaag | 500 |
| cctgagttgg | cgcctgtttc | atctgattta | aaatacacac | ttcgattcag | 550 |
| gacagtcaac | agtaccagct | ggatggaagt | caacttcgct | aagaaccgta | 600 |
| aggataaaaa | ccaaacgtac | aacctcacgg | ggctgcagcc | ttttacagaa | 650 |
| tatgtcatag | ctctgcgatg | tgcggtcaag | gagtcaaagt | tctggagtga | 700 |
| ctggagccaa | gaaaaaatgg | gaatgactga | ggaagaagct | ccatgtggcc | 750 |
| tggaactgtg | gagagtcctg | aaaccagctg | aggcggatgg | aagaaggcca | 800 |
| gtgcggttgt | tatggaagaa | ggcaagagga | gccccagtcc | tagagaaaac | 850 |
| acttggctac | aacatatggt | actatccaga | aagcaacact | aacctcacag | 900 |
| aaacaatgaa | cactactaac | cagcagcttg | aactgcatct | gggaggcgag | 950 |
| agcttttggg | tgtctatgat | ttcttataat | tctcttggga | agtctccagt | 1000 |
| ggccaccctg | aggattccag | ctattcaaga | aaaatcattt | cagtgcattg | 1050 |
| aggtcatgca | ggcctgcgtt | gctgaggacc | agctagtggt | gaagtggcaa | 1100 |
| agctctgctc | tagacgtgaa | cacttggatg | attgaatggt | ttccggatgt | 1150 |
| ggactcagag | cccaccaccc | tttcctggga | atctgtgtct | caggccacga | 1200 |
| actggacgat | ccagcaagat | aaattaaaac | ctttctggtg | ctataacatc | 1250 |
| tctgtgtatc | caatgttgca | tgacaaagtt | ggcgagccat | attccatcca | 1300 |
| ggcttatgcc | aaagaaggcg | ttccatcaga | aggtcctgag | accaaggtgg | 1350 |
| agaacattgg | cgtgaagacg | gtcacgatca | catggaaaga | gattcccaag | 1400 |
| agtgagagaa | aggggatcat | ctgcaactac | accatctttt | accaagctga | 1450 |
| aggtggaaaa | ggattctcca | agacagtcaa | ttccagcatc | ttgcagtacg | 1500 |
| gcctggagtc | cctgaaacga | aagacctctt | acattgttca | ggtcatggcc | 1550 |
| agcaccagtg | ctgggggaac | caacgggacc | agcataaatt | tcaagacatt | 1600 |
| gtcattcagt | gtctttgaga | ttatcctcat | aacttctctg | attggtggag | 1650 |
| gccttcttat | tctcattatc | ctgacagtgg | catatggtct | caaaaaaccc | 1700 |

-continued

```
aacaaattga ctcatctgtg ttggcccacc gttcccaacc ctgctgaaag      1750
tagtatagcc acatggcatg gagatgattt caaggataag ctaaacctga      1800
aggagtctga tgactctgtg aacacagaag acaggatctt aaaaccatgt      1850
tccaccccca gtgacaagtt ggtgattgac aagttggtgg tgaactttgg      1900
gaatgttctg caagaaattt tcacagatga agccagaacg ggtcaggaaa      1950
acaatttagg aggggaaaag aatgggtatg tgacctgccc cttcaggcct      2000
gattgtcccc tggggaaaag ttttgaggag ctcccagttt cacctgagat      2050
tccgcccaga aaatcccaat acctacgttc gaggatgcca gaggggaccc      2100
gcccagaagc caaagagcag cttctctttt ctggtcaaag tttagtacca      2150
gatcatctgt gtgaggaagg agccccaaat ccatatttga aaaattcagt      2200
gacagccagg gaatttcttg tgtctgaaaa acttccagag cacaccaagg      2250
gagaagtcta aatgcgacca tagcatgaga ccctcggggc ctcagtgtgg      2300
atggcccttg ccagagaaga tgtcaagact cggcatgcag cgcttgcttg      2350
gccctgccac atcctgccta ggttaaagtt tcccctgccc cttgagctgc      2400
cagttgaact tggtcggcaa agatgcgacc ttgtactggg aagaagggat      2450
ggtgataagc ccgagttttg taaaggaaaa a                          2481
```

<210> SEQ ID NO 2
<211> LENGTH: 732
<212> TYPE: PRT
<213> ORGANISM: Homo sapien

<400> SEQUENCE: 2

```
Met Met Trp Thr Trp Ala Leu Trp Met Leu Pro Ser Leu Cys Lys
  1               5                  10                  15

Phe Ser Leu Ala Ala Leu Pro Ala Lys Pro Glu Asn Ile Ser Cys
                 20                  25                  30

Val Tyr Tyr Tyr Arg Lys Asn Leu Thr Cys Thr Trp Ser Pro Gly
                 35                  40                  45

Lys Glu Thr Ser Tyr Thr Gln Tyr Thr Val Lys Arg Thr Tyr Ala
                 50                  55                  60

Phe Gly Glu Lys His Asp Asn Cys Thr Thr Asn Ser Ser Thr Ser
                 65                  70                  75

Glu Asn Arg Ala Ser Cys Ser Phe Phe Leu Pro Arg Ile Thr Ile
                 80                  85                  90

Pro Asp Asn Tyr Thr Ile Glu Val Glu Ala Glu Asn Gly Asp Gly
                 95                 100                 105

Val Ile Lys Ser His Met Thr Tyr Trp Arg Leu Glu Asn Ile Ala
                110                 115                 120

Lys Thr Glu Pro Pro Lys Ile Phe Arg Val Lys Pro Val Leu Gly
                125                 130                 135

Ile Lys Arg Met Ile Gln Ile Glu Trp Ile Lys Pro Glu Leu Ala
                140                 145                 150

Pro Val Ser Ser Asp Leu Lys Tyr Thr Leu Arg Phe Arg Thr Val
                155                 160                 165

Asn Ser Thr Ser Trp Met Glu Val Asn Phe Ala Lys Asn Arg Lys
                170                 175                 180

Asp Lys Asn Gln Thr Tyr Asn Leu Thr Gly Leu Gln Pro Phe Thr
                185                 190                 195
```

```
Glu Tyr Val Ile Ala Leu Arg Cys Ala Val Lys Glu Ser Lys Phe
            200                 205                 210

Trp Ser Asp Trp Ser Gln Glu Lys Met Gly Met Thr Glu Glu Glu
            215                 220                 225

Ala Pro Cys Gly Leu Glu Leu Trp Arg Val Leu Lys Pro Ala Glu
            230                 235                 240

Ala Asp Gly Arg Arg Pro Val Arg Leu Leu Trp Lys Lys Ala Arg
            245                 250                 255

Gly Ala Pro Val Leu Glu Lys Thr Leu Gly Tyr Asn Ile Trp Tyr
            260                 265                 270

Tyr Pro Glu Ser Asn Thr Asn Leu Thr Glu Thr Met Asn Thr Thr
            275                 280                 285

Asn Gln Gln Leu Glu Leu His Leu Gly Gly Glu Ser Phe Trp Val
            290                 295                 300

Ser Met Ile Ser Tyr Asn Ser Leu Gly Lys Ser Pro Val Ala Thr
            305                 310                 315

Leu Arg Ile Pro Ala Ile Gln Glu Lys Ser Phe Gln Cys Ile Glu
            320                 325                 330

Val Met Gln Ala Cys Val Ala Glu Asp Gln Leu Val Val Lys Trp
            335                 340                 345

Gln Ser Ser Ala Leu Asp Val Asn Thr Trp Met Ile Glu Trp Phe
            350                 355                 360

Pro Asp Val Asp Ser Glu Pro Thr Thr Leu Ser Trp Glu Ser Val
            365                 370                 375

Ser Gln Ala Thr Asn Trp Thr Ile Gln Gln Asp Lys Leu Lys Pro
            380                 385                 390

Phe Trp Cys Tyr Asn Ile Ser Val Tyr Pro Met Leu His Asp Lys
            395                 400                 405

Val Gly Glu Pro Tyr Ser Ile Gln Ala Tyr Ala Lys Glu Gly Val
            410                 415                 420

Pro Ser Glu Gly Pro Glu Thr Lys Val Glu Asn Ile Gly Val Lys
            425                 430                 435

Thr Val Thr Ile Thr Trp Lys Glu Ile Pro Lys Ser Glu Arg Lys
            440                 445                 450

Gly Ile Ile Cys Asn Tyr Thr Ile Phe Tyr Gln Ala Glu Gly Gly
            455                 460                 465

Lys Gly Phe Ser Lys Thr Val Asn Ser Ser Ile Leu Gln Tyr Gly
            470                 475                 480

Leu Glu Ser Leu Lys Arg Lys Thr Ser Tyr Ile Val Gln Val Met
            485                 490                 495

Ala Ser Thr Ser Ala Gly Gly Thr Asn Gly Thr Ser Ile Asn Phe
            500                 505                 510

Lys Thr Leu Ser Phe Ser Val Phe Glu Ile Ile Leu Ile Thr Ser
            515                 520                 525

Leu Ile Gly Gly Gly Leu Leu Ile Leu Ile Ile Leu Thr Val Ala
            530                 535                 540

Tyr Gly Leu Lys Lys Pro Asn Lys Leu Thr His Leu Cys Trp Pro
            545                 550                 555

Thr Val Pro Asn Pro Ala Glu Ser Ser Ile Ala Thr Trp His Gly
            560                 565                 570

Asp Asp Phe Lys Asp Lys Leu Asn Leu Lys Glu Ser Asp Asp Ser
            575                 580                 585
```

-continued

```
Val Asn Thr Glu Asp Arg Ile Leu Lys Pro Cys Ser Thr Pro Ser
            590                 595                 600

Asp Lys Leu Val Ile Asp Lys Leu Val Val Asn Phe Gly Asn Val
            605                 610                 615

Leu Gln Glu Ile Phe Thr Asp Glu Ala Arg Thr Gly Gln Glu Asn
            620                 625                 630

Asn Leu Gly Gly Glu Lys Asn Gly Tyr Val Thr Cys Pro Phe Arg
            635                 640                 645

Pro Asp Cys Pro Leu Gly Lys Ser Phe Glu Glu Leu Pro Val Ser
            650                 655                 660

Pro Glu Ile Pro Pro Arg Lys Ser Gln Tyr Leu Arg Ser Arg Met
            665                 670                 675

Pro Glu Gly Thr Arg Pro Glu Ala Lys Glu Gln Leu Leu Phe Ser
            680                 685                 690

Gly Gln Ser Leu Val Pro Asp His Leu Cys Glu Glu Gly Ala Pro
            695                 700                 705

Asn Pro Tyr Leu Lys Asn Ser Val Thr Ala Arg Glu Phe Leu Val
            710                 715                 720

Ser Glu Lys Leu Pro Glu His Thr Lys Gly Glu Val
            725                 730

<210> SEQ ID NO 3
<211> LENGTH: 30
<212> TYPE: DNA
<213> ORGANISM: Artificial sequence
<220> FEATURE:
<221> NAME/KEY: Artificial Sequence
<222> LOCATION: Full
<223> OTHER INFORMATION: Forward PCR Primer

<400> SEQUENCE: 3
gtcaaggagt caaagttctg gagtgactgg                                     30

<210> SEQ ID NO 4
<211> LENGTH: 27
<212> TYPE: DNA
<213> ORGANISM: Artificial sequence
<220> FEATURE:
<221> NAME/KEY: Artificial Sequence
<222> LOCATION: Full
<223> OTHER INFORMATION: Reverse PCR Primer

<400> SEQUENCE: 4
cgcacatcgc agagctatga catattc                                        27

<210> SEQ ID NO 5
<211> LENGTH: 33
<212> TYPE: DNA
<213> ORGANISM: Artificial sequence
<220> FEATURE:
<221> NAME/KEY: Artificial Sequence
<222> LOCATION: Full
<223> OTHER INFORMATION: Hybridization probe

<400> SEQUENCE: 5
cgtacaacct cacggggctg cagcctttta cag                                 33

<210> SEQ ID NO 6
<211> LENGTH: 39
<212> TYPE: DNA
<213> ORGANISM: Artificial sequence
<220> FEATURE:
<221> NAME/KEY: Artificial Sequence
```

```
<222> LOCATION: Full
<223> OTHER INFORMATION: PCR Primer (sense)

<400> SEQUENCE: 6
cttttcgaaa cagcaaagga aacccaacaa attgactca                    39

<210> SEQ ID NO 7
<211> LENGTH: 33
<212> TYPE: DNA
<213> ORGANISM: Artificial sequence
<220> FEATURE:
<221> NAME/KEY: Artificial Sequence
<222> LOCATION: Full
<223> OTHER INFORMATION: PCR Primer (antisense)

<400> SEQUENCE: 7
gggtttcctt tgctgtttcg aaaagagaaa aac                          33

<210> SEQ ID NO 8
<211> LENGTH: 20
<212> TYPE: DNA
<213> ORGANISM: Artificial sequence
<220> FEATURE:
<221> NAME/KEY: Artificial Sequence
<222> LOCATION: Full
<223> OTHER INFORMATION: PCR Primer (sense)

<400> SEQUENCE: 8
cctggagtcc ctgaaacgaa                                         20

<210> SEQ ID NO 9
<211> LENGTH: 19
<212> TYPE: DNA
<213> ORGANISM: Artificial sequence
<220> FEATURE:
<221> NAME/KEY: Artificial Sequence
<222> LOCATION: Full
<223> OTHER INFORMATION: PCR Primer (antisense)

<400> SEQUENCE: 9
gttggttccc ccagcactg                                          19

<210> SEQ ID NO 10
<211> LENGTH: 29
<212> TYPE: DNA
<213> ORGANISM: Artificial sequence
<220> FEATURE:
<221> NAME/KEY: Artificial Sequence
<222> LOCATION: Full
<223> OTHER INFORMATION: PCR Primer (probe)

<400> SEQUENCE: 10
ctcttacatt gttcaggtca tggccagca                               29

<210> SEQ ID NO 11
<211> LENGTH: 20
<212> TYPE: DNA
<213> ORGANISM: Artificial sequence
<220> FEATURE:
<221> NAME/KEY: Artificial Sequence
<222> LOCATION: Full
<223> OTHER INFORMATION: PCR Primer (sense)

<400> SEQUENCE: 11
gatgccggaa aaacaccttg                                         20

<210> SEQ ID NO 12
```

-continued

```
<211> LENGTH: 19
<212> TYPE: DNA
<213> ORGANISM: Artificial sequence
<220> FEATURE:
<221> NAME/KEY: Artificial Sequence
<222> LOCATION: Full
<223> OTHER INFORMATION: PCR Primer (antisense)

<400> SEQUENCE: 12
tggctgtacc cttccgctt                                              19

<210> SEQ ID NO 13
<211> LENGTH: 23
<212> TYPE: DNA
<213> ORGANISM: Artificial sequence
<220> FEATURE:
<221> NAME/KEY: Artificial Sequence
<222> LOCATION: Full
<223> OTHER INFORMATION: PCR Primer (probe)

<400> SEQUENCE: 13
cctatgccca tgtgcctgcc ctt                                         23

<210> SEQ ID NO 14
<211> LENGTH: 17
<212> TYPE: DNA
<213> ORGANISM: Artificial sequence
<220> FEATURE:
<221> NAME/KEY: Artificial Sequence
<222> LOCATION: Full
<223> OTHER INFORMATION: PCR Primer

<400> SEQUENCE: 14
catttcccgt aaatcat                                                17

<210> SEQ ID NO 15
<211> LENGTH: 20
<212> TYPE: DNA
<213> ORGANISM: Artificial sequence
<220> FEATURE:
<221> NAME/KEY: Artificial Sequence
<222> LOCATION: Full
<223> OTHER INFORMATION: PCR Primer

<400> SEQUENCE: 15
gatttctagg aattcaatcc                                             20
```

NUCLEIC ACID ENCODING NOVEL TYPE-1 CYTOKINE RECEPTOR GLM-R

This is a non-provisional application claiming priority to provisional application No. 60/359,806 filed Feb. 25, 2002, the entire disclosure of which is hereby incorporated by reference.

FIELD OF THE INVENTION

The present invention relates to GLM-R genes, including the human GLM-R gene, which are novel genes involved in the development and function of monocytes and macrophages. The scope of the invention includes the identification and isolation of novel DNA encoding and to the recombinant production of novel polypeptides designated herein as GLM-R polypeptides, and to methods, compositions and assays utilizing such polypeptides in the diagnosis and treatment of disorder characterized by the over or under abundance of monocytes or macrophages. The invention encompasses nucleotide sequences of the GLM-R nucleic acid, host cell expression systems and hosts which have been transformed by these expression systems, including transgenic animals. Further included are GLM-R proteins, polypeptides and peptides containing GLM-R amino acid sequences, fusion proteins of GLM-R proteins, polypeptides and peptides, and antibodies specifically binding thereto.

BACKGROUND OF THE INVENTION

Helical cytokines control multiple biological processes, ranging from host defense to development and body homeostasis. This family of ligands, consisting of Interleukin (IL-x) 2, 3, 4, 5, 6, 7, 9, 11, 12, 13, 15, 21, 23, thymic stromal lymphopoietin (TSLP), granulocyte factor (GM-CSF), granulocyte-macrophage colony stimulating factor (GM-CSF), erythropoietin (EPO), thrombopoietin (TPO), prolactin (PRL), growth hormone (GN), leukemia inhibitory factor (LIF), oncostatin-M (OSM), cardiotrophin-1 (CT-1), cardiotrophin-like cytokine (CLC), ciliary neurotrophic factor (CNTF), and leptin (OB), has a rich source of molecules with highly specific biological effects and important therapeutic potential.

The helical cytokine family is defined by a common three-dimensional structure consisting of an anti-parallel four helix bundle with a characteristic "up-up-down-down" topology. Bazan, J. F., *Immunol. Today* 11(10): 350-4 (1990), Rozwarski, D. A. et al., *Structure* 2(3): 159-73 (1994). Unfortunately, the lack of significant sequence homology has hampered the identification of novel members of this family by homology screens, and more recently, data mining. The cognate receptors, however, form a family of so-called type I cytokine receptors and share several structural motifs, including a cytokine receptor homology (CRH) domain with 2 pairs of conserved cysteine residues and a WSXWS sequence motif in the extracellular domain [Bazan, J. F., *Proc. Natl. Acad. Sci. USA* 87(18): 6934-8 (1990)], a single transmembrane domain and an intracellular domain without intrinsic enzymatic activity. These features allow for homology-based identification of novel receptors, which in turn can be used as tools to subsequently identify their ligands by a variety of different screening techniques. De Sauvage et al., *Nature* 369(6481): 533-8 (1994); Parrish-Novak J., et al., *Nature* 408(6808): 57-63 (2000); Lok, S. et al., *Nature* 369 (6481): 565-8 (1994).

Ligand binding induces homo- or heteromerization of at least two receptor subunits. In the former case, two identical receptor subunits form a homodimeric receptor that is sufficient for ligand binding and signaling [e.g., GH-R, de Vos, A. M. et al., *Science* 255(5042): 306-12 (1992)]. Heteromerization is induced when a ligand-specific α-chain forms a high affinity receptor in combination with a signal transducing β-chain. This β-chain is shared amongst several other α-chains, e.g., IL-3, IL-5, GM-CSF. Itoh, N. et al., *Science* 247 (4940): 324-7 (1990). In either instance, ligand binding to the receptor leads to activation of cytoplasmic tyrosine kinases of the Janus kinase (Jak) family, which associate with the receptor subunits through conserved box-1 and box-2 motifs within the membrane proximal part of the intracellular domain. Ihle, J. N., *Nature* 377(6550): 591-4 (1995). Jak activation leads to phosphorylation of cytoplasmic target proteins, in particular the intracellular domains of the receptors and members of the STAT protein family, which are recruited to phosphotyrosines on the receptor by means of their src-homology type 2 (SH2) domains. Ihle, J. H. *Cell* 84(3): 331-4 (1996); Ihle, J. H. et al., *Stem Cells* 15 (Suppl. 1): 105-11, discussion 112 (1997). Phosphorylation of STATs induces dimerization and translocation to the nucleus and results in specific activation of gene transcription. Darnell, J. E., Jr., *Science* 277 (5332): 1630-5 (1997). Seven STAT proteins are known to date (STATs 1, 2, 3, 4, 5a, 5b and 6). Analysis of animals deficient for STAT isoforms indicates that STATs mediate many of the specific effects of cytokines, Ihle J. N. *Curr. Opin. Cell Biol.* 13(2): 211-7 (2001), highlighting their key importance in cytokine receptor signaling. In addition to specific target gene regulation, and in combination with other signaling pathways activated by cytokine receptors, such as mitogen-activated protein kinase and phosphatidylinositol-3 kinase, STATs can contribute to anti-apoptotic and mitogenic signals upon activation Ihle, J. N. *Nature* 377(6550): 591-4 (1995).

SUMMARY OF THE INVENTION

The present invention relates to the identification of nucleic acid that encode novel GLM-R polypeptides that are involved in the development and function of monocytes and macropahge, and physiological conditions associated therewith. The nucleic acid molecules represent nucleotide sequences corresponding to the mammalian GLM-R polynucleotides, including human GLM-R polynucleotides. Particular examples of the nucleic acids molecules of the present invention are designated herein as DNA173920-2924.

In one embodiment, the invention provides an isolated nucleic acid molecule comprising a nucleotide sequence that encodes a GLM-R polypeptide. An example GLM-R polypeptide is PRO21073.

In one aspect, the isolated nucleic acid molecule comprises a nucleotide sequence having at least about 80% nucleic acid sequence identity, alternatively at least about 81%, 82%, 83%, 84%, 85%, 86%, 87%, 88%, 89%, 90%, 91%, 92%, 93%, 94%, 95%, 96%, 97%, 98% or 99% nucleic acid sequence identity to (a) a DNA molecule encoding a polypeptide having the sequence of amino acid residues from about: 1 or about 20 to about 732, inclusive, of FIG. 2 (SEQ ID NO:2), or (b) the complement of the DNA molecule of (a).

In another aspect, the isolated nucleic acid molecule comprises (a) a nucleotide sequence encoding a GLM-R polypeptide having the sequence of amino acid residues from about: (i) 1 or about 20 to about 732, inclusive, of FIG. 2 (SEQ ID NO:2), or (b) the complement of the DNA molecule of (a).

In yet another aspect, the isolated nucleic acid molecule comprises a nucleotide sequence having at least about 80% nucleic acid sequence identity, alternatively at least about 81%, 82%, 83%, 84%, 85%, 86%, 8%, 88%, 89%, 90%, 91%, 92%, 93%, 94%, 95%, 96%, 97%, 98% or 99% nucleic acid sequence identity to (a) a DNA molecule having the sequence of nucleotides from about 63 or about 120 to about 2258, inclusive, of FIG. 1 (SEQ ID NO:1), or (b) the complement of the DNA molecule of (a).

In yet another aspect, the isolated nucleic acid molecule comprises (a) the nucleotide sequence from about 63 or about 120 to about 2258, inclusive, of FIG. 1 (SEQ ID NO:1), or (b) the complement of the DNA molecule of (a).

In yet another aspect, the isolated nucleic acid molecule comprises a nucleotide sequence having at least about 80% nucleic acid sequence identity, alternatively at least about 81%, 82%, 83%, 84%, 85%, 86%, 87%, 88%, 89%, 90%, 91%, 92%, 93%, 94%, 95%, 96%, 97%, 98% or 99% nucleic acid sequence identity to: (a) a DNA molecule that encodes the same mature polypeptide encoded by the human protein cDNA deposited with the ATCC on May 16, 2000 under ATCC Dep. No. 1874-PTA (DNA173920-2924) or (b) the complement of the nucleotide sequence of (a).

In yet another aspect, the isolated nucleic acid molecule comprises a nucleotide sequence having at least about 80% nucleic acid sequence identity, alternatively at least about 81%, 82%, 83%, 84%, 85%, 86%, 87%, 88%, 89%, 90%, 91%, 92%, 93%, 94%, 95%, 96%, 97%, 98% or 99% nucleic acid sequence identity to: (a) the full-length polypeptide coding sequence of the DNA deposited with the ATCC on May 16, 2000 under ATCC Dep. No. 1874-PTA (DNA173920-2924) or (b) the complement of the nucleotide sequence of (a). In a specific aspect, the isolated nucleic acid molecule comprises: (a) the full-length polypeptide coding sequence of the DNA deposited with the ATCC on May 16, 2000 under ATCC Deposit No. 1874-PTA (DNA173920-2924), or (b) the complement of the nucleotide sequence of (a).

In yet another aspect, the isolated nucleic acid molecule is a nucleotide sequence which encodes an active GLM-R polypeptide as defined below comprising a nucleotide sequence that hybridizes to the complement of (a) a nucleic acid sequence that encodes amino acid residues from about 1 or about 20 to about 732, inclusive, of FIG. 2 (SEQ ID NO:2). Preferably, hybridization occurs under stringent hybridization and wash conditions.

In yet another aspect, the isolated nucleic acid molecule is a nucleotide sequence which encodes an active GLM-R polypeptide as defined below comprising a nucleotide sequence that hybridizes to the complement of (a) the nucleic acid sequence between about nucleotides 63 or about 120 and about 2258, inclusive, of FIG. 1 (SEQ ID NO:1). Preferably, hybridization occurs under stringent hybridization and wash conditions.

In yet another aspect, the isolated nucleic acid is a nucleotide sequence having at least about 702 nucleotide residues and which is produced by hybridizing a test DNA molecule under stringent conditions with (a) a DNA molecule encoding a GLM-R polypeptide having the sequence of amino acid residues from about 1 or about 20 to about 732, inclusive, of FIG. 2A (SEQ ID NO:2), or (b) the complement of the DNA molecule of (a), and, if the test DNA molecule has at least about an 80% nucleic acid sequence identity, alternatively at least about 81%, 82%, 83%, 84%, 85%, 86%, 87%, 88%, 89%, 90%, 91%, 92%, 93%, 94%, 95%, 96%, 97%, 98% or 99% nucleic acid sequence identity to (a) or (b), and isolating the test DNA molecule.

In yet another aspect, the isolated nucleic acid molecule comprises DNA encoding a GLM-R polypeptide without the N-terminal signal sequence and/or the initiating methionine, or is complementary to such encoding nucleic acid molecule. The signal peptide has been tentatively identified as extending from about amino acid position 1 to about amino acid position 19, inclusive, in the sequence of FIG. 2 (SEQ ID NO:2). It is noted, however, that the C-terminal boundary of the signal peptide may vary, but most likely by no more than about 5 amino acids on either side of the signal peptide C-terminal boundary as initially identified herein, wherein the C-terminal boundary of the signal peptide may be identified pursuant to criteria routinely employed in the art for identifying that type of amino acid sequence element (e.g., Nielsen et al., *Prot. Eng.* 10:1-6 (1997) and von Heinje et al., *Nucl. Acids. Res.* 14:4683-4690 (1986)). Moreover, it is also recognized that, in some cases, cleavage of a signal sequence from a secreted polypeptide is not entirely uniform, resulting in more than one secreted species. These polypeptides, and the polynucleotides encoding them, are contemplated by the present invention. As such, for purposes of the present application, the signal peptide of the GLM-R polypeptide shown in FIG. 2 (SEQ ID NO:2) extends from amino acids 1 to X of FIG. 2 (SEQ ID NO:2), respectively, wherein X is any amino acid from 15 to 24 of FIG. 2 (SEQ ID NO:2), respectively. Therefore, mature forms of the GLM-R polypeptide which are encompassed by the present invention include those comprising amino acid residues X to 732 of FIG. 2 (SEQ ID NO:2); wherein X is any amino acid from 15 to 24 of FIG. 2 (SEQ ID NO:2) and variants thereof as described below. Isolated nucleic acid molecules encoding these polypeptides are also contemplated.

In yet another embodiment, the invention provides an isolated nucleic acid molecule comprising a nucleotides sequence encoding a GLM-R polypeptide which is either transmembrane domain-deleted or transmembrane domain-inactivated, or is complementary to such encoding nucleotide sequence, wherein the transmembrane domain has been tentatively identified as extending from about amino acid position 515 to about amino acid position 539 in the sequence of FIG. 2 (SEQ ID NO:2). Therefore, soluble extracellular domains of the herein described GLM-R polypeptides are contemplated.

In yet another embodiment, the invention provided an isolated nucleic acid molecule comprising a nucleotide sequence having at least about 80% nucleic acid sequence identity, alternatively at least about 81%, 82%, 83%, 84%, 85%, 86%, 87%, 88%, 89%, 90%, 91%, 92%, 93%, 94%, 95%, 96%, 97%, 98%, 99% nucleic acid sequence identity to (a) a DNA molecule encoding amino acids 1 to X of FIG. 2 (SEQ ID NO:2), where X is any amino acid from 510 to 519 of FIG. 2 (SEQ ID NO:2), or (b) the complement of the DNA molecule of (a). In a specific aspect, the isolated nucleic acid molecule comprises a nucleotide sequence which encodes amino acids 1 to X of FIG. 2 (SEQ ID NO:2), where X is any amino acid from 510 to 519 of FIG. 2 (SEQ ID NO:2), or (b) is the complement of the DNA molecule of (a).

In yet another embodiment, the invention provides fragments of a GLM-R polypeptide sequence which includes the coding sequence that may find use as, for example, hybridization probes or for encoding fragments of a GLM-R polypeptide that may optionally encode a polypeptide comprising a binding site for an anti-GLM-R antibody. Such nucleic acid fragments are usually at least about 20, 30, 40, 50, 60, 70, 80, 90, 100, 110, 120, 130, 140, 150, 160, 170, 180, 190, 200, 250, 300, 350, 400, 450, 500, 600, 700, 800, 900, 1000 nucleotides in length, wherein in this context the term "about" means the referenced nucleotide sequence length plus or minus up to 10% of that referenced length. In a preferred embodiment, the nucleotide sequence fragment is derived from any coding region of the nucleotide sequence shown in FIG. 1 (SEQ ID NO:1). It is noted that novel fragments of a GLM-R polypeptide-encoding nucleotide sequence may be determined in a routine manner by aligning the GLM-R polypeptide-encoding nucleotide sequence with other known nucleotide sequences using any of a number of well known sequence alignment programs and determining which GLM-R polypeptide-encoding nucleotide sequence fragment(s) are novel. All of such GLM-R polypeptide-encoding nucleotide sequences are contemplated herein and can be determined without undue experimentation. Also contemplated are the GLM-R polypeptide fragments encoded by these nucleotide molecule fragments, preferably those GLM-R polypeptide fragments that comprise a binding site for an anti-GLM-R antibody.

In yet another embodiment, the invention provides a vector (e.g., expression vectors) comprising a nucleotide sequence encoding GLM-R or its variants. The vector may comprise any of the isolated nucleic acid molecules hereinabove identified. A host cell comprising such a vector is also provided. By way of example, the host cells may be CHO cells, E. coli, baculovirus infected insect cells, or yeast. In one aspect, the invention comprises host organisms that have been transformed with GLM-R-encoding nucleotide sequence, including, for example, transgenic animals.

In another aspect, the transgenic animals of the invention express a GLM-R variant, in particular a variant that is associated with a weight disorder such as obesity, cachexia or anorexia. In particular, such transgenic animals comprise those that express a GLM-R transgene at higher or lower levels than normal. In another particular aspect, the transgenic animals include those which express GLM-R in all or some ("mosaic") of their cells. In yet a further particular aspect, such transgenic animals further includes those in which GLM-R nucleic acid is introduced into and expressed in only specific cell types. In yet another particular aspect, the invention includes "knock-out" animals, or animals which have been modified to no longer express, or express in a lower quantity, GLM-R polynucleotides.

In yet another embodiment, the invention provides isolated GLM-R polypeptide encoded by any of the isolated nucleic acid sequences hereinabove identified. In one aspect, the invention provides isolated native sequence GLM-R polypeptide, which in certain embodiments, includes an amino acid sequence comprising residues from about 1 or about 20 to about 732, inclusive, of FIG. 2 (SEQ ID NO:2).

In yet another aspect, the invention provides an isolated GLM-R polypeptide, comprising an amino acid sequence having at least about 80% amino acid sequence identity, alternatively at least about 81%, 82%, 83%, 84%, 85%, 86%, 87%, 88%, 89%, 90%, 91%, 92%, 93%, 94%, 95%, 96%, 97%, 98% or 99% amino acid sequence identity to the sequence of amino acid residues from about 1 or about 20 to about 732, inclusive, of FIG. 2 (SEQ ID NO:2).

In yet another aspect, the invention provides an isolated GLM-R polypeptide comprising an amino acid sequence having at least about 80% amino acid sequence identity, alternatively at least about 81%, 82%, 83%, 84%, 85%, 86%, 87%, 88%, 89%, 90%, 91%, 92%, 93%, 94%, 95%, 96%, 97%, 98% or 99% amino acid sequence identity to an amino acid sequence encoded by the human protein cDNA deposited with the ATCC on May 16, 2000, under ATCC Deposit No. 1874-PTA (DNA173920-2924). In a particular embodiment, the isolated GLM-R polypeptide comprises an amino acid sequence encoding by the human protein cDNA deposited with the ATCC on May 16, 2000 under ATCC Deposit No. 1874-PTA (DNA173920-2924).

In yet another aspect, the isolated GLM-R polypeptide comprises a polypeptide without the N-terminal signal sequence and/or the initiating methionine and is encoded by a nucleotide sequence that encodes such an amino acid sequence as hereinbefore described. Processes for producing the same are also herein described, wherein those processes comprise culturing a host cell comprising a vector which comprises the appropriate encoding nucleic acid molecule under conditions suitable for expression of the GLM-R polypeptide and recovering the GLM-R polypeptide from the cell culture.

In yet another aspect, the invention provides an isolated GLM-R polypeptide that is either transmembrane domain-deleted or transmembrane domain-inactivated. Processes for producing the same are also herein described, wherein those processes comprise culturing a host cell comprising a vector comprising the appropriate encoding nucleic acid molecule under conditions suitable for expression of the GLM-R polypeptide and recovering the GLM-R polypeptide from the cell culture.

In a specific aspect, the invention provides an isolated soluble GLM-R polypeptide comprising an amino acid sequence having at least about 80% amino acid sequence identity, alternatively at least about 81%, 82%, 83%, 84%, 85%, 86%, 87%, 88%, 89%, 90%, 91%, 92%, 93%, 94%, 95%, 96%, 97%, 98%, 99% amino acid sequence identity to amino acids 1 to X of FIG. 2 (SEQ ID NO:2), where X is any amino acid from 510 to 519 of FIG. 2 (SEQ ID NO:2). In a specific aspect, the isolated soluble GLM-R polypeptide comprises amino acids 1 to X of FIG. 2 (SEQ ID NO:2), where X is any amino acid from 510 to 519 of FIG. 2 (SEQ ID NO:2).

In yet another aspect, the isolated GLM-R polypeptide is a polypeptide comprising the sequence of amino acid residues from about 1 or about 20 to about 732, inclusive, of FIG. 2 (SEQ ID NO:2), inclusive, of FIG. 2, or a fragment thereof which is biologically active or sufficient to provide a binding site for an anti-GLM-R antibody, wherein the identification of GLM-R polypeptide fragments that possess biological activity or provide a binding site for an anti-GLM-R antibody may be accomplished in a routine manner using techniques which are well known in the art. Preferably, the GLM-R fragment retains a qualitative biological activity of a native GLM-R polypeptide, including the affect the development or function of monocytes or macrophages.

In yet another aspect, the isolated GLM-R polypeptide is a polypeptide produced by (1) hybridizing a test DNA molecule under stringent conditions with (a) a DNA molecule encoding a GLM-R polypeptide having the sequence of amino acid residues from about 1 or about 20 to about 732, inclusive, of FIG. 2 (SEQ ID NO:2), (b) the complement of the DNA molecule of (a), and if the test DNA molecule has at least about an 80% sequence identity, alternatively at least about 81%, 82%, 83%, 84%, 85%, 86%, 87%, 88%, 89%, 90%, 91%, 92%, 93%, 94%, 95%, 96%, 97%, 98% or 99% nucleic acid sequence identity to (a) or (b), (2) culturing a host cell comprising the test DNA molecule under conditions suitable for expression of the polypeptide, and (3) recovering the polypeptide from the cell culture.

In yet another embodiment, the invention provides chimeric molecules comprising an GLM-R polypeptide fused to a heterologous polypeptide or amino acid sequence, wherein the GLM-R polypeptide may comprise any GLM-R polypeptide, variant or fragment thereof as hereinbefore described. An example of such a chimeric molecule comprises a GLM-R polypeptide fused to an epitope tag sequence or an Fc region of an immunoglobulin.

In another embodiment, the invention provides an antibody as defined below which specifically binds to a GLM-R polypeptide as hereinbefore described. Optionally, the antibody is a monoclonal antibody, an antibody fragment or a single chain antibody.

In yet another embodiment, the invention provides a method of identifying agonists or antagonists to a GLM-R polypeptide which comprises contacting the GLM-R polypeptide with a candidate molecule and monitoring a biological activity mediated by said GLM-R polypeptide. In a particular aspect, the GLM-R polypeptide is a native sequence GLM-R polypeptide.

In yet another embodiment, the invention provides a composition of matter comprising a GLM-R polypeptide, or an agonist or antagonist of a GLM-R polypeptide as herein described, or an anti-GLM-R antibody, in combination with a carrier. Optionally, the carrier is a pharmaceutically acceptable carrier.

In yet another embodiment, the invention provides a use of a GLM-R polypeptide, or an agonist or antagonist thereof as herein described, or an anti-GLM-R antibody, for the preparation of a medicament useful in the treatment of a condition which is responsive to the GLM-R polypeptide, an agonist or antagonist thereof or an anti-GLM-R antibody.

In yet another embodiment, the invention provides a method of screening for a bioactive agent capable of binding to GLM-R. In one aspect, the method comprises adding a candidate bioactive agent to a sample of GLM-R and determining the binding of said candidate agent to said GLM-R, wherein binding indicates a bioactive agent capable of binding to GLM-R.

In yet another embodiment, the invention provides a method of screening for a bioactive agent capable of modulating the activity of GLM-R. In one aspect, the method comprises the steps of adding a candidate bioactive agent to a sample of GLM-R and determining an alteration in the biological activity of GLM-R, wherein an alteration indicates a bioactive agent capable of modulating the activity of GLM-R. In a particular aspect, GLM-R activity is the activation of STAT-3 or STAT-5 in peripheral blood mononuclear cells (PBMC).

In yet another embodiment, the invention provides a method of identifying a receptor for GLM-R. In one aspect, the method comprises combining GLM-R with a composition comprising cell membrane material wherein said GLM-R complexes with a receptor on said cell membrane material, and identifying said receptor as a GLM-R receptor. In one aspect, the method includes a step of crosslinking said GLM-R and receptor. The cell membrane can be from an intact cell or a cell membrane extract preparation.

In yet another embodiment, a method is provided for the activation of STAT-3 or STAT-5 in cells. In one aspect, the method comprises administering GLM-R to cells in at least an amount effective to induce activation of STAT-3 or STAT-5.

In yet another embodiment, a method is provided for the regulation of the development and function of monocytes or macrophages. In one aspect, the method comprises administering GLM-R to cells in at least an amount effective to affect the development and differentiation of monocytes or macrophages.

In yet another embodiment, the invention provides cellular and non-cellular assays to identify compounds that interact with GLM-R polynucleotide and/or GLM-R polypeptide. In a particular aspect, the cell-based assays of the invention utilize cells, cell lines, or engineered cells or cell lines that express the GLM-R polypeptide.

In yet another embodiment, the invention provides a method for identifying a compound which modulates the expression of the mammalian GLM-R polynucleotide and/or its level of biological activity. In one aspect, the method comprises:

(a) contacting a compound to a cell that expresses a GLM-R polynucleotide;

(b) measuring the level of GLM-R DNA expression in the cell; and (c) comparing the level obtained in (b) to GLM-R expression level obtained in the absence of the compound;

such that if the level obtained in (b) differs from that obtained in the absence of the compound, a compound that modulates GLM-R activity is identified.

In yet another embodiment, the invention provides a method for identifying compounds which modulates the biological activity of a GLM-R polypeptide, comprising:

(a) contacting a compound to a cell that contains a GLM-R polypeptide;

(b) measuring the level of GLM-R polypeptide or activity in the cell; and (c) comparing the level obtained in (b) to the level of GLM-R polypeptide or activity obtained in the absence of the compound;

such that if the level obtained in (b) differs from that obtained in the absence of the compound, a compound that modulates a GLM-R activity is identified.

In yet another embodiment, the invention provides a method for identifying compounds which modulate the biological activity of a GLM-R polypeptide, comprising:

(a) administering a compound to a host (e.g., transgenic animal that expresses a GLM-R transgene);

(b) measuring the level of GLM-R gene transcription, GLM-R expression or activity of GLM-R activity; and (c) comparing the level obtained in (b) to the level present in the absence of the compound;

such that if the level in (b) differs from that obtained in the absence of the compound, a compound that modulates a GLM-R activity is identified.

BRIEF DESCRIPTION OF THE DRAWINGS

FIG. 1 shows the nucleotide sequence (SEQ ID NO:1) of a cDNA encoding a nucleotide sequence (nucleotides 63-2258) encoding native sequence GLM-R, wherein the nucleotide sequence (SEQ ID NO:1) is a clone designated herein as "DNA173920-2924". Also presented in bold font and underline are the positions of the respective start and stop codons.

FIG. 2 shows the amino acid sequence (SEQ ID NO:2) of a native sequence GLM-R (PRO21073) polypeptide as derived from the coding sequence of SEQ ID NO:1. Also shown are the approximate locations of various other important polypeptide domains.

FIGS. 3A-3C. FIG. 3A is a schematic to-scale representation of the domain structure of GLM-R. A block box labeled "S" represents the signal peptide. The cytokine receptor homology domain is depicted as a pair of oval shapes. The positions of four conserved cysteine residues and the WSDWS signature motif are indicated. Three repeats of a Fibronectin type III (FNIII) repeat complete the extracellular domain, and a block box labeled "tm" represents the transmembrane domain. FIG. 3B is a graphical alignment of human (SEQ ID NO:2) and murine (SEQ ID NO:16) GLM-R protein sequences. Identical amino acid residues are shaded. Predicted disulfide bridges are indicated by lines, and the WSXWS motif, transmembrane domain, and box 1 motif are boxed. The open arrowheads show the positions of introns, which were found to be conserved in both species by analysis of genomic sequences (Celara genomic databases and contig NT_016864.7, NCBI Annotation Project, National Center for Biotechnology Information, NIH, Bethesda, Md. 20894, USA). Cytoplasmic tyrosine residues are printed in boldface. FIG. 3C shows the homology and chromosomal localizations of GLM-R and related cytokine receptors. The percentage of amino acid identity was calculated by the align program.

FIG. 4A shows the tissue distribution of GLM-R transcripts in human organs. FIG. 4B shows expression of GLM-R in sorted human blood cells. FIG. 4C shows the detection of GLM-R expression by FACS on human blood cells. Freshly isolated PBMC were double stained with biotinylated antibodies and streptavidin-conjugated phycoerythrin (PE) in combination with marker antibodies coupled to FITC or CyChrome. Histograms are gated on cells positive for the indicated makers. Grey histograms, staining with biotinylated isotype antibody; white histograms, staining with biotinylated anti-GLM-R. FIG. 4D shows the expression of GLM-R in human cell lines. FIG. 4E shows the upregulation of GLM-R transcripts in monocytes from three healthy volunteers upon activation with LPS/IFNγ for 4 hours. (Note ND=not detectable).

FIG. 5A is a sequence proximal to the junction of the hGH transmembrane domain and the GLM-R intracellular domain. The amino acids predicted to be within the transmembrane region are boxed. FIG. 5B is a FACS analysis of 32D cells overexpressing the chimeric receptor. Cells were stained with a monoclonal anti-hGH-R antibody or an isotype control antibody (black), followed by an FITC-coupled goat anti-mouse antibody. FIGS. 5C and 5D depict thymidine incorporation in response to growth hormone (5C) or WEHI-3B conditioned medium (5D). A representative experiment is shown. Round symbols, parental 32D cells, squares, hGH-R/GLM-R transfected cells.

FIGS. 6A and 6B show an electrophoretic mobility shift assay using the m67(A) and βCAS (B) probes. Cells were stimulated with 10 ng/ml IL-3 or 100 ng/ml hGH, and complexes were supershifted with polyclonal antibodies as indicated. FIG. 6C shows tyrosine phosphorylation of STAT-3 and STAT-5. Phosphorylated proteins were immunoprecipitated from stimulated cell lysates with anti-phosphotyrosine antibodies and detected by western blot, using polyclonal antibodies specific for STAT-3 and STAT-5.

DETAILED DESCRIPTION OF THE PREFERRED EMBODIMENTS

I. Definitions

Figure 4:
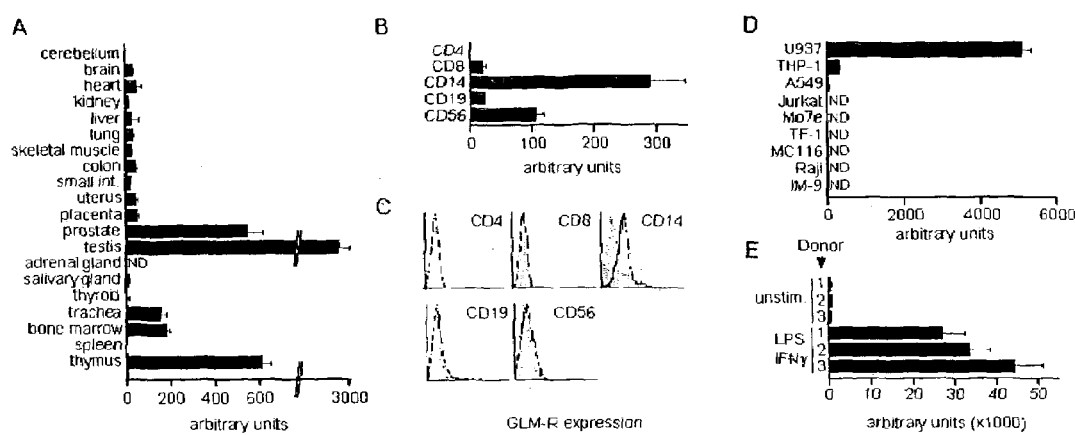
FIG. 4 is an expression pattern of GLM-R by Taqman™ and FACS. In panels A, B, D and E, GLM-R mRNA expression levels are given as arbitrary units calculated from the expression of GLM-R mRNA and expression of a housekeeping gene mRNA, rpl-19.

The terms "GLM-R polypeptide", "GLM-R protein" and "GLM-R" when used herein encompass native sequence GLM-R and GLM-R polypeptide variants (which are further defined herein). The GLM-R polypeptide may be isolated from a variety of sources, such as from human tissue types or from another source, or prepared by recombinant and/or synthetic methods. The term "GLM-R polynucleotide" includes nucleic acids which encode the polypeptides described in this paragraph.

A "native sequence GLM-R" comprises a polypeptide having the same amino acid sequence as a GLM-R derived from nature. Such native sequence GLM-R can be isolated from nature or can be produced by recombinant and/or synthetic means. The term "native sequence GLM-R" specifically encompasses naturally-occurring truncated or secreted forms (e.g., an extracellular domain sequence), naturally-occurring variant forms (e.g., alternatively spliced forms) and naturally-occurring allelic variants of the GLM-R. In one embodiment of the invention, the native sequence GLM-R is a mature or full-length native sequence GLM-R comprising amino acids 1 or about 20 to about 732, inclusive, of FIG. 2 (SEQ ID NO:2). Also, while the GLM-R polypeptides disclosed in FIG. 2 (SEQ ID NO:2) is shown to begin with the methionine residue designated herein as amino acid position 1, it is conceivable and possible that another methionine residue located either upstream or downstream from amino acid position 1 in FIG. 2 may be employed as the starting amino acid residue for the respective GLM-R polypeptide.

A GLM-R polypeptide "extracellular domain" or "ECD" refers to a form of the GLM-R polypeptide which is essentially free of the transmembrane and cytoplasmic domains. Ordinarily, a GLM-R polypeptide ECD will have less than 1% of such transmembrane and/or cytoplasmic domains and preferably, will have less than 0.5% of such domains. It will be understood that any transmembrane domains identified for the GLM-R polypeptides of the present invention are identified pursuant to criteria routinely employed in the art for identifying that type of hydrophobic domain. The exact boundaries of a transmembrane domain may vary but most likely by no more than about 5 amino acids at either end of the domain as initially identified herein. As such, in a specific aspect, the extracellular domain of a GLM-R polypeptide comprises amino acids 1 or about 20 to X, wherein X is any amino acid from amino acid 510 to 519 or FIG. 2 (SEQ ID NO:2).

The approximate location of the "signal peptides" of the various GLM-R polypeptides disclosed herein may be shown in the present specification and/or the accompanying figures. For example, for the proteins encoded by DNA173920-2924 (SEQ ID NO:1), the signal sequences are identified in FIG. 1, respectively. It is noted, however, that the C-terminal boundary of a signal peptide may vary, but most likely by no more than about 5 amino acids on either side of the signal peptide C-terminal boundary as initially identified herein, wherein the C-terminal boundary of the signal peptide may be identified pursuant to criteria routinely employed in the art for identifying that type of amino acid sequence element (e.g., Nielsen et al., *Prot. Eng.* 10: 1-6

(1997) and von Heinje et al., *Nucl. Acids. Res.* 14:4683-4690 (1986)). Moreover, it is also recognized that, in some cases, cleavage of a signal sequence from a secreted polypeptide is not entirely uniform, resulting in more than one secreted species. These mature polypeptides, where the signal peptide is cleaved within no more than about 5 amino acids on either side of the C-terminal boundary of the signal peptide as identified herein, and the polynucleotides encoding them, are contemplated by the present invention.

"GLM-R variant polypeptide" (including "GLM-R mutant" or "GLM-R polymorphism") means an active GLM-R polypeptide as defined below having at least about 80% amino acid sequence identity with the amino acid sequence of (a) 1 or about 20 to about 732, inclusive, of FIG. 2 (SEQ ID NO:2), (b) X to 732 of GLM-R polypeptide shown in FIG. 2 (SEQ ID NO:2), wherein X is any amino acid from 15 to 24 of FIG. 2 (SEQ ID NO:2), (c) 1 or about 20 to X of FIG. 2 (SEQ ID NO:2), wherein X is any amino acid from amino acid residues 510-519 of FIG. 2 (SEQ ID NO:2), or (d) another specifically derived fragment of the amino acid sequence shown in FIG. 2 (SEQ ID NO:2). Such GLM-R variant polypeptides include, for instance, GLM-R polypeptides wherein one or more amino acid residues are added, or deleted, at the N- and/or C-terminus, as well as within one or more internal domains, of the sequence of FIG. 2. Ordinarily, a GLM-R variant polypeptide will have at least about 80% amino acid sequence identity, alternatively at least about 81%, 82%, 83%, 84%, 85%, 86%, 87%, 88%, 89%, 90%, 91%, 92%, 93%, 94%, 95%, 96%, 97%, 98%, 98% or 99% amino acid sequence identity with (a) 1 or about 20 to about 732, inclusive, of the GLM-R polypeptide shown in FIG. 2 (SEQ ID NO:2), (b) X to 732 of FIG. 2 (SEQ ID NO:2), wherein X is any amino acid from 15 to 24 of FIG. 2 (SEQ ID NO:2), (c) 1 or about 20 to X of FIG. 2 (SEQ ID NO:2), wherein X is any amino acid from amino acid residues 510 to 519 of FIG. 2 (SEQ ID NO:2) or (d) another specifically derived fragment of the amino acid sequence shown in FIG. 2 (SEQ ID NO:2). GLM-R variant polypeptides explicitly do not encompass the native GLM-R polypeptide sequence. Ordinarily, GLM-R variant polypeptides are at least about 10 amino acids in length, alternatively at least about 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600 amino acids in length, or more.

"Percent (%) amino acid sequence identity" with respect to the GLM-R polypeptide sequences identified herein is defined as the percentage of amino acid residues in a candidate sequence that are identical with the amino acid residues in a GLM-R sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For purposes herein, however, % amino acid sequence identity values are obtained as described below by using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1. The ALIGN-2 program should be compiled for use on a UNIX operating system, preferably digital UNIX V4.0D. All sequence comparison parameters are set by the ALIGN-2 program and do not vary.

For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. As examples of % amino acid sequence identity calculations, Tables 2 and 3 demonstrate how to calculate the % amino acid sequence identity of the amino acid sequence designated "Comparison Protein" to the amino acid sequence designated "PRO".

Unless specifically stated otherwise, all % amino acid sequence identity values used herein are obtained as described above using the ALIGN-2 sequence comparison computer program. However, % amino acid sequence identity may also be determined using the sequence comparison program NCBI-BLAST2 [Altschul et al., Nucleic Acids Res. 25: 3389-3402 (1997]. The NCBI-BLAST2 sequence comparison program may be downloaded from the website of the National Institute of Health, Bethesda, Md. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with or against a given amino acid sequence B) is calculated as follows:

100 times the fraction X/Y where X is the number of amino acid residues scored as identical matches by the sequence alignment program NCBI-BLAST2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity B to A.

"GLM-R variant polynucleotide" or "GLM-R variant nucleic acid sequence" means a nucleic acid molecule which encodes an active GLM-R polypeptide as defined below and which has at least about 80% nucleic acid sequence identity with the nucleic acid sequence encoding amino acid residues: (a) 1 or about 20 to about 732, inclusive, of the GLM-R polypeptide of FIG. 2 (SEQ ID NO:2), (b) X to 732 of the GLM-R polypeptide of FIG. 2 (SEQ ID NO:2), wherein X is any amino acid residues from 15 to 24 of FIG. 2 (SEQ ID NO:2), (c) 1 or about 20 to X, wherein X is any amino acid residue from 510 to 519 of FIG. 2 (SEQ ID NO:2), (d) another specifically derived fragment of the amino acid sequence shown in FIG. 2 (SEQ ID NO:2). Ordinarily, a GLM-R variant polynucleotide will have at least about 80% nucleic acid sequence identity, alternatively at least about 81%, 82%, 83%, 84%, 85%, 86%, 87%, 88%, 89%, 90%, 91%, 92%, 93%, 94%, 95%, 96%, 97%, 98% or 99% nucleic acid sequence identity with: (a) a nucleic acid sequence which encodes residues 1 or about 20 to about 732, inclusive, of the GLM-R polypeptide shown in FIG. 2 (SEQ ID NO:2), (b) a nucleic acid sequence that encodes amino acids X to 732 of the GLM-R polypeptide shown in FIG. 2 (SEQ ID NO:2), wherein X is any amino acid residue from 15 to 24 of FIG. 2 (SEQ ID NO:2), (c) a nucleic acid sequence that encodes amino acids 1 or about 20 to X of FIG. 2 (SEQ ID NO:2), wherein X is any amino acid from residues 510 to 519 of FIG. 2 (SEQ ID NO:2) or (d) a nucleic acid sequence which encodes another specifically derived fragment of the amino acid sequence shown in FIG. 2 (SEQ ID NO:2). GLM-R polynucleotide variants do not encompass the native GLM-R nucleotide sequence.

Ordinarily, GLM-R variant polynucleotides are at least about 5 nucleotides in length, alternatively at least about 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides in length, wherein in this context the term "about" means the referenced nucleotide sequence length plus or minus 10% of that referenced length.

"Percent (%) nucleic acid sequence identity" with respect to the GLM-R polypeptide-encoding nucleic acid sequences identified herein is defined as the percentage of nucleotides in a candidate sequence that are identical with the nucleotides in a GLM-R polypeptide-encoding nucleic acid sequence, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For purposes herein, however, % nucleic acid sequence identity values are obtained as described below by using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 has been filed with user documentation in the U.S. Copyright Office, Washington D.C., 20559, where it is registered under U.S. Copyright Registration No. TXU50087. The ALIGN-2 program is publicly available through Genentech, Inc., South San Francisco, Calif. or may be compiled from the source code provided in Table 1. The ALIGN-2 program should be compiled for use on a UNIX operating system, preferably digital UNIX V4.0D. All sequence comparison parameters are set by the ALIGN-2 program and do not vary.

For purposes herein, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

$$100 \text{ times the fraction } W/Z$$

where W is the number of nucleotides scored as identical matches by the sequence alignment program ALIGN-2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C. As examples of % nucleic acid sequence identity calculations, Tables 4 and 5 demonstrate how to calculate the % nucleic acid sequence identity of the nucleic acid sequence designated "Comparison DNA" to the nucleic acid sequence designated "PRO-DNA". Unless specifically stated otherwise, all % nucleic acid sequence identity values used herein are obtained as described above using the ALIGN-2 sequence comparison computer program.

Unless specifically stated otherwise, all % nucleic acid sequence identity values used herein are obtained as described herein using the ALIGN-2 sequence comparison computer program. However, % nucleic acid sequence identity may also be determined using the sequence comparison program NCBI-BLAST2 [Altschul et al., *Nucleic Acids Res.* 25:3389-3402(1997)]. The NCBI-BLAST2 sequence comparison program may be downloaded from http://www.ncbi.nlm.nih.gov or otherwise obtained from the National Institute of Health, Bethesda, Md. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for sequence comparisons, the % nucleic acid sequence identity of a given nucleic acid sequence C to, with or against a given nucleic acid comprises a certain % nucleic acid sequence identity to, with or against a given nucleic acid sequence D) is calculated as follows:

$$100 \text{ times the fraction } W/Z$$

where W is the number of nucleotides scored as identical matches by the sequence alignment program NCBI-BLAST2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C.

In other embodiments, GLM-R variant polynucleotides are nucleic acid molecules that encode an active GLM-R polypeptide and which are capable of hybridizing, preferably under stringent hybridization and wash conditions, to nucleotide sequences encoding the full-length GLM-R polypeptide shown in FIG. 2 (SEQ ID NO:2). GLM-R variant polypeptides may be those that are encoded by a GLM-R variant polynucleotide.

"Isolated," when used to describe the various polypeptides disclosed herein, means polypeptide that has been identified and separated and/or recovered from a component of its natural environment. Preferably, the isolated polypeptide is free of association with all components with which it is naturally associated. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the GLM-R natural environment will not be present. Ordinarily, however, isolated polypeptide will be prepared by at least one purification step.

An "isolated" nucleic acid molecule encoding a GLM-R polypeptide is a nucleic acid molecule that is identified and separated from at least one contaminant nucleic acid molecule with which it is ordinarily associated in the natural source of the GLM-R-encoding nucleic acid. Preferably, the isolated nucleic is free of association with all components with which it is naturally associated. An isolated GLM-R-encoding nucleic acid molecule is other than in the form or setting in which it is found in nature. Isolated nucleic acid molecules therefore are distinguished from the GLM-R-encoding nucleic acid molecule as it exists in natural cells. However, an isolated nucleic acid molecule encoding a GLM-R polypeptide includes GLM-R-encoding nucleic acid molecules contained in cells that ordinarily express GLM-R where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "antibody" is used in the broadest sense and specifically covers, for example, single anti-GLM-R monoclonal antibodies (including agonist, antagonist, and neutralizing antibodies), anti-GLM-R antibody compositions with polyepitopic specificity, single chain anti-GLM-R antibodies, and fragments of anti-GLM-R antibodies (see below). The term "monoclonal antibody" as used herein refers to an antibody obtained from a population of substantially homogeneous antibodies, i.e., the individual antibodies comprising the population are identical except for possible naturally-occurring mutations that may be present in minor amounts.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result; it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/ 0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5× Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The term "epitope tagged" when used herein refers to a chimeric polypeptide comprising a GLM-R polypeptide fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

"Active" or "activity" for the purposes herein refers to form(s) of GLM-R which retain a biological and/or an immunological activity of native or naturally-occurring GLM-R, wherein "biological" activity refers to a biological function (either inhibitory or stimulatory) caused by a native or naturally-occurring GLM-R other than the ability to induce the production of an antibody against an antigenic epitope possessed by a native or naturally-occurring GLM-R and an "immunological" activity refers to the ability to induce the production of an antibody against an antigenic epitope possessed by a native or naturally-occurring GLM-R. A preferred biological activity includes any one or more of the following activities: decreased body weight, decreased adiposity (e.g., fat/body weight ratio), increased lean muscle mass. Alternative definitions of biological activity include the ability to activate STAT-3 or STAT-5.

The term "antagonist" is used in the broadest sense, and includes any molecule that partially or fully blocks, inhibits or neutralizes a biological activity of a native GLM-R polypeptide disclosed herein. In a similar manner, the term "agonist" is used in the broadest sense and includes any molecule that mimics a biological activity of a native GLM-R polypeptide disclosed herein. Suitable agonist or antagonist molecules specifically include agonist or antagonist antibodies or antibody fragments, fragments or amino acid sequence variants of native GLM-R polypeptides, peptides, small organic molecules, etc. Methods for identifying agonists or antagonists of a GLM-R polypeptide may comprise contacting a GLM-R polypeptide with a candidate agonist or antagonist molecule and measuring a detectable change in one or more biological activities normally associated with the GLM-R polypeptide.

It is understood that some of the activities of GLM-R are directly induced by GLM-R and some are indirectly induced, however, each are the result of the presence of GLM-R and would not otherwise have the result in the absence of GLM-R.

"Treatment" is an intervention performed with the intention of preventing the development or altering the pathology of a disorder. Accordingly, "treatment" refers to both therapeutic treatment and prophylactic or preventative measures, wherein the object is to prevent or slow down (lessen) the targeted pathological condition or disorder. Individuals in need of treatment include those already with the disorder as well as those in which the disorder is to be prevented.

The term "effective amount" is at least the minimum concentration of GLM-R which causes, induces or results in either a detectable improvement in an in vitro cell-based model of a body weight disorder. For example, decreased glucose uptake into adipocytes, increased leptin release from adipocytes, etc. Furthermore, a "therapeutically effective amount" is at least the minimum concentration (amount) of GLM-R administered to a mammal which would be effective in at least attenuating or improving a pathological symptom associated with a body weight disorder. For example, decreased body weight, decreased fat/body weight ratio, increase lean muscle mass/body weight ratio, increased metabolic rate, decreased serum triglycerides or fatty acids, etc.

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

"Mammal" for purposes of treatment refers to any animal classified as a mammal, including humans, domestic and farm animals, and zoo, sports, or pet animals, such as dogs, cats, cattle, horses, sheep, pigs, goats, rabbits, ferrets, etc. Preferably, the mammal is human.

"Individual" is any subject patient, preferably a mammal, more preferably a human.

Administration "in combination with" one or more further therapeutic agents includes simultaneous (concurrent) and consecutive administration in any order.

The term "antagonist" is used in the broadest sense, and includes any molecule that partially or fully blocks, inhibits, or neutralizes a biological activity of a native GLM-R polypeptide disclosed herein. In a similar manner, the term "agonist" is used in the broadest sense and includes any molecule that mimics a biological activity of a native GLM-R polypeptide disclosed herein. Suitable agonist or antagonist molecules specifically include agonist or antagonist antibodies or antibody fragments, fragments or amino acid sequence variants of native GLM-R polypeptides, peptides, small organic molecules, etc. Methods for identifying agonists or antagonists of a GLM-R polypeptide may comprise contacting a GLM-R polypeptide with a candidate agonist or antagonist molecule and measuring a detectable change in one or more biological activities normally associated with the GLM-R polypeptide.

"Carriers" as used herein include pharmaceutically acceptable carriers, excipients, or stabilizers which are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (Zapata et al., *Protein Eng.* 8(10): 1057-1062 [1995]); single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')$_2$ fragment that has two antigen-combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2.

"Single-chain Fv" or "sFv" antibody fragments comprise the VH and VL domains of antibody, wherein these domains are present in a single polypeptide chain. Preferably, the Fv polypeptide further comprises a polypeptide linker between the VH and VL domains which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA* 90:6444-6448 (1993).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An antibody that "specifically binds to" or is "specific for" a particular polypeptide or an epitope on a particular polypeptide is one that binds to that particular polypeptide or epitope on a particular polypeptide without substantially binding to any other polypeptide or polypeptide epitope.

The word "label" when used herein refers to a detectable compound or composition which is conjugated directly or indirectly to the antibody so as to generate a "labeled" antibody. The label may be detectable by itself (e.g. radioisotope labels or fluorescent labels) or, in the case of an enzymatic label, may catalyze chemical alteration of a substrate compound or composition which is detectable.

By "solid phase" is meant a non-aqueous matrix to which the antibody of the present invention can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as a GLM-R polypeptide or antibody thereto) to a mammal. The components of the liposome are commonly arranged in a bilayer formation, similar to the lipid arrangement of biological membranes.

A "small molecule" is defined herein to have a molecular weight below about 500 Daltons.

Table 1

```
/*
 *
 * C-C increased from 12 to 15
 * Z is average of EQ
 * B is average of ND
 * match with stop is _M; stop-stop = 0; J (joker) match = 0
 */
define _M    -8     /* value of a match with a stop */ int     _day[26][26] = {
/*      A B C D E F G H I J K L M N O P Q R S T U V W X Y Z */
/* A */ { 2, 0,-2, 0, 0,-4, 1,-1,-1, 0,-1,-2,-1, 0,_M, 1, 0,-2, 1, 1, 0, 0,-6, 0,-3, 0},
/* B */ { 0, 3,-4, 3, 2,-5, 0, 1,-2, 0, 0,-3,-2, 2,_M,-1, 1, 0, 0, 0, 0,-2,-5, 0,-3, 1},
/* C */ {-2,-4,15,-5,-5,-4,-3,-3,-2, 0,-5,-6,-5,-4,_M,-3,-5,-4, 0,-2, 0,-2,-8, 0, 0,-5},
/* D */ { 0, 3,-5, 4, 3,-6, 1, 1,-2, 0, 0,-4,-3, 2,_M,-1, 2,-1, 0, 0, 0,-2,-7, 0,-4, 2},
/* E */ { 0, 2,-5, 3, 4,-5, 0, 1,-2, 0, 0,-3,-2, 1,_M,-1, 2,-1, 0, 0, 0,-2,-7, 0,-4, 3},
/* F */ {-4,-5,-4,-6,-5, 9,-5,-2, 1, 0,-5, 2, 0,-4,_M,-5,-5,-4,-3,-3, 0,-1, 0, 0, 7,-5},
/* G */ { 1, 0,-3, 1, 0,-5, 5,-2,-3, 0,-2,-4,-3, 0,_M,-1,-1,-3, 1, 0, 0,-1,-7, 0,-5, 0},
/* H */ {-1, 1,-3, 1, 1,-2,-2, 6,-2, 0, 0,-2,-2, 2,_M, 0, 3, 2,-1,-1, 0,-2,-3, 0, 0, 2},
/* I */ {-1,-2,-2,-2,-2, 1,-3,-2, 5, 0,-2, 2, 2,-2,_M,-2,-2,-2,-1, 0, 0, 4,-5, 0,-1,-2},
/* J */ { 0, 0, 0, 0, 0, 0, 0, 0, 0, 0, 0, 0, 0, 0,_M, 0, 0, 0, 0, 0, 0, 0, 0, 0, 0, 0},
/* K */ {-1, 0,-5, 0, 0,-5,-2, 0,-2, 0, 5,-3, 0, 1,_M,-1, 1, 3, 0, 0, 0,-2,-3, 0,-4, 0},
/* L */ {-2,-3,-6,-4,-3, 2,-4,-2, 2, 0,-3, 6, 4,-3,_M,-3,-2,-3,-3,-1, 0, 2,-2, 0,-1,-2},
/* M */ {-1,-2,-5,-3,-2, 0,-3,-2, 2, 0, 0, 4, 6,-2,_M,-2,-1, 0, 2,-1, 0, 2,-4, 0,-2,-1},
/* N */ { 0, 2,-4, 2, 1,-4, 0, 2,-2, 0, 1,-3,-2, 2,_M,-1, 1, 0, 1, 0, 0,-2,-4, 0,-2, 1},
/* O */ {_M,_M,_M,_M,_M,_M,_M,_M,_M,_M,_M,_M,_M,_M,
0,_M,_M,_M,_M,_M,_M,_M,_M,_M,_M,_M},
/* P */ { 1,-1,-3,-1,-1,-5,-1, 0,-2, 0,-1,-3,-2,-1,_M, 6, 0, 0, 1, 0, 0,-1,-6, 0,-5, 0},
/* Q */ { 0, 1, 5, 2, 2,-5,-1, 3,-2, 0, 1,-2,-1, 1,_M, 0, 4, 1,-1,-1, 0,-2,-5, 0,-4, 3},
/* R */ {-2, 0,-4,-1,-1,-4,-3, 2,-2, 0, 3,-3, 0, 0,_M, 0, 1, 6, 0,-1, 0,-2, 2, 0,-4, 0},
/* S */ { 1, 0, 0, 0, 0,-3, 1,-1,-1, 0, 0,-3,-2, 1,_M, 1,-1, 0, 2, 1, 0,-1,-2, 0,-3, 0},
/* T */ { 1, 0,-2, 0, 0,-3, 0,-1, 0, 0, 0,-1,-1, 0,_M, 0,-1,-1, 1, 3, 0, 0,-5, 0,-3, 0},
/* U */ { 0, 0, 0, 0, 0, 0, 0, 0, 0, 0, 0, 0, 0, 0,_M, 0, 0, 0, 0, 0, 0, 0, 0, 0, 0, 0},
/* V */ { 0,-2,-2,-2,-2,-1,-1,-2, 4, 0,-2, 2, 2,-2,_M,-1,-2,-2,-1, 0, 0, 4,-6, 0,-2,-2},
/* W */ {-6,-5,-8,-7,-7, 0,-7,-3,-5, 0,-3,-2,-4,-4,_M,-6,-5, 2,-2,-5, 0,-6,17, 0, 0,-6},
/* X */ { 0, 0, 0, 0, 0, 0, 0, 0, 0, 0, 0, 0, 0, 0,_M, 0, 0, 0, 0, 0, 0, 0, 0, 0, 0, 0},
/* Y */ {-3,-3, 0,-4,-4, 7,-5, 0,-1, 0,-4,-1,-2,-2,_M,-5,-4,-4,-3,-3, 0,-2, 0, 0,10,-4},
/* Z */ { 0, 1,-5, 2, 3,-5, 0, 2,-2, 0, 0,-2,-1, 1,_M, 0, 3, 0, 0, 0, 0,-2,-6, 0,-4, 4}
};
```

Page 1 of day.h

Table 1 (cont. 1)

```c
/*
*/
#include <stdio.h>
include <ctype.h> define MAXJMP   16      /* max jumps in a diag */
define MAXGAP   24      /* don't continue to penalize gaps larger than this */
#define JMPS     1024    /* max jmps in an path */
define MX       4       /* save if there's at least MX-1 bases since last jmp */ define DMAT     3       /* value of matching bases */
define DMIS     0       /* penalty for mismatched bases */
#define DINS0    8       /* penalty for a gap */
#define DINS1    1       /* penalty per base */
#define PINS0    8       /* penalty for a gap */
define PINS1    4       /* penalty per residue */ struct jmp {
        short           n[MAXJMP];      /* size of jmp (neg for dely) */
        unsigned short  x[MAXJMP];      /* base no. of jmp in seq x */
                                        /* limits seq to 2^16 -1 */
};

struct diag {
        int             score;          /* score at last jmp */
        long            offset;         /* offset of prev block */
        short           ijmp;           /* current jmp index */
        struct jmp      jp;             /* list of jmps */
};

struct path {
        int             spc;            /* number of leading spaces */
        short           n[JMPS];        /* size of jmp (gap) */
        int             x[JMPS];        /* loc of jmp (last elem before gap) */
};

char    *ofile;                         /* output file name */
char    *namex[2];                      /* seq names: getseqs( ) */
char    *prog;                          /* prog name for err msgs */
char    *seqx[2];                       /* seqs: getseqs( ) */
int     dmax;                           /* best diag: nw( ) */
int     dmax0;                          /* final diag */
int     dna;                            /* set if dna: main( ) */
int     endgaps;                        /* set if penalizing end gaps */
int     gapx, gapy;                     /* total gaps in seqs */
int     len0, len1;                     /* seq lens */
int     ngapx, ngapy;                   /* total size of gaps */
int     smax;                           /* max score: nw( ) */
int     *xbm;                           /* bitmap for matching */
long    offset;                         /* current offset in jmp file */
struct diag   *dx;                      /* holds diagonals */
struct path   pp[2];                    /* holds path for seqs */ char    *calloc( ), *malloc( ), *index( ), *strcpy( );
char    *getseq( ), *g_calloc( );
```

Page 1 of nw.h

Table 1 (cont. 2)

```
/* Needleman-Wunsch alignment program
*
* usage: progs file1 file2
*   where file1 and file2 are two dna or two protein sequences.
*   The sequences can be in upper- or lower-case an may contain ambiguity
*   Any lines beginning with ';', '>' or '<' are ignored
*   Max file length is 65535 (limited by unsigned short x in the jmp struct)
*   A sequence with 1/3 or more of its elements ACGTU is assumed to be DNA
*   Output is in the file "align.out"
*
* The program may create a tmp file in /tmp to hold info about traceback.
* Original version developed under BSD 4.3 on a vax 8650
*/
include "nw.h"
#include "day.h"

static  _dbval[26] = {
        1,14,2,13,0,0,4,11,0,0,12,0,3,15,0,0,0,5,6,8,8,7,9,0,10,0
};

static  _pbval[26] = {
        1, 2|(1<<('D'-'A'))|(1<<('N'-'A')), 4, 8, 16, 32, 64,
        128, 256, 0xFFFFFFFF, 1<<10, 1<<11, 1<<12, 1<<13, 1<<14,
        1<<15, 1<<16, 1<<17, 1<<18, 1<<19, 1<<20, 1<<21, 1<<22,
        1<<23, 1<<24, 1<<25|(1<<('E'-'A'))|(1<<('Q'-'A'))
};

main(ac, av)                                                              main
        int     ac;
        char    *av[];
{
        prog = av[0];
        if (ac != 3) {
                fprintf(stderr,"usage: %s file1 file2\n", prog);
                fprintf(stderr,"where file1 and file2 are two dna or two protein sequences.\n");
                fprintf(stderr,"The sequences can be in upper- or lower-case\n");
                fprintf(stderr,"Any lines beginning with ';' or '<' are ignored\n");
                fprintf(stderr,"Output is in the file \"align.out\"\n");
                exit(1);
        }
        namex[0] = av[1];
        namex[1] = av[2];
        seqx[0] = getseq(namex[0], &len0);
        seqx[1] = getseq(namex[1], &len1);
        xbm = (dna)? _dbval : _pbval;

endgaps = 0;            /* 1 to penalize endgaps */
        ofile = "align.out";    /* output file */ nw( );                  /* fill in the matrix, get the possible jmps */
        readjmps( );            /* get the actual jmps */
        print( );               /* print stats, alignment */ cleanup(0);             /* unlink any tmp files */
}
```

Page 1 of nw.c

Table 1 (cont. 3)

```
/* do the alignment, return best score: main( )
 * dna: values in Fitch and Smith, PNAS, 80, 1382-1386, 1983
 * pro: PAM 250 values
 * When scores are equal, we prefer mismatches to any gap, prefer
 * a new gap to extending an ongoing gap, and prefer a gap in seqx
 * to a gap in seq y.
 */
nw( )
{
        char            *px, *py;              /* seqs and ptrs */
        int             *ndely, *dely;         /* keep track of dely */
        int             ndelx, delx;           /* keep track of delx */
        int             *tmp;                  /* for swapping row0, row1 */
        int             mis;                   /* score for each type */
        int             ins0, ins1;            /* insertion penalties */
        register        id;                    /* diagonal index */
        register        ij;                    /* jmp index */
        register        *col0, *col1;          /* score for curr, last row */
        register        xx, yy;                /* index into seqs */ dx = (struct diag *)g_calloc("to get diags", len0+len1+1, sizeof(struct diag));

ndely = (int *)g_calloc("to get ndely", len1+1, sizeof(int));
        dely  = (int *)g_calloc("to get dely", len1+1, sizeof(int));
        col0  = (int *)g_calloc("to get col0", len1+1, sizeof(int));
        col1  = (int *)g_calloc("to get col1", len1+1, sizeof(int));
        ins0 = (dna)? DINS0 : PINS0;
        ins1 = (dna)? DINS1 : PINS1;

smax = -10000;
        if (endgaps) {
                for (col0[0] = dely[0] = -ins0, yy = 1; yy <= len1; yy++) {
                        col0[yy] = dely[yy] = col0[yy-1] - ins1;
                        ndely[yy] = yy;
                }
                col0[0] = 0;    /* Waterman Bull Math Biol 84 */
        }
        else
                for (yy = 1; yy <= len1; yy++)
                        dely[yy] = -ins0;

/* fill in match matrix
         */
        for (px = seqx[0], xx = 1; xx <= len0; px++, xx++) {
                /* initialize first entry in col
                 */
                if (endgaps) {
                        if (xx == 1)
                                col1[0] = delx = -(ins0+ins1);
                        else
                                col1[0] = delx = col0[0] - ins1;
                        ndelx = xx;
                }
                else {
                        col1[0] = 0;
                        delx = -ins0;
                        ndelx = 0;
                }
``` page 2 of nw.c

Table 1 (cont. 4)

...nw

```
for (py = seqx[1], yy = 1; yy <= len1; py++, yy++) {
        mis = col0[yy-1];
        if (dna)
                mis += (xbm[*px-'A']&xbm[*py-'A'])? DMAT : DMIS;
        else
                mis += _day[*px-'A'][*py-'A'];

/* update penalty for del in x seq;
         * favor new del over ongong del
         * ignore MAXGAP if weighting endgaps
         */
        if (endgaps || ndely[yy] < MAXGAP) {
                if (col0[yy] - ins0 >= dely[yy]) {
                        dely[yy] = col0[yy] - (ins0+ins1);
                        ndely[yy] = 1;
                } else {
                        dely[yy] -= ins1;
                        ndely[yy]++;
                }
        } else {
                if (col0[yy] - (ins0+ins1) >= dely[yy]) {
                        dely[yy] = col0[yy] - (ins0+ins1);
                        ndely[yy] = 1;
                } else
                        ndely[yy]++;
        }

/* update penalty for del in y seq;
         * favor new del over ongong del
         */
        if (endgaps || ndelx < MAXGAP) {
                if (col1[yy-1] - ins0 >= delx) {
                        delx = col1[yy-1] - (ins0+ins1);
                        ndelx = 1;
                } else {
                        delx -= ins1;
                        ndelx++;
                }
        } else {
                if (col1[yy-1] - (ins0+ins1) >= delx) {
                        delx = col1[yy-1] - (ins0+ins1);
                        ndelx = 1;
                } else
                        ndelx++;
        }

/* pick the maximum score; we're favoring
         * mis over any del and delx over dely
         */
```

Table 1 (cont. 5)

```
                        id = xx - yy + len1 - 1;                                    ...nw
                        if (mis >= delx && mis >= dely[yy])
                                coll[yy] = mis;
                        else if (delx >= dely[yy]) {
                                coll[yy] = delx;
                                ij = dx[id].ijmp;
                                if (dx[id].jp.n[0] && (!dna || (ndelx >= MAXJMP
                                    && xx > dx[id].jp.x[ij]+MX) || mis > dx[id].score+DINS0)) {
                                        dx[id].ijmp++;
                                        if (++ij >= MAXJMP) {
                                                writejmps(id);
                                                ij = dx[id].ijmp = 0;
                                                dx[id].offset = offset;
                                                offset += sizeof(struct jmp) + sizeof(offset);
                                        }
                                }
                                dx[id].jp.n[ij] = ndelx;
                                dx[id].jp.x[ij] = xx;
                                dx[id].score = delx;
                        }
                        else {
                                coll[yy] = dely[yy];
                                ij = dx[id].ijmp;
                if (dx[id].jp.n[0] && (!dna || (ndely[yy] >= MAXJMP
                    && xx > dx[id].jp.x[ij]+MX) || mis > dx[id].score+DINS0)) {
                                        dx[id].ijmp++;
                                        if (++ij >= MAXJMP) {
                                                writejmps(id);
                                                ij = dx[id].ijmp = 0;
                                                dx[id].offset = offset;
                                                offset += sizeof(struct jmp) + sizeof(offset);
                                        }
                                }
                                dx[id].jp.n[ij] = -ndely[yy];
                                dx[id].jp.x[ij] = xx;
                                dx[id].score = dely[yy];
                        }
                        if (xx == len0 && yy < len1) {
                                /* last col
                                */
                                if (endgaps)
                                        coll[yy] -= ins0+ins1*(len1-yy);
                                if (coll[yy] > smax) {
                                        smax = coll[yy];
                                        dmax = id;
                                }
                        }
                }
                if (endgaps && xx < len0)
                        coll[yy-1] -= ins0+ins1*(len0-xx);
                if (coll[yy-1] > smax) {
                        smax = coll[yy-1];
                        dmax = id;
                }
                tmp = col0; col0 = coll; coll = tmp;
        }
        (void) free((char *)ndely);
        (void) free((char *)dely);
        (void) free((char *)col0);
        (void) free((char *)coll);
}
```

Table 1 (cont. 6)

```
/*
 *
 * print( ) -- only routine visible outside this module
 *
 * static:
 * getmat( ) -- trace back best path, count matches: print( )
 * pr_align( ) -- print alignment of described in array p[]: print( )
 * dumpblock( ) -- dump a block of lines with numbers, stars: pr_align( )
 * nums( ) -- put out a number line: dumpblock( )
 * putline( ) -- put out a line (name, [num], seq, [num]): dumpblock( )
 * stars( ) - -put a line of stars: dumpblock( )
 * stripname( ) -- strip any path and prefix from a seqname
 */ include "nw.h"

define SPC     3
#define P_LINE  256     /* maximum output line */
define P_SPC   3       /* space between name or num and seq */ extern  _day[26][26];
int     olen;           /* set output line length */
FILE    *fx;            /* output file */ print( )                                                                print
{
        int     lx, ly, firstgap, lastgap;      /* overlap */ if ((fx = fopen(ofile, "w")) == 0) {
                fprintf(stderr,"%s: can't write %s\n", prog, ofile);
                cleanup(1);
        }
        fprintf(fx, "<first sequence: %s (length = %d)\n", namex[0], len0);
        fprintf(fx, "<second sequence: %s (length = %d)\n", namex[1], len1);
        olen = 60;
        lx = len0;
        ly = len1;
        firstgap = lastgap = 0;
        if (dmax < len1 - 1) {  /* leading gap in x */
                pp[0].spc = firstgap = len1 - dmax - 1;
                ly -= pp[0].spc;
        }
        else if (dmax > len1 - 1) {     /* leading gap in y */
                pp[1].spc = firstgap = dmax - (len1 - 1);
                lx -= pp[1].spc;
        }
        if (dmax0 < len0 - 1) { /* trailing gap in x */
                lastgap = len0 - dmax0 -1;
                lx -= lastgap;
        }
        else if (dmax0 > len0 - 1) {    /* trailing gap in y */
                lastgap = dmax0 - (len0 - 1);
                ly -= lastgap;
        }
        getmat(lx, ly, firstgap, lastgap);
        pr_align( );
}
```

Page 1 of nwprint.c

Table 1 (cont. 7)

```
/*
 * trace back the best path, count matches
 */
static
getmat(lx, ly, firstgap, lastgap)
        int     lx, ly;                 /* "core" (minus endgaps) */
        int     firstgap, lastgap;      /* leading trailing overlap */
{
        int             nm, i0, i1, siz0, siz1;
        char            outx[32];
        double          pct;
        register        n0, n1;
        register char   *p0, *p1;

/* get total matches, score
         */
        i0 = i1 = siz0 = siz1 = 0;
        p0 = seqx[0] + pp[1].spc;
        p1 = seqx[1] + pp[0].spc;
        n0 = pp[1].spc + 1;
        n1 = pp[0].spc + 1;

nm = 0;
        while ( *p0 && *p1 ) {
                if (siz0) {
                        p1++;
                        n1++;
                        siz0--;
                }
                else if (siz1) {
                        p0++;
                        n0++;
                        siz1--;
                }
                else {
                        if (xbm[*p0-'A']&xbm[*p1-'A'])
                                nm++;
                        if (n0++ == pp[0].x[i0])
                                siz0 = pp[0].n[i0++];
                        if (n1++ == pp[1].x[i1])
                                siz1 = pp[1].n[i1++];
                        p0++;
                        p1++;
                }
        }

/* pct homology:
         * if penalizing endgaps, base is the shorter seq
         * else, knock off overhangs and take shorter core
         */
        if (endgaps)
                lx = (len0 < len1)? len0 : len1;
        else
                lx = (lx < ly)? lx : ly;
        pct = 100.*(double)nm/(double)lx;
        fprintf(fx, "\n");
        fprintf(fx, " <%d match%s in an overlap of %d: %.2f percent similarity\n",
                nm, (nm == 1)? "" : "es", lx, pct);
``` getmat

Table 1 (cont. 8)

```
                fprintf(fx, "<gaps in first sequence: %d", gapx);                                    ...getmat
                if (gapx) {
                        (void) sprintf(outx, " (%d %s%s)",
                                ngapx, (dna)? "base":"residue", (ngapx == 1)? "":"s");
                        fprintf(fx,"%s", outx);

fprintf(fx, ", gaps in second sequence: %d", gapy);
                if (gapy) {
                        (void) sprintf(outx, " (%d %s%s)",
                                ngapy, (dna)? "base":"residue", (ngapy == 1)? "":"s");
                        fprintf(fx,"%s", outx);
                }
        if (dna)
                fprintf(fx,
                "\n<score: %d (match = %d, mismatch = %d, gap penalty = %d + %d per base)\n",
                smax, DMAT, DMIS, DINS0, DINS1);
        else
                fprintf(fx,
                "\n<score: %d (Dayhoff PAM 250 matrix, gap penalty = %d + %d per residue)\n",
                smax, PINS0, PINS1);
        if (endgaps)
                fprintf(fx,
                "<endgaps penalized. left endgap: %d %s%s, right endgap: %d %s%s\n",
                firstgap, (dna)? "base" : "residue", (firstgap == 1)? "" : "s",
                lastgap, (dna)? "base" : "residue", (lastgap == 1)? "" : "s");
        else
                fprintf(fx, "<endgaps not penalized\n");
} static          nm;             /* matches in core -- for checking */
static          lmax;           /* lengths of stripped file names */
static          ij[2];          /* jmp index for a path */
static          nc[2];          /* number at start of current line */
static          ni[2];          /* current elem number -- for gapping */
static          siz[2];
static char     *ps[2];         /* ptr to current element */
static char     *po[2];         /* ptr to next output char slot */
static char     out[2][P_LINE]; /* output line */
static char     star[P_LINE];   /* set by stars( ) */
/*
* print alignment of described in struct path pp[]
*/
static
pr_align( )                                                                                          pr_align
{
        int             nn;     /* char count */
        int             more;
        register        i;

for (i = 0, lmax = 0; i < 2; i++) {
                nn = stripname(namex[i]);
                if (nn > lmax)
                        lmax = nn;

nc[i] = 1;
                ni[i] = 1;
                siz[i] = ij[i] = 0;
                ps[i] = seqx[i];
                po[i] = out[i];
        }
```

Table 1 (cont. 9)

```
for (nn = nm = 0, more = 1; more; ) {                                    ...pr_align
        for (i = more = 0; i < 2; i++) {
                /*
                 * do we have more of this sequence?
                 */
                if (!*ps[i])
                        continue;

more++;

if (pp[i].spc) {    /* leading space */
                        *po[i]++ = ' ';
                        pp[i].spc--;
                }
                else if (siz[i]) {   /* in a gap */
                        *po[i]++ = '-';
                        siz[i]--;
                }
                else {               /* we're putting a seq element
                                      */
                        *po[i] = *ps[i];
                        if (islower(*ps[i]))
                                *ps[i] = toupper(*ps[i]);
                        po[i]++;
                        ps[i]++;

/*
                         * are we at next gap for this seq?
                         */
                        if (ni[i] == pp[i].x[ij[i]]) {
                                /*
                                 * we need to merge all gaps
                                 * at this location
                                 */
                                siz[i] = pp[i].n[ij[i]++];
                                while (ni[i] == pp[i].x[ij[i]])
                                        siz[i] += pp[i].n[ij[i]++];
                        }
                        ni[i]++;
                }
        }
        if (++nn == olen || !more && nn) {
                dumpblock();
                for (i = 0; i < 2; i++)
                        po[i] = out[i];
                nn = 0;
        }
    }
}

/*
 * dump a block of lines, including numbers, stars: pr_align( )
 */
static                                                                   dumpblock
dumpblock( )
{
        register i;
        for (i = 0; i < 2; i++)
                *po[i]-- = '\0';
```

Table 1 (cont. 10)

...dumpblock

```
            (void) putc('\n', fx);
            for (i = 0; i < 2; i++) {
                    if (*out[i] && (*out[i] != ' ' || *(po[i]) != ' ')) {
                            if (i == 0)
                                    nums(i);
                            if (i == 0 && *out[1])
                                    stars( );
                            putline(i);
                            if (i == 0 && *out[1])
                                    fprintf(fx, star);
                            if (i == 1)
                                    nums(i);
                    }
            }
}
/*
* put out a number line: dumpblock( )
*/
static
nums(ix)
        int       ix;        /* index in out[] holding seq line */
{
        char            nline[P_LINE];
        register        i, j;
        register char   *pn, *px, *py;

for (pn = nline, i = 0; i < lmax+P_SPC; i++, pn++)
                *pn = ' ';
        for (i = nc[ix], py = out[ix]; *py; py++, pn++) {
                if (*py == ' ' || *py == '-')
                        *pn = ' ';
                else {
                        if (i%10 == 0 || (i == 1 && nc[ix] != 1)) {
                                j = (i < 0)? -i : i;
                                for (px = pn; j; j /= 10, px--)
                                        *px = j%10 + '0';
                                if (i < 0)
                                        *px = '-';
                        }
                        else
                                *pn = ' ';
                        i++;
                }
        }
        *pn = '\0';
        nc[ix] = i;
        for (pn = nline; *pn; pn++)
                (void) putc(*pn, fx);
        (void) putc('\n', fx);
}

/*
* put out a line (name, [num], seq, [num]): dumpblock( )
*/
static
putline(ix)
        int       ix;
{
``` nums putline

Table 1 (cont. 11)

...putline

```
        int             i;
        register char   *px;

for (px = namex[ix], i = 0; *px && *px != ':'; px++, i++)
                (void) putc(*px, fx);
        for (; i < lmax+P_SPC; i++)
                (void) putc(' ', fx);

/* these count from 1:
         * ni[] is current element (from 1)
         * nc[] is number at start of current line
         */
        for (px = out[ix]; *px; px++)
                (void) putc(*px&0x7F, fx);
        (void) putc('\n', fx);
}

/*
 * put a line of stars (seqs always in out[0], out[1]): dumpblock( )
 */
static
stars( )                                                                                    stars
{
        int             i;
        register char   *p0, *p1, cx, *px;

if (!*out[0] || (*out[0] == ' ' && *(po[0]) == ' ') ||
            !*out[1] || (*out[1] == ' ' && *(po[1]) == ' '))
                return;
        px = star;
        for (i = lmax+P_SPC; i; i--)
                *px++ = ' ';

for (p0 = out[0], p1 = out[1]; *p0 && *p1; p0++, p1++) {
                if (isalpha(*p0) && isalpha(*p1)) { if (xbm[*p0-'A']&xbm[*p1-'A']) {
                                cx = '*';
                                nm++;
                        }
                        else if (!dna && _day[*p0-'A'][*p1-'A'] > 0)
                                cx = '.';
                        else
                                cx = ' ';
                }
                else
                        cx = ' ';
                *px++ = cx;
        }
        *px++ = '\n';
        *px = '\0';
}
```

Page 6 of nwprint.c

Table 1 (cont. 12)

```
/*
 * strip path or prefix from pn, return len: pr_align( )
 */
static
stripname(pn)
        char    *pn;    /* file name (may be path) */
{
        register char   *px, *py;

py = 0;
        for (px = pn; *px; px++)
                if (*px == '/')
                        py = px + 1;
        if (py)
                (void) strcpy(pn, py);
        return(strlen(pn));

}
``` stripname

Page 7 of nwprint.c

Table 1 (cont. 13)

```
/*
 * cleanup( ) -- cleanup any tmp file
 * getseq( ) -- read in seq, set dna, len, maxlen
 * g_calloc( ) -- calloc( ) with error checkin
 * readjmps( ) -- get the good jmps, from tmp file if necessary
 * writejmps( ) -- write a filled array of jmps to a tmp file: nw( )
 */
include "nw.h"
include <sys/file.h> char    *jname = "/tmp/homgXXXXXX";          /* tmp file for jmps */
FILE    *fj;

int     cleanup( );                          /* cleanup tmp file */
long    lseek( );

/*
 * remove any tmp file if we blow
 */
cleanup(i)                                                                      cleanup
        int     i;
{
        if (fj)
                (void) unlink(jname);
        exit(i);
}

/*
 * read, return ptr to seq, set dna, len, maxlen
 * skip lines starting with ';', '<', or '>'
 * seq in upper or lower case
 */
char    *
getseq(file, len)                                                               getseq
        char    *file;      /* file name */
        int     *len;       /* seq len */
{
        char            line[1024], *pseq;
        register char   *px, *py;
        int             natgc, tlen;
        FILE            *fp;

if ((fp = fopen(file,"r")) == 0) {
                fprintf(stderr,"%s: can't read %s\n", prog, file);
                exit(1);
        }
        tlen = natgc = 0;
        while (fgets(line, 1024, fp)) {
                if (*line == ';' || *line == '<' || *line == '>')
                        continue;
                for (px = line; *px != '\n'; px++)
                        if (isupper(*px) || islower(*px))
                                tlen++;
        }
        if ((pseq = malloc((unsigned)(tlen+6))) == 0) {
                fprintf(stderr,"%s: malloc( ) failed to get %d bytes for %s\n", prog, tlen+6, file);
                exit(1);
        }
        pseq[0] = pseq[1] = pseq[2] = pseq[3] = '\0';
```

Table 1 (cont. 14)

...getseq

```
        py = pseq + 4;
        *len = tlen;
        rewind(fp);

while (fgets(line, 1024, fp)) {
                if (*line == ';' || *line == '<' || *line == '>')
                        continue;
                for (px = line; *px != '\n'; px++) {
                        if (isupper(*px))
                                *py++ = *px;
                        else if (islower(*px))
                                *py++ = toupper(*px);
                        if (index("ATGCU",*(py-1)))
                                natgc++;
                }
        }
        *py++ = '\0';
        *py = '\0';
        (void) fclose(fp);
        dna = natgc > (tlen/3);
        return(pseq+4);
} char    *
g_calloc(msg, nx, sz)
        char    *msg;           /* program, calling routine */
        int     nx, sz;         /* number and size of elements */
{
        char    *px, *calloc( );

if ((px = calloc((unsigned)nx, (unsigned)sz)) == 0) {
                if (*msg) {
                        fprintf(stderr, "%s: g_calloc( ) failed %s (n=%d, sz=%d)\n", prog, msg, nx, sz);
                        exit(1);
                }
        }
        return(px);
}

/*
 * get final jmps from dx[] or tmp file, set pp[], reset dmax: main( )
 */
readjmps( )
{
        int     fd = -1;
        int     siz, i0, i1;
        register i, j, xx;

if (fj) {
                (void) fclose(fj);
                if ((fd = open(jname, O_RDONLY, 0)) < 0) {
                        fprintf(stderr, "%s: can't open( ) %s\n", prog, jname);
                        cleanup(1);
                }
        }
        for (i = i0 = i1 = 0, dmax0 = dmax, xx = len0; ; i++) {
                while (1) {
                        for (j = dx[dmax].ijmp; j >= 0 && dx[dmax].jp.x[j] >= xx; j--)
                                ;
``` g_calloc readjmps

Table 1 (cont. 15)

...readjmps

```
                if (j < 0 && dx[dmax].offset && fj) {
                        (void) lseek(fd, dx[dmax].offset, 0);
                        (void) read(fd, (char *)&dx[dmax].jp, sizeof(struct jmp));
                        (void) read(fd, (char *)&dx[dmax].offset, sizeof(dx[dmax].offset));
                        dx[dmax].ijmp = MAXJMP-1;
                }
                else
                        break;
        }
        if (i >= JMPS) {
                fprintf(stderr, "%s: too many gaps in alignment\n", prog);
                cleanup(1);
        }
        if (j >= 0) {
                siz = dx[dmax].jp.n[j];
                xx = dx[dmax].jp.x[j];
                dmax += siz;
                if (siz < 0) {              /* gap in second seq */
                        pp[1].n[i1] = -siz;
                        xx += siz;
                        /* id = xx - yy + len1 - 1
                         */
                        pp[1].x[i1] = xx - dmax + len1 - 1;
                        gapy++;
                        ngapy -= siz;
/* ignore MAXGAP when doing endgaps */
                        siz = (-siz < MAXGAP || endgaps)? -siz : MAXGAP;
                        i1++;
                }
                else if (siz > 0) {         /* gap in first seq */
                        pp[0].n[i0] = siz;
                        pp[0].x[i0] = xx;
                        gapx++;
                        ngapx += siz;
/* ignore MAXGAP when doing endgaps */
                        siz = (siz < MAXGAP || endgaps)? siz : MAXGAP;
                        i0++;
                }
        }
        else
                break;
}

/* reverse the order of jmps
 */
for (j = 0, i0--; j < i0; j++, i0--) {
        i = pp[0].n[j]; pp[0].n[j] = pp[0].n[i0]; pp[0].n[i0] = i;
        i = pp[0].x[j]; pp[0].x[j] = pp[0].x[i0]; pp[0].x[i0] = i;
}
for (j = 0, i1--; j < i1; j++, i1--) {
        i = pp[1].n[j]; pp[1].n[j] = pp[1].n[i1]; pp[1].n[i1] = i;
        i = pp[1].x[j]; pp[1].x[j] = pp[1].x[i1]; pp[1].x[i1] = i;
}
if (fd >= 0)
        (void) close(fd);
if (fj) {
        (void) unlink(jname);
        fj = 0;
        offset = 0;
}
```

Table 1 (cont. 16)

```c
/*
 * write a filled jmp struct offset of the prev one (if any): nw( )
 */
writejmps(ix)                                                                    writejmps
        int     ix;
{
        char    *mktemp( );

if (!fj) {
                if (mktemp(jname) < 0) {
                        fprintf(stderr, "%s: can't mktemp( ) %s\n", prog, jname);
                        cleanup(1);
                }
                if ((fj = fopen(jname, "w")) == 0) {
                        fprintf(stderr, "%s: can't write %s\n", prog, jname);
                        exit(1);
                }
        }
        (void) fwrite((char *)&dx[ix].jp, sizeof(struct jmp), 1, fj);
        (void) fwrite((char *)&dx[ix].offset, sizeof(dx[ix].offset), 1, fj);
}
```

Page 4 of nwsubr.c

TABLE 2

| | | |
|---|---|---|
| GLM-R | XXXXXXXXXXXXXXX | (Length = 15 amino acids) |
| Comparison Protein | XXXXXYYYYYYY | (Length = 12 amino acids) |

% amino acid sequence identity =
(the number of identically matching amino acid residues between the two polypeptide sequences as determined by ALIGN-2) divided by (the total number of amino acid residues of the GLM-R polypeptide) = 5 divided by 15 = 33.3%

TABLE 3

| | | |
|---|---|---|
| GLM-R | XXXXXXXXXX | (Length = 10 amino acids) |
| Comparison Protein | XXXXXYYYYYYZZYZ | (Length = 15 amino acids) |

% amino acid sequence identity =
(the number of identically matching amino acid residues between the two polypeptide sequences as determined by ALIGN-2) divided by (the total number of amino acid residues of the GLM-R polypeptide) = 5 divided by 10 = 50%

TABLE 4

| | | |
|---|---|---|
| GLM-R-DNA | NNNNNNNNNNNNNN | (Length = 14 nucleotides) |
| Comparison DNA | NNNNNNLLLLLLLLLL | (Length = 16 nucleotides) |

% nucleic acid sequence identity =
(the number of identically matching nucleotides between the two nucleic acid sequences as determined by ALIGN-2) divided by (the total number of nucleotides of the GLM-R-DNA nucleic acid sequence) = 6 divided by 14 = 42.9%

TABLE 5

| | | |
|---|---|---|
| GLM-R-DNA | NNNNNNNNNNNN | (Length = 12 nucleotides) |
| Comparison DNA | NNNNLLLVV | (Length = 9 nucleotides) |

% nucleic acid sequence identity =
(the number of identically matching nucleotides between the two nucleic acid sequences as determined by ALIGN-2) divided by (the total number of nucleotides of the GLM-R-DNA nucleic acid sequence) = 4 divided by 12 = 33.3%

II. Compositions and Methods of the Invention

The present invention describes a novel molecule that displays the typical architecture and structural features of type 1 receptors. It shares significant homology to known members of this receptor family, most notably gp130 and GCSF-R, and is found in close physical proximity to gp130 on human chromosome 5 and mouse chromosome 13.

GLM-R was found to be expressed predominantly on activated monocytes. In support of this finding, GLM-R was expressed in two monocytic cell lines, THP-1 and U937, but not in a number of other cell lines of lymphoid and myeloid origin. Furthermore, strong induction of GLM-R upon stimulation with LPS and IFN-γ was seen in monocytes and in the two cell lines (not shown). Together, these expression data suggest that monocytes and possibly macrophages are a likely site of physiologic activity of this receptor, and prompt further analysis of GLM-R's function in those cells. Expression in monocytes accounts for the elevated GLM-R levels detected in thymus and bone marrow. On the other hand, presence of GLM-R in testis and prostate suggests that it has additional functions outside the immune system The capacity of GLM-R to signal was examined by fusing its intracellular domain to the ligand binding domain of hGH-R, a receptor that is well known to homodimerize upon stimulation with hGH. The resulting chimeric molecule was able to transduce a proliferative signal into myeloid 32D cells, and caused activation of the transcription factors STAT-3 and, to a lesser extent, STAT-5. Thus, GLM-R is capable of signaling, but it remains to be determined whether its extracellular domain binds a ligand by itself, or whether additional receptor subunits are required to form a functional receptor. Using proliferation of 32D cells transfected with the full length human molecule as a readout, we found that GLM-R is not a sufficient receptor for IL-2, -3, -4, -5, -6, -7, -9, -11, -12, -13, -15, -23, GCSF, GM-CSF, EPO, TPO, PRL, GH, OSM, CT-1 and OB (not shown). These cells can now be used to screen a variety of sources for a GLM-R ligand, but such a strategy will only be successful if either GLM-R can act as a homodimer, or if the necessary accessory chains are endogenously expressed in 32D cells.

GLM-R preferentially activated STAT-3, while STAT-5 activation was low but nonetheless detectable. These two proteins were shown to have very different functions in myeloid cells. Enforced expression of constitutively active STAT-5a or STAT-5b resulted in factor independence and myeloid differentiation of BaF3 cells [Nosaka et al., Embo J. 18(17): 4754-65 (1999)], and macrophage differentiation of M1 cells [Kawashima et al., J. Immunol. 167(7):3652-60 (2001)], while macrophages deficient in STAT-5a displayed a defect in GM-CSF induced proliferation and gene expression. Feldman et al., Blood 90(5): 1768-76 (1997). Moreover, repopulation of all blood cell lineages, including monocytes, was severely compromised when STAT-5a-/-5b-/-bone marrow cells instead of wild-type cells were used as a graft to rescue lethally irradiated animals. Bunting et al., Blood 99(2): 479-487 (2002). Together, these data suggest that STAT-5 plays an important role in the development and proliferation of monocytes/macrophages. On the other hand, STAT-3 appears to be involved in the negative regulation of macrophage activation, a function mainly exerted by IL-10. Riley et al., J. Biol. Chem. 274(23), 16513-16521 (1999), O'Farrell et al., Embo. J. 17(4): 1006-18 (1998). In a mouse model in which STAT-3 was deleted in a tissue specific fashion in macrophages and neutrophils, macrophages were consitutively activated, which led to chronic enterocolitis through activation of Th1 cells in vivo [Takeda, K. et al., Immunity 10(1): 39-49 (1999)], a phenotype that is mimicked by IL-10 deficient mice. Kuhn et al., Cell 75(2): 263-74 (1993).

Taken together, our data suggests that GLM-R is a receptor for a yet unknown helical cytokine that likely acts on monocytes and possibly also macrophages. Using the receptor as a tool, it will hopefully be possible to identify this ligand, which is critical in order to further understand the biological function of GLM-R.

A. Full-Length GLM-R Polypeptide

The present invention provides newly identified and isolated nucleotide sequences encoding polypeptides referred to in the present application as GLM-R (alternatively PRO21073 or UNQ6368). In particular, cDNA encoding a GLM-R polypeptide has been identified and isolated, as disclosed in further detail in the Examples below. It is noted that proteins produced in separate expression rounds may be given different PRO numbers but the UNQ number is unique for any given DNA and the encoded protein, and will not be changed. However, for sake of simplicity, in the present specification the protein encoded by DNA173920-2924 as well as all further native homologues and variants included in the foregoing definition of GLM-R (also sometimes referred to as PRO21073), will be referred to as "GLM-R", regardless of their origin or mode of preparation.

As disclosed in the Examples below, cDNA clones designated herein as DNA173920-2924 have been deposited with the ATCC. The actual nucleotide sequence of the clones can readily be determined by the skilled artisan by sequencing of the deposited clones using routine methods in the art. The predicted amino acid sequence can be determined from the nucleotide sequence using routine skill. For the GLM-R polypeptides and encoding nucleic acid described herein, Applicants have identified what is believed to be the reading frame best identifiable with the sequence information available at the time.

B. GLM-R Variants

In addition to the full-length native sequence GLM-R polypeptides described herein, it is contemplated that GLM-R variants can be prepared. GLM-R variants can be prepared by introducing appropriate nucleotide changes into the GLM-R DNA, and/or by synthesis of the desired GLM-R polypeptide. Those skilled in the art will appreciate that amino acid changes may alter post-translational processes of the GLM-R, such as changing the number or position of glycosylation sites or altering the membrane anchoring characteristics.

Variations in the native full-length sequence GLM-R or in various domains of the GLM-R described herein, can be made, for example, using any of the techniques and guidelines for conservative and non-conservative mutations set forth, for instance, in U.S. Pat. No. 5,364,934. Variations may be a substitution, deletion or insertion of one or more codons encoding the GLM-R that results in a change in the amino acid sequence of the GLM-R as compared with the native sequence GLM-R. Optionally the variation is by substitution of at least one amino acid with any other amino acid in one or more of the domains of the GLM-R. Guidance in determining which amino acid residue may be inserted, substituted or deleted without adversely affecting the desired activity may be found by comparing the sequence of the GLM-R with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence.

GLM-R polypeptide fragments are provided herein. Such fragments may be truncated at the N-terminus or C-terminus, or may lack internal residues, for example, when compared with a full length native protein. Certain fragments lack amino acid residues that are not essential for a desired biological activity of the GLM-R polypeptide.

GLM-R fragments may be prepared by any of a number of conventional techniques. Desired peptide fragments may be chemically synthesized. An alternative approach involves generating GLM-R fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired polypeptide fragment, by polymerase chain reaction (PCR). Oligonucleotides that define the desired termini of the DNA fragment are employed at the 5' and 3' primers in the PCR. Preferably, GLM-R polypeptide fragments share at least one biological and/or immunological activity with the native GLM-R polypeptide shown in FIG. 2 (SEQ ID NO:2).

In particular embodiments, conservative substitutions of interest are shown in Table 6 under the heading of preferred substitutions. If such substitutions result in a change in biological activity, then more substantial changes, denominated exemplary substitutions in Table 6, or as further described below in reference to amino acid classes, are introduced and the products screened.

TABLE 6

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in function or immunological identity of the GLM-R polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;

(2) neutral hydrophilic: cys, ser, thr;

(3) acidic: asp, glu;

(4) basic: asn, gln, his, lys, arg;

(5) residues that influence chain orientation: gly, pro; and (6) aromatic: trp, tyr, phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis [Carter et al., *Nucl. Acids Res.*, 13:4331 (1986); Zoller et al., *Nucl. Acids Res.*, 10:6487 (1987)], cassette mutagenesis [Wells et al., *Gene*, 34:315 (1985)], restriction selection mutagenesis [Wells et al., *Philos. Trans. R. Soc. London SerA*, 317:415 (1986)] or other known techniques can be performed on the cloned DNA to produce the GLM-R variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, *Science,* 244: 1081-1085 (1989)]. Alanine is also typically preferred because it is the most common amino acid. Further, it is frequently found in both buried and exposed positions [Creighton, *The Proteins*, (W.H. Freeman & Co., N.Y.); Chothia, *J. Mol. Biol.,* 150:1 (1976)]. If alanine substitution does not yield adequate amounts of variant, an isosteric amino acid can be used.

C. Modifications of GLM-R

Covalent modifications of GLM-R are included within the scope of this invention. One type of covalent modification includes reacting targeted amino acid residues of GLM-R polypeptides with an organic derivatizing agent that is capable of reacting with selected side chains or the N- or C-terminal residues of the GLM-R. Derivatization with bifunctional agents is useful, for instance, for crosslinking GLM-R to a water-insoluble support matrix or surface for use in the method for purifying anti-GLM-R antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the $\alpha$-amino groups of lysine, arginine, and histidine side chains [T. E. Creighton, *Proteins: Structure and Molecular Properties*, W.H. Freeman & Co., San Francisco, pp. 79-86 (1983)], acetylation of the N-terminal amine, and amidation of any C-terminal carboxyl group.

Another type of covalent modification of the GLM-R polypeptide included within the scope of this invention comprises altering the native glycosylation pattern of the polypeptide. "Altering the native glycosylation pattern" is intended for purposes herein to mean deleting one or more carbohydrate moieties found in native sequence GLM-R (either by removing the underlying glycosylation site or by deleting the glycosylation by chemical and/or enzymatic means), and/or adding one or more glycosylation sites that are not present in the native sequence GLM-R. In addition, the phrase includes qualitative changes in the glycosylation of the native proteins, involving a change in the nature and proportions of the various carbohydrate moieties present.

Addition of glycosylation sites to the GLM-R polypeptide may be accomplished by altering the amino acid sequence. The alteration may be made, for example, by the addition of, or substitution by, one or more serine or threonine residues to the native sequence GLM-R (for O-linked glycosylation sites). The GLM-R amino acid sequence may optionally be altered through changes at the DNA level, particularly by mutating the DNA encoding the GLM-R polypeptide at preselected bases such that codons are generated that will translate into the desired amino acids.

Another means of increasing the number of carbohydrate moieties on the GLM-R polypeptide is by chemical or enzymatic coupling of glycosides to the polypeptide. Such methods are described in the art, e.g., in WO 87/05330 published 11 Sep. 1987, and in Aplin and Wriston, *CRC Crit. Rev. Biochem*., pp. 259-306 (1981).

Removal of carbohydrate moieties present on the GLM-R polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys,* 259:52 (1987) and by Edge et al., *Anal. Biochem* 118:131 (1981). Enzymatic cleavage of carbohydrate moieties on polypeptides can be achieved by the use of a variety of endo- and exo-glycosidases as described by Thotakura et al., *Meth. Enzymol.,* 138:350 (1987).

Another type of covalent modification of GLM-R comprises linking the GLM-R polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

The GLM-R of the present invention may also be modified in a way to form a chimeric molecule comprising GLM-R fused to another, heterologous polypeptide or amino acid sequence.

In one embodiment, such a chimeric molecule comprises a fusion of the GLM-R with a tag polypeptide which provides an epitope to which an anti-tag antibody can selectively bind. The epitope tag is generally placed at the amino- or carboxyl-terminus of the GLM-R. The presence of such epitope-tagged forms of the GLM-R can be detected using an antibody against the tag polypeptide. Also, provision of the epitope tag enables the GLM-R to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.,* 8:2159-2165 (1988)]; the c-myc tag and the 8F9, 3C7, 6E10, G4, B7 and 9E10 antibodies thereto [Evan et al., *Molecular and Cellular Biology,* 5:3610-3616 (1985)]; and the Herpes Simplex virus glycoprotein D (gD) tag and its antibody [Paborsky et al., *Protein Engineering,* 3(6):547-553 (1990)]. Other tag polypeptides include the Flag-peptide [Hopp et al., *BioTechnology,* 6:1204-1210 (1988)]; the KT3 epitope peptide [Martin et al., *Science,* 255:192-194 (1992)]; an $\alpha$-tubulin epitope peptide [Skinner et al., *J. Biol. Chem.,* 266:15163-15166 (1991)]; and the T7 gene 10 protein peptide tag [Lutz-Freyermuth et al., *Proc. Natl. Acad. Sci. USA,* 87:6393-6397 (1990)].

In an alternative embodiment, the chimeric molecule may comprise a fusion of the GLM-R with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of a GLM-R polypeptide in place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130 issued Jun. 27, 1995.

D. Preparation of GLM-R

The description below relates primarily to production of GLM-R by culturing cells transformed or transfected with a vector containing GLM-R nucleic acid. It is, of course, contemplated that alternative methods, which are well known in the art, may be employed to prepare GLM-R. For instance, the GLM-R sequence, or portions thereof, may be produced by direct peptide synthesis using solid-phase techniques [see, e.g., Stewart et al., *Solid-Phase Peptide Synthesis*, W.H. Freeman Co., San Francisco, Calif. (1969); Merrifield, *J. Am. Chem. Soc.*, 85:2149-2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the GLM-R may be chemically synthesized separately and combined using chemical or enzymatic methods to produce the full-length GLM-R.

1. Isolation of DNA Encoding GLM-R

DNA encoding GLM-R may be obtained from a cDNA library prepared from tissue believed to possess the GLM-R mRNA and to express it at a detectable level. Accordingly, human GLM-R DNA can be conveniently obtained from a cDNA library prepared from human tissue, such as described in the Examples. The GLM-R-encoding gene may also be obtained from a genomic library or by known synthetic procedures (e.g., automated nucleic acid synthesis).

Libraries can be screened with probes (such as antibodies to the GLM-R or oligonucleotides of at least about 20-80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding GLM-R is to use PCR methodology [Sambrook et al., supra; Dieffenbach et al., *PCR Primer: A Laboratory Manual* (Cold Spring Harbor Laboratory Press, 1995)].

The Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined using methods known in the art and as described herein.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for GLM-R production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: A Practical Approach*, M. Butler, ed. (IRL Press, 1991) and Sambrook et al., supra.

Methods of eukaryotic cell transfection and prokaryotic cell transformation are known to the ordinarily skilled artisan, for example, $CaCl_2$, $CaPO_4$, liposome-mediated and electroporation. Depending on the host cell used, transformation is performed using standard techniques appropriate to such cells. The calcium treatment employing calcium chloride, as described in Sambrook et al., supra, or electroporation is generally used for prokaryotes. Infection with *Agrobacterium tumefaciens* is used for transformation of certain plant cells, as described by Shaw et al., *Gene*, 23:315 (1983) and WO 89/05859 published 29 Jun. 1989. For mammalian cells without such cell walls, the calcium phosphate precipitation method of Graham and van der Eb, *Virology*, 52:456-457 (1978) can be employed. General aspects of mammalian cell host system transfections have been described in U.S. Pat. No. 4,399,216. Transformations into yeast are typically carried out according to the method of Van Solingen et al., *J. Bact.*, 130:946 (1977) and Hsiao et al., *Proc. Natl. Acad. Sci.* (*USA*), 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology* 185:527-537 (1990) and Mansour et al., *Nature*, 336:348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). Other suitable prokaryotic host cells include Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as *Bacilli* such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC 55,244), which has the complete genotype tonA ptr3 phoA E15 (argF-lac)169 degP ompT kan$^r$; *E. coli* W3110 strain 37D6, which has the complete genotype tonA ptr3 phoA E15 (argF-lac)169 degP ompT rbs7 ilvG kan$^r$; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued 7 Aug. 1990. Alternatively, in vitro methods of cloning, e.g., PCR or other nucleic acid polymerase reactions, are suitable.

In addition to prokaryotes, eukaryotic microbes such as filamentous fungi or yeast are suitable cloning or expression hosts for GLM-R-encoding vectors. *Saccharomyces cerevisiae* is a commonly used lower eukaryotic host microorganism. Others include *Schizosaccharomyces pombe* (Beach and Nurse, *Nature* 290: 140 [1981]; EP 139,383 published 2 May 1985); *Kluyveromyces* hosts (U.S. Pat. No. 4,943,529; Fleer et al., *Bio/Technology*, 9:968-975 (1991)) such as, e.g., *K. lactis* (MW98-8C, CBS683, CBS4574; Louvencourt et al., *J. Bacteriol.*, 154(2):737-742 [1983]), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., *Bio/Technology*, 8:135 (1990)), *K. thermotolerans*, and *K. marxianus*; *yarrowia* (EP 402,226); *Pichia pastoris* (EP 183,070; Sreekrishna et al., *J. Basic Microbiol.*, 28:265-278 [1988]); *Candida*; *Trichoderma reesia* (EP 244,234); *Neurospora crassa* (Case et al., *Proc. Natl. Acad. Sci. USA*, 76:5259-5263 [1979]); *Schwanniomyces* such as *Schwanniomyces occidentalis* (EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al., *Biochem. Biophys. Res. Commun.*, 112:284-289 [1983]; Tilbum et al., *Gene*, 26:205-221 [1983]; Yelton et al., *Proc. Natl. Acad. Sci. USA*, 81: 1470-1474 [1984]) and *A. niger* (Kelly and Hynes, *EMBO J.*, 4:475-479 [1985]). Methylotropic yeasts are suitable herein and include, but are not limited to, yeast capable of growth on methanol selected from the genera consisting of *Hansenula, Candida, Kloeckera, Pichia, Saccharomyces, Torulopsis,* and *Rhodotorula*. A list of specific species that are exemplary of this class of yeasts may be found in C. Anthony, *The Biochemistry of Methylotrophs* 269 (1982).

Suitable host cells for the expression of glycosylated GLM-R are derived from multicellular organisms. Examples of invertebrate cells include insect cells such as *Drosophila* S2 and *Spodoptera* Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 (1977)); Chinese hamster ovary cells/-DHFR (CHO, Urlaub and Chasin, *Proc. Natl. Acad. Sci. USA*, 77:4216 (1980)); mouse sertoli cells (TM4, Mather, *Biol. Reprod.*, 23:243-251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

3. Selection and Use of a Replicable Vector

The nucleic acid (e.g., cDNA or genomic DNA) encoding GLM-R may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The GLM-R may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the GLM-R-encoding DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including *Saccharomyces* and *Kluyveromyces* α-factor leaders, the latter described in U.S. Pat. No. 5,010, 182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*.

An example of suitable selectable markers for mammalian cells are those that enable the identification of cells competent to take up the GLM-R-encoding nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA*, 77:4216 (1980). A suitable selection gene for use in yeast is the trp1 gene present in the yeast plasmid YRp7 [Stinchcomb et al., *Nature* 282:39 (1979); Kingsman et al., *Gene* 7:141 (1979); Tschemper et al., *Gene* 10:157 (1980)]. The trp1 gene provides a selection marker for a mutant strain of yeast lacking the ability to grow in tryptophan, for example, ATCC No. 44076 or PEP4-1 [Jones, *Genetics* 85:12 (1977)].

Expression and cloning vectors usually contain a promoter operably linked to the GLM-R-encoding nucleic acid sequence to direct mRNA synthesis. Promoters recognized by a variety of potential host cells are well known. Promoters suitable for use with prokaryotic hosts include the β-lactamase and lactose promoter systems [Chang et al., *Nature* 275:615 (1978); Goeddel et al., *Nature* 281:544 (1979)], alkaline phosphatase, a tryptophan (trp) promoter system [Goeddel, *Nucleic Acids Res.*, 8:4057 (1980); EP 36,776], and hybrid promoters such as the tac promoter [deBoer et al., *Proc. Natl. Acad. Sci. USA*, 80:21-25 (1983)]. Promoters for use in bacterial systems also will contain a Shine-Dalgarno (S.D.) sequence operably linked to the DNA encoding GLM-R.

Examples of suitable promoting sequences for use with yeast hosts include the promoters for 3-phosphoglycerate kinase [Hitzeman et al., *J. Biol. Chem.*, 255:2073 (1980)] or other glycolytic enzymes [Hess et al., *J. Adv. Enzyme Reg.*, 7:149 (1968); Holland, *Biochemistry* 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

GLM-R transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the GLM-R by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the GLM-R coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding GLM-R.

Still other methods, vectors, and host cells suitable for adaptation to the synthesis of GLM-R in recombinant vertebrate cell culture are described in Gething et al., *Nature* 293:620-625 (1981); Mantei et al., *Nature* 281:40-46 (1979); EP 117,060; and EP 117,058.

4. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA* 77:5201-5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence GLM-R polypeptide or against a synthetic peptide based on the DNA sequences provided herein or against exogenous sequence fused to GLM-R DNA and encoding a specific antibody epitope.

5. Purification of Polypeptide

Forms of GLM-R may be recovered from culture medium or from host cell lysates. If membrane-bound, it can be released from the membrane using a suitable detergent solution (e.g. Triton-X® 100) or by enzymatic cleavage. Cells employed in expression of GLM-R can be disrupted by various physical or chemical means, such as freeze-thaw cycling, sonication, mechanical disruption, or cell lysing agents.

It may be desired to purify GLM-R from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the GLM-R. Various methods of protein purification may be employed and such methods are known in the art and described for example in Deutscher, *Methods in Enzymology* 182 (1990); Scopes, *Protein Purification: Principles and Practice*, Springer-Verlag, New York (1982). The purification step(s) selected will depend, for example, on the nature of the production process used and the particular GLM-R produced.

E. Uses for GLM-R

Nucleotide sequences (or their complement) encoding GLM-R have various applications in the art of molecular biology, including uses as hybridization probes, in chromosome and gene mapping and in the generation of anti-sense RNA and DNA. GLM-R nucleic acid will also be useful for the preparation of GLM-R polypeptides by the recombinant techniques described herein.

The full-length native sequence GLM-R DNA (SEQ ID NO:1), or portions thereof, may be used as hybridization probes for a cDNA library to isolate the full-length GLM-R cDNA or to isolate still other cDNAs (for instance, those encoding naturally-occurring variants of GLM-R or GLM-R from other species) which have a desired sequence identity to the GLM-R sequence disclosed in FIG. 1 (SEQ ID NO:1). Optionally, the length of the probes will be about 20 to about 50 bases. The hybridization probes may be derived from at least partially novel regions of the nucleotide sequence of SEQ ID NO:1 wherein such regions may be determined without undue experimentation or from genomic sequences including promoters, enhancer elements and introns of native sequence GLM-R. By way of example, a screening method may comprise isolating the coding region of the GLM-R gene using the known DNA sequence to synthesize a selected probe of about 40 bases. Hybridization probes may be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of the GLM-R gene of the present invention can be used to screen libraries of human cDNA, genomic DNA or mRNA to determine which members of such libraries the probe hybridizes to. Hybridization techniques are described in further detail in the Examples below.

Any EST sequences disclosed in the present application may similarly be employed as probes, using the methods disclosed herein.

Other useful fragments of the GLM-R nucleic acids include antisense or sense oligonucleotides comprising a singe-stranded nucleic acid sequence (either RNA or DNA) capable of binding to target GLM-R mRNA (sense) or GLM-R DNA (antisense) sequences. Antisense or sense oligonucleotides, according to the present invention, comprise a fragment of the coding region of GLM-R DNA. Such a fragment generally comprises at least about 14 nucleotides, preferably from about 14 to 30 nucleotides. The ability to derive an antisense or a sense oligonucleotide, based upon a cDNA sequence encoding a given protein is described in, for example, Stein and Cohen, *Cancer Res.* 48:2659 (1988) and van der Krol et al., *BioTechniques* 6:958 (1988).

Binding of antisense or sense oligonucleotides to target nucleic acid sequences results in the formation of duplexes that block transcription or translation of the target sequence by one of several means, including enhanced degradation of the duplexes, premature termination of transcription or translation, or by other means. The antisense oligonucleotides thus may be used to block expression of GLM-R proteins. Antisense or sense oligonucleotides further comprise oligonucleotides having modified sugar-phosphodiester backbones (or other sugar linkages, such as those described in WO 91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences.

Other examples of sense or antisense oligonucleotides include those oligonucleotides which are covalently linked to organic moieties, such as those described in WO 90/10048, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, $CaPO_4$-mediated DNA transfection, electroporation, or by using gene transfer vectors such as Epstein-Barr virus. In a preferred procedure, an antisense or sense oligonucleotide is inserted into a suitable retroviral vector. A cell containing the target nucleic acid sequence is contacted with the recombinant retroviral vector, either in vivo or ex vivo. Suitable retroviral vectors include, but are not limited to, those derived from the murine retrovirus M-MuLV, N2 (a retrovirus derived from M-MuLV), or the double copy vectors designated DCT5A, DCT5B and DCT5C (see WO 90/13641).

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

The probes may also be employed in PCR techniques to generate a pool of sequences for identification of closely related GLM-R coding sequences.

Nucleotide sequences encoding a GLM-R can also be used to construct hybridization probes for mapping the gene which encodes that GLM-R and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

When the coding sequences for GLM-R encode a protein which binds to another protein (for example, where the GLM-R is a receptor or co-ligand), the GLM-R can be used in assays to identify the other proteins or molecules involved in the binding interaction. By such methods, inhibitors of the receptor/ligand binding interaction can be identified. Proteins involved in such binding interactions can also be used to screen for peptide or small molecule inhibitors or agonists of the binding interaction. Also, the receptor GLM-R can be used to isolate correlative ligand(s). Screening assays can be designed to find lead compounds that mimic the biological activity of a native GLM-R or a receptor for GLM-R. Such screening assays will include assays amenable to high-throughput screening of chemical libraries, making them particularly suitable for identifying small molecule drug candidates. Small molecules contemplated include synthetic organic or inorganic compounds. The assays can be performed in a variety of formats, including protein-protein binding assays, biochemical screening assays, immunoassays and cell based assays, which are well characterized in the art.

Nucleic acids which encode GLM-R or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding GLM-R can be used to clone genomic DNA encoding GLM-R in accordance with established techniques and the genomic sequences used to generate transgenic animals that contain cells which express DNA encoding GLM-R. Methods for generating transgenic animals, particularly animals such as mice or rats, have become conventional in the art and are described, for example, in U.S. Pat. Nos. 4,736,866 and 4,870,009. Typically, particular cells would be targeted for GLM-R transgene incorporation with tissue-specific enhancers. Transgenic animals that include a copy of a transgene encoding GLM-R introduced into the germ line of the animal at an embryonic stage can be used to examine the effect of increased expression of DNA encoding GLM-R. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of GLM-R can be used to construct a GLM-R "knock out" animal which has a defective or altered DNA encoding GLM-R as a result of homologous recombination between the endogenous DNA encoding GLM-R and altered genomic DNA encoding GLM-R introduced into an embryonic stem cell of the animal. For example, cDNA encoding GLM-R can be used to clone genomic DNA encoding GLM-R in accordance with established techniques. A portion of the genomic DNA encoding GLM-R can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, *Cell* 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell* 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach*, E. J. Robertson, ed. (IRL, Oxford, 1987), pp. 113-152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the GLM-R polypeptide.

Nucleic acid encoding the GLM-R polypeptides may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., *Proc. Natl. Acad. Sci. USA* 83:4143-4146 [1986]). The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., *Trends in Biotechnology* 11 205-210 [1993]). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., *J. Biol. Chem.* 262 4429-4432 (1987); and Wagner et al., *Proc. Natl. Acad. Sci. USA* 87: 3410-3414 (1990). For review of gene marking and gene therapy protocols see Anderson et al., *Science* 256: 808-813 (1992).

The GLM-R polypeptides described herein may also be employed as molecular weight markers for protein electrophoresis purposes.

The nucleic acid molecules encoding the GLM-R polypeptides or fragments thereof described herein are useful for chromosome identification. In this regard, there exists an ongoing need to identify new chromosome markers, since relatively few chromosome marking reagents, based upon actual sequence data are presently available. Each GLM-R nucleic acid molecule of the present invention can be used as a chromosome marker.

The GLM-R polypeptides and nucleic acid molecules of the present invention may also be used for tissue typing, wherein the GLM-R polypeptides of the present invention may be differentially expressed in one tissue as compared to another. GLM-R nucleic acid molecules will find use for generating probes for PCR, Northern analysis, Southern analysis and Western analysis.

The GLM-R polypeptides and modulators thereof described herein may also be employed as therapeutic agents. The GLM-R polypeptides and modulators thereof of the present invention can be formulated according to known methods to prepare pharmaceutically useful compositions, whereby the GLM-R product hereof is combined in admixture with a pharmaceutically acceptable carrier vehicle. Therapeutic formulations are prepared for storage by mixing the active ingredient having the desired degree of purity with optional physiologically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as TWEEN®, PLURONICS® or PEG.

The formulations to be used for in vivo administration must be sterile. This is readily accomplished by filtration through sterile filtration membranes, prior to or following lyophilization and reconstitution.

Therapeutic compositions herein generally are placed into a container having a sterile access port, for example, an intravenous solution bag or vial having a stopper pierceable by a hypodermic injection needle.

The route of administration is in accord with known methods, e.g. injection or infusion by intravenous, intraperitoneal, intracerebral, intramuscular, intraocular, intraarterial or intralesional routes, topical administration, or by sustained release systems.

Dosages and desired drug concentrations of pharmaceutical compositions of the present invention may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" In *Toxicokinetics and New Drug Development*, Yacobi et al., Eds., Pergamon Press, New York 1989, pp. 42-96.

When in vivo administration of a GLM-R polypeptide or agonist or antagonist thereof is employed, normal dosage amounts may vary from about 10 ng/kg to up to 100 mg/kg of mammal body weight or more per day, preferably about 1 µg/kg/day to 10 mg/kg/day, depending upon the route of administration. Guidance as to particular dosages and methods of delivery is provided in the literature; see, for example, U.S. Pat. Nos. 4,657,760; 5,206,344; or 5,225,212. It is anticipated that different formulations will be effective for different treatment compounds and different disorders, that administration targeting one organ or tissue, for example, may necessitate delivery in a manner different from that to another organ or tissue.

Where sustained-release administration of a GLM-R polypeptide or modulator is desired in a formulation with release characteristics suitable for the treatment of any disease or disorder requiring administration of the GLM-R polypeptide or modulator, microencapsulation is contemplated. Microencapsulation of recombinant proteins for sustained release has been successfully performed with human growth hormone (rhGH), interferon- (rhIFN-), interleukin-2, and MN rgp120. Johnson et al., *Nat. Med.* 2:795-799 (1996); Yasuda, *Biomed. Ther.* 27:1221-1223 (1993); Hora et al., *Bio/Technology* 8:755-758 (1990); Cleland, "Design and Production of Single Immunization Vaccines Using Poly-lactide Polyglycolide Microsphere Systems," in *Vaccine Design: The Subunit and Adjuvant Approach*, Powell and Newman, eds, (Plenum Press: New York, 1995), pp. 439-462; WO 97/03692, WO 96/40072, WO 96/07399; and U.S. Pat. No. 5,654,010.

The sustained-release formulations of these proteins can be developed using poly-lactic-coglycolic acid (PLGA) polymer due to its biocompatibility and wide range of biodegradable properties. The degradation products of PLGA, lactic and glycolic acids, can be cleared quickly within the human body. Moreover, the degradability of this polymer can be adjusted from months to years depending on its molecular weight and composition. Lewis, "Controlled release of bioactive agents from lactide/glycolide polymer," in: M. Chasin and R. Langer (Eds.), *Biodegradable Polymers as Drug Delivery Systems* (Marcel Dekker: New York, 1990), pp. 1-41.

GLM-R and compositions comprising GLM-R are preferably used in vivo. However, as discussed below, administration can be in vitro such as in the methods described below for screening for modulators of GLM-R. Although, it is understood that modulators of GLM-R can also be identified by the use of animal models and samples from patients.

This invention encompasses methods of screening compounds to identify those that mimic or enhance the GLM-R polypeptide (agonists) or prevent or inhibit the effect of the GLM-R polypeptide (antagonists). Agonists and antagonists are referred to as modulators herein. Screening assays for antagonist drug candidates are designed to identify compounds that bind or complex with the GLM-R polypeptides encoded by the genes identified herein, or otherwise interfere with the interaction of the encoded polypeptides with other cellular proteins. Such screening assays will include assays amenable to high-throughput screening of chemical libraries, making them particularly suitable for identifying small molecule drug candidates.

The assays can be performed in a variety of formats, including protein-protein binding assays, biochemical screening assays, immunoassays, and cell-based assays, which are well characterized in the art.

All assays for antagonists are common in that they call for contacting the drug candidate with a GLM-R polypeptide encoded by a nucleic acid identified herein under conditions and for a time sufficient to allow these two components to interact.

In binding assays, the interaction is binding and the complex formed can be isolated or detected in the reaction mixture. In a particular embodiment, the GLM-R polypeptide encoded by the gene identified herein or the drug candidate is immobilized on a solid phase, e.g., on a microtiter plate, by covalent or non-covalent attachments. Non-covalent attachment generally is accomplished by coating the solid surface with a solution of the GLM-R polypeptide and drying. Alternatively, an immobilized antibody, e.g., a monoclonal antibody, specific for the GLM-R polypeptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with but does not bind to a particular GLM-R polypeptide encoded by a gene identified herein, its interaction with that polypeptide can be assayed by methods well known for detecting protein-protein interactions. Such assays include traditional approaches, such as, e.g., cross-linking, co-immunoprecipitation, and co-purification through gradients or chromatographic columns. In addition, protein-protein interactions can be monitored by using a yeast-based genetic system described by Fields and co-workers (Fields and Song, *Nature (London)* 340:245-246 (1989); Chien et al., *Proc. Natl. Acad. Sci. USA* 88:9578-9582 (1991)) as disclosed by Chevray and Nathans, *Proc. Natl. Acad. Sci. USA* 89: 5789-5793 (1991). Many transcriptional activators, such as yeast GAL4, consist of two physically discrete modular domains, one acting as the DNA-binding domain, the other one functioning as the transcription-activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

Compounds that interfere with the interaction of a DNA encoding a GLM-R polypeptide identified herein and other intra- or extracellular components can be tested as follows: usually a reaction mixture is prepared containing the GLM-R polypeptide and the intra- or extracellular component under conditions and for a time allowing for the interaction and binding of the two products. To test the ability of a candidate compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described hereinabove. The formation of a complex in the control reaction(s) but not in the reaction mixture containing the test compound indicates that the test compound interferes with the interaction of the test compound and its reaction partner.

To assay for antagonists, the GLM-R polypeptide may be added to a cell along with the compound to be screened for a particular activity and the ability of the compound to inhibit the activity of interest in the presence of the GLM-R polypeptide indicates that the compound is an antagonist to the GLM-R polypeptide. Alternatively, antagonists may be detected by combining the GLM-R polypeptide and a potential antagonist with membrane-bound GLM-R polypeptide receptors or recombinant receptors under appropriate conditions for a competitive inhibition assay. The GLM-R polypeptide can be labeled, such as by radioactivity, such that the number of GLM-R polypeptide molecules bound to the receptor can be used to determine the effectiveness of the potential antagonist. The gene encoding the receptor can be identified by numerous methods known to those of skill in the art, for example, ligand panning and FACS sorting. Coligan et al., *Current Protocols in Immun.* 1(2): Chapter 5 (1991). Preferably, expression cloning is employed wherein polyadenylated RNA is prepared from a cell responsive to the GLM-R polypeptide and a cDNA library created from this RNA is divided into pools and used to transfect COS cells or other cells that are not responsive to the GLM-R polypeptide. Transfected cells that are grown on glass slides are exposed to labeled GLM-R polypeptide. The GLM-R polypeptide can be labeled by a variety of means including iodination or inclusion of a recognition site for a site-specific protein kinase. Following fixation and incubation, the slides are subjected to autoradiographic analysis. Positive pools are identified and sub-pools are prepared and re-transfected using an interactive sub-pooling and re-screening process, eventually yielding a single clone that encodes the putative receptor.

As an alternative approach for receptor identification, labeled GLM-R polypeptide can be photoaffinity-linked with cell membrane or extract preparations that express the receptor molecule. Cross-linked material is resolved by PAGE and exposed to X-ray film. The labeled complex containing the receptor can be excised, resolved into peptide fragments, and subjected to protein micro-sequencing. The amino acid sequence obtained from micro-sequencing would be used to design a set of degenerate oligonucleotide probes to screen a cDNA library to identify the gene encoding the putative receptor.

In another assay for antagonists, mammalian cells or a membrane preparation expressing the receptor would be incubated with labeled GLM-R polypeptide in the presence of the candidate compound. The ability of the compound to enhance or block this interaction could then be measured.

More specific examples of potential antagonists include an oligonucleotide that binds to the fusions of immunoglobulin with GLM-R polypeptide, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. Alternatively, a potential antagonist may be a closely related protein, for example, a mutated form of the GLM-R polypeptide that recognizes the receptor but imparts no effect, thereby competitively inhibiting the action of the GLM-R polypeptide.

In one embodiment herein where competitive binding assays are performed, GLM-R receptor or an antibody to GLM-R may be used as a competitor.

Another potential GLM-R polypeptide antagonist is an antisense RNA or DNA construct prepared using antisense technology, where, e.g., an antisense RNA or DNA molecule acts to block directly the translation of mRNA by hybridizing to targeted mRNA and preventing protein translation. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature GLM-R polypeptides herein, is used to design an antisense RNA oligonucleotide of from about 10 to 40 base pairs in length. A DNA oligonucleotide is designed to be complementary to a region of the gene involved in transcription (triple helix—see Lee et al., *Nucl. Acids Res.* 6:3073 (1979);

Cooney et al., *Science* 241: 456 (1988); Dervan et al., *Science* 251:1360 (1991)), thereby preventing transcription and the production of the GLM-R polypeptide. The antisense RNA oligonucleotide hybridizes to the mRNA in vivo and blocks translation of the mRNA molecule into the GLM-R polypeptide (antisense—Okano, *Neurochem.* 56:560 (1991); *Oligodeoxynucleotides as Antisense Inhibitors of Gene Expression* (CRC Press: Boca Raton, Fla., 1988). The oligonucleotides described above can also be delivered to cells such that the antisense RNA or DNA may be expressed in vivo to inhibit production of the GLM-R polypeptide. When antisense DNA is used, oligodeoxyribonucleotides derived from the translation-initiation site, e.g., between about −10 and +10 positions of the target gene nucleotide sequence, are preferred.

Potential antagonists include small molecules that bind to the active site, the receptor binding site, or growth factor or other relevant binding site of the GLM-R polypeptide, thereby blocking the normal biological activity of the GLM-R polypeptide. Examples of small molecules include, but are not limited to, small peptides or peptide-like molecules, preferably soluble peptides, and synthetic non-peptidyl organic or inorganic compounds.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g., Rossi, *Current Biology* 4:469-471 (1994), and PCT publication No. WO 97/33551 (published Sep. 18, 1997).

Nucleic acid molecules in triple-helix formation used to inhibit transcription should be single-stranded and composed of deoxynucleotides. The base composition of these oligonucleotides is designed such that it promotes triple-helix formation via Hoogsteen base-pairing rules, which generally require sizeable stretches of purines or pyrimidines on one strand of a duplex. For further details see, e.g., PCT publication No. WO 97/33551, supra.

These small molecules can be identified by any one or more of the screening assays discussed hereinabove and/or by any other screening techniques well known for those skilled in the art.

It is appreciated that all the assays provided herein can be used to screen a wide variety of candidate bioactive agents. The term "candidate bioactive agent", "candidate agent" or "drug candidate" or grammatical equivalents as used herein describes any molecule, e.g., protein, oligopeptide, small organic molecule, polysaccharide, polynucleotide, purine analog, etc., to be tested for bioactive agents that are capable of directly or indirectly altering either the cellular activity phenotype or the expression of a GLM-R sequence, including both nucleic acid sequences and protein sequences.

Candidate agents can encompass numerous chemical classes, though typically they are organic molecules, preferably small organic compounds having a molecular weight of more than 100 and less than about 2,500 daltons (d). Small molecules are further defined herein as having a molecular weight of between 50 d and 2000 d. In another embodiment, small molecules have a molecular weight of less than 1500, or less than 1200, or less than 1000, or less than 750, or less than 500 d. In one embodiment, a small molecule as used herein has a molecular weight of about 100 to 200 d. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Particularly preferred are peptides.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In a preferred embodiment, the candidate bioactive agents are proteins. By "protein" herein is meant at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and norleucine are considered amino acids for the purposes of the invention. "Amino acid" also includes amino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations.

In a preferred embodiment, the candidate bioactive agents are naturally occurring proteins or fragments of naturally occurring proteins. Thus, for example, cellular extracts containing proteins, or random or directed digests of proteinaceous cellular extracts, may be used. In this way libraries of procaryotic and eucaryotic proteins may be made for screening in the methods of the invention. Particularly preferred in this embodiment are libraries of bacterial, fungal, viral, and mammalian proteins, with the latter being preferred, and human proteins being especially preferred.

In a preferred embodiment, the candidate bioactive agents are peptides of from about 5 to about 30 amino acids, with from about 5 to about 20 amino acids being preferred, and from about 7 to about 15 being particularly preferred. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of nucleic acid binding domains, the creation of cysteines, for cross-linking, prolines for SH-3 domains, serines, threonines, tyrosines or histidines for phosphorylation sites, etc., or to purines, etc.

In a preferred embodiment, the candidate bioactive agents are nucleic acids. By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage et al., *Tetrahedron* 49(10):1925 (1993) and references therein; Letsinger, *J. Org. Chem.* 35:3800 (1970); Sprinzl et al., *Eur. J. Biochem.* 81:579 (1977); Letsinger et al., *Nucl. Acids Res.* 14:3487 (1986); Sawai et al., *Chem. Lett.* 805 (1984); Letsinger et al., *J. Am. Chem. Soc.* 110:4470 (1988); and Pauwels et al., *Chemica Scripta* 26:141 (1986)), phosphorothioate (Mag et al., *Nucleic Acids Res.* 19:1437 (1991); and U.S. Pat. No. 5,644,048), phosphorodithioate (Briu et al., *J. Am. Chem. Soc.* 111:2321 (1989), O-methylphophoroamidite linkages (see Eckstein, *Oligonucleotides and Analogues: A Practical Approach*, Oxford University Press), and peptide nucleic acid backbones and linkages (see Egholm, *J. Am. Chem. Soc.* 114:1895 (1992); Meier et al., *Chem. Int. Ed. Engl.* 31:1008 (1992); Nielsen, *Nature* 365: 566 (1993); Carlsson et al., *Nature* 380:207 (1996), all of which are incorporated by reference). Other analog nucleic acids include those with positive backbones (Denpcy et al., *Proc. Natl. Acad. Sci. USA* 92:6097 (1995); non-ionic backbones (U.S. Pat. Nos. 5,386,023, 5,637,684, 5,602,240, 5,216,141 and 4,469,863; Kiedrowshi et al., *Angew. Chem. Intl.* (Ed. English) 30:423 (1991); Letsinger et al., *J. Am. Chem. Soc.* 110:4470 (1988); Letsinger et al., *Nucleoside & Nucleotide* 13:1597 (1994); Chapters 2 and 3, ASC Symposium Series 580, "Carbohydrate Modifications in Antisense Research", Ed. Y. S. Sanghui and P. Dan Cook; Mesmaeker et al., *Bioorganic & Medicinal Chem. Lett.* 4:395 (1994); Jeffs et al., *J. Biomolecular NMR* 34:17 (1994); *Tetrahedron Lett.* 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., *Chem. Soc. Rev.* (1995) pp 169-176). Several nucleic acid analogs are described in Rawls, C & E News Jun. 2, 1997 page 35. All of these references are hereby expressly incorporated by reference. These modifications of the ribose-phosphate backbone may be done to facilitate the addition of additional moieties such as labels, or to increase the stability and half-life of such molecules in physiological environments. In addition, mixtures of naturally occurring nucleic acids and analogs can be made. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

As described above generally for proteins, nucleic acid candidate bioactive agents may be naturally occurring nucleic acids, random nucleic acids, or "biased" random nucleic acids. For example, digests of prokaryotic or eukaryotic genomes may be used as is outlined above for proteins.

In a preferred embodiment, the candidate bioactive agents are organic chemical moieties, a wide variety of which are available in the literature.

In a preferred embodiment, as outlined above, screens may be done on individual genes and gene products (proteins). In a preferred embodiment, the gene or protein has been identified as described below in the Examples as a differentially expressed gene associated with particular tissues and thus conditions related to those tissues. Thus, in one embodiment, screens are designed to first find candidate agents that can bind to GLM-R, and then these agents may be used in assays that evaluate the ability of the candidate agent to modulate GLM-R activity. Thus, as will be appreciated by those in the art, there are a number of different assays which may be run.

Screening for agents that modulate the activity of GLM-R may also be done. In a preferred embodiment, methods for screening for a bioactive agent capable of modulating the activity of GLM-R comprise the steps of adding a candidate bioactive agent to a sample of GLM-R and determining an alteration in the biological activity of GLM-R. "Modulating the activity of GLM-R" includes an increase in activity, a decrease in activity, or a change in the type or kind of activity present. Thus, in this embodiment, the candidate agent should both bind to GLM-R (although this may not be necessary), and alter its biological or biochemical activity as defined herein. The methods include both in vitro screening methods, as are generally outlined above, and in vivo screening of cells for alterations in the presence, expression, distribution, activity or amount of GLM-R.

Thus, in this embodiment, the methods comprise combining a sample and a candidate bioactive agent, and evaluating the effect on GLM-R activity. By "GLM-R protein activity" or grammatical equivalents herein is meant at least one of the GLM-R protein's biological activities as described above.

In a preferred embodiment, the activity of the GLM-R protein is increased; in another preferred embodiment, the activity of the GLM-R protein is decreased. Thus, bioactive agents that are antagonists are preferred in some embodiments, and bioactive agents that are agonists may be preferred in other embodiments.

In one aspect of the invention, cells containing GLM-R sequences are used in drug screening assays by evaluating the effect of drug candidates on GLM-R. Cell types include normal cells, tumor cells, and adipocytes.

Methods of assessing GLM-R activity such as changes in glucose uptake, leptin release, metabolism, triglyceride and free fatty acid levels, body weight and body fat, are known in the art and are exemplified below in the examples.

In a preferred embodiment, the methods comprise adding a candidate bioactive agent, as defined above, to a cell comprising GLM-R. Preferred cell types include almost any cell. The cells contain a nucleic acid, preferably recombinant, that encodes a GLM-R protein. In a preferred embodiment, a library of candidate agents are tested on a plurality of cells.

In one aspect, the assays are evaluated in the presence or absence or previous or subsequent exposure to physiological signals, for example hormones, antibodies, peptides, antigens, cytokines, growth factors, action potentials, pharmacological agents including chemotherapeutics, radiation, carcinogenics, or other cells (i.e., cell-cell contacts). In another example, the determinations are determined at different stages of the cell cycle process.

The GLM-R sequences provided herein can also be used in methods of diagnosis. Overexpression of GLM-R may indicate an abnormally high metabolic rate and underexpression may indicate a propensity for obesity and related disorders. Moreover, a sample from a patient may be analyzed for mutated or dysfunctional GLM-R. Generally, such methods include comparing a sample from a patient and comparing GLM-R expression to that of a control.

A potential use of a GLM-R would be in the regulation of the development or function of monocytes or macrophage and the treatment of disorders related thereto.

F. Anti-GLM-R Antibodies

The present invention further provides anti-GLM-R antibodies. Exemplary antibodies include polyclonal, monoclonal, humanized, bispecific, and heteroconjugate antibodies.

1. Polyclonal Antibodies

The anti-GLM-R antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the GLM-R polypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

2. Monoclonal Antibodies

The anti-GLM-R antibodies may, alternatively, be monoclonal antibodies. Monoclonal antibodies may be prepared using hybridoma methods, such as those described by Kohler and Milstein, *Nature* 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the GLM-R polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59-103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies [Kozbor, *J. Immunol.*, 133:3001 (1984); Brodeur et al., *Monoclonal Antibody Production Techniques and Applications*, Marcel Dekker, Inc., New York, (1987) pp. 51-63].

The culture medium in which the hybridoma cells are cultured can then be assayed for the presence of monoclonal antibodies directed against GLM-R. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

3. Human and Humanized Antibodies

The anti-GLM-R antibodies of the invention may further comprise humanized antibodies or human antibodies. Humanized forms of non-human (e.g. murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature* 321:522-525 (1986); Riechmann et al., *Nature,* 332:323-329 (1988); and Presta, *Curr. Op. Struct. Biol.,* 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature,* 321:522-525 (1986); Riechmann et al., *Nature,* 332:323-327 (1988); Verhoeyen et al., *Science,* 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, *J. Mol. Biol.,* 227:381 (1991); Marks et al., *J. Mol. Biol.,* 222:581 (1991)]. The techniques of Cole et al. and Boerner et al. are also available for the preparation of human monoclonal antibodies (Cole et al., *Monoclonal Antibodies and Cancer Therapy*, Alan R. Liss, p. 77 (1985) and Boerner et al., *J. Immunol.,* 147(1):86-95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology* 10, 779-783 (1992); Lonberg et al., *Nature* 368 856-859 (1994); Morrison, *Nature* 368, 812-13 (1994); Fishwild et al., *Nature Biotechnology* 14, 845-51 (1996); Neuberger, *Nature Biotechnology* 14, 826 (1996); Lonberg and Huszar, *Intern. Rev. Immunol.* 13 65-93 (1995).

4. Bispecific Antibodies

Bispecific antibodies are monoclonal, preferably human or humanized, antibodies that have binding specificities for at least two different antigens. In the present case, one of the binding specificities is for the GLM-R, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, *Nature,* 305:537-539 (1983)]. Because of the random assortment of immunoglobulin heavy and light chains, these hybridomas (quadromas) produce a potential mixture often different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., *EMBO J.,* 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology,* 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. F(ab')$_2$ bispecific antibodies). Techniques for generating bispecific antibodies from antibody fragments have been described in the literature. For example, bispecific antibodies can be prepared can be prepared using chemical linkage. Brennan et al., *Science* 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Fab' fragments may be directly recovered from *E. coli* and chemically coupled to form bispecific antibodies. Shalaby et al., *J. Exp. Med.* 175:217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.* 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., *J. Immunol.* 152:5368 (1994).

Antibodies with more than two valencies are contemplated. For example, trispecific antibodies can be prepared. Tutt et al., *J. Immunol.* 147:60 (1991). Exemplary bispecific antibodies may bind to two different epitopes on a given GLM-R polypeptide herein. Alternatively, an anti-GLM-R polypeptide arm may be combined with an arm which binds to a triggering molecule on a leukocyte such as a T-cell receptor molecule (e.g., CD2, CD3, CD28, or B7), or Fc receptors for IgG (FcγR), such as FcγRI (CD64), FcγRII (CD32) and FcγRIII (CD16) so as to focus cellular defense mechanisms to the cell expressing the particular GLM-R polypeptide. Bispecific antibodies may also be used to localize cytotoxic agents to cells which express a particular GLM-R polypeptide. These antibodies possess a GLM-R-binding arm and an arm which binds a cytotoxic agent or a radionuclide chelator, such as EOTUBE, DPTA, DOTA, or TETA. Another bispecific antibody of interest binds the GLM-R polypeptide and further binds tissue factor (TF).

5. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

6. Effector Function Engineering

It may be desirable to modify the antibody of the invention with respect to effector function, so as to enhance, e.g., the effectiveness of the antibody in treating cancer. For example, cysteine residue(s) may be introduced into the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.*, 176: 1191-1195 (1992) and Shopes, *J. Immunol.*, 148: 2918-2922 (1992). Homodimeric antibodies with enhanced anti-tumor activity may also be prepared using heterobifunctional cross-linkers as described in Wolff et al., *Cancer Research*, 53: 2560-2565 (1993). Alternatively, an antibody can be engineered that has dual Fc regions and may thereby have enhanced complement lysis and ADCC capabilities. See Stevenson et al., *Anti-Cancer Drug Design*, 3: 219-230 (1989).

7. Immunoconjugates

The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science,* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody may be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g., avidin) that is conjugated to a cytotoxic agent (e.g., a radionucleotide).

8. Immunoliposomes

The antibodies disclosed herein may also be formulated as immunoliposomes. Liposomes containing the antibody are prepared by methods known in the art, such as described in Epstein et al., *Proc. Natl. Acad. Sci. USA* 82: 3688 (1985); Hwang et al., *Proc. Natl. Acad. Sci. USA* 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.* 257: 286-288 (1982) via a disulfide-interchange reaction. A chemotherapeutic agent (such as Doxorubicin) is optionally contained within the liposome. See Gabizon et al., *J. National Cancer Inst.* 81 (19): 1484 (1989).

9. Pharmaceutical Compositions of Antibodies

Antibodies specifically binding a GLM-R polypeptide identified herein, as well as other molecules identified by the screening assays disclosed hereinbefore, can be administered for the treatment of various disorders in the form of pharmaceutical compositions.

If the GLM-R polypeptide is intracellular and whole antibodies are used as inhibitors, internalizing antibodies are preferred. However, lipofections or liposomes can also be used to deliver the antibody, or an antibody fragment, into cells. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., *Proc. Natl. Acad. Sci. USA,* 90: 7889-7893 (1993). The formulation herein may also contain more than one active compound as necessary for the particular indication being treated, preferably those with complementary activities that do not adversely affect each other. Alternatively, or in addition, the composition may comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles, and nanocapsules) or in macroemulsions. Such techniques are disclosed in *Remington's Pharmaceutical Sciences,* supra.

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

G. Generalized Uses for Anti-GLM-R Antibodies

The anti-GLM-R antibodies of the invention have various utilities. For example, anti-GLM-R antibodies may be used in diagnostic assays for GLM-R, e.g., detecting its expression in specific cells, tissues, or serum. Various diagnostic assay techniques known in the art may be used, such as competitive binding assays, direct or indirect sandwich assays and immunoprecipitation assays conducted in either heterogeneous or homogeneous phases [Zola, *Monoclonal Antibodies: A Manual of Techniques,* CRC Press, Inc. (1987) pp. 147-158]. The antibodies used in the diagnostic assays can be labeled with a detectable moiety. The detectable moiety should be capable of producing, either directly or indirectly, a detectable signal. For example, the detectable moiety may be a radioisotope, such as $^3$H, $^{14}$C, $^{32}$P, $^{35}$S, or $^{125}$I, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature*, 144:945 (1962); David et al., *Biochemistry*, 13:1014 (1974); Pain et al., *J. Immunol. Meth.*, 40:219 (1981); and Nygren, *J. Histochem. Cytochem.*, 30:407 (1982).

Anti-GLM-R antibodies also are useful for the affinity purification of GLM-R from recombinant cell culture or natural sources. In this process, the antibodies against GLM-R are immobilized on a suitable support, such a Sephadex resin or filter paper, using methods well known in the art. The immobilized antibody then is contacted with a sample containing the GLM-R to be purified, and thereafter the support is washed with a suitable solvent that will remove substantially all the material in the sample except the GLM-R, which is bound to the immobilized antibody. Finally, the support is washed with another suitable solvent that will release the GLM-R from the antibody.

The following examples are offered for illustrative purposes only, and are not intended to limit the scope of the present invention in any way.

H. Transgenic Animals

Nucleic acids which encode novel human GLM-R or analogous GLM-R from other species, such as the murine, can be used to generate either transgenic animals or "knock out" animals which, in turn, are useful in the development and screening of therapeutically useful reagents. A transgenic animal (e.g., a mouse) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, murine cDNA encoding or an appropriate sequence thereof can be used to clone genomic DNA encoding in accordance with established techniques and the genomic sequences used to generate transgenic animals that contain cells which express DNA encoding GLM-R. Methods for generating transgenic animals, particularly animals such as mice, have become conventional in the art and are described, for example, in U.S. Pat. Nos. 4,736,866 and 4,870,009. Typically, particular cells would be targeted for transgene incorporation with tissue-specific enhancers, which could result in production of GLM-R. Transgenic animals that include a copy of a transgene encoding introduced into the germ line of the animal at an embryonic stage can be used to examine the effect of increased expression of DNA encoding. Such animals can be used as tester animals for reagents thought to confer protection from weight related disorders, such as, obesity, cachexia or anorexia. In accordance with this facet of the invention, an animal is treated with the reagent and a reduced incidence of the disease, compared to untreated animals bearing the transgene, would indicate a potential therapeutic intervention for the disease.

Alternatively, the non-human homologues of GLM-R can be used to construct a "knock out" animal which has a defective or altered gene encoding GLM-R as a result of homologous recombination between the endogenous gene encoding and altered genomic DNA encoding introduced into an embryonic cell of the animal. For example, murine cDNA encoding GLM-R can be used to clone genomic DNA encoding in accordance with established techniques. A portion of the genomic DNA encoding (e.g., such as an exon) GLM-R can be deleted or replaced with another gene, such as a gene encoding a selectable marker which can be used to monitor integration. Typically, several kilobases of unaltered flanking DNA (both at the 5' and 3' ends) are included in the vector (see e.g., Thomas and Capecchi, *Cell*, 51:503 (1987) for a description of homologous recombination vectors). The vector is introduced into an embryonic stem cell line (e.g., by electroporation) and cells in which the introduced DNA has homologously recombined with the endogenous DNA are selected (see e.g., Li et al., *Cell*, 69: 915 [1992]). The selected cells are then injected into a blastocyst of an animal (e.g., a mouse) to form aggregation chimeras (see e.g., Bradley, in *Teratocarcinomas and Embryonic Stem Cells: A Practical Approach*, E. J. Robertson, ed. [IRL, Oxford, 1987], pp. 113-152). A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for their ability to accept grafts, reject tumors and defend against infectious diseases and can be used in the study of basic immunobiology.

One particular technique used for the creation of transgenic animals involves the use of yeast artificial chromosomes (YAC). Yeast artificial chromosomes are cloning vectors constructed from elements of yeast chromosomes, and allow the vector to be replicated and maintained in yeast cells in vivo. Yeast elements include a centromere, an autonomous replication sequence, a pair of telomeres, yeast selectable markers, and usually a bacterial origin of replication and selectable marker for replication and selection of the YAC vector arms in bacteria.

YACs may be used in combination with gene targeting of endogenous loci for insertion into the host animal's genome. An advantage of using YACs is that hundreds of kilobases of DNA may be inserted into a host cell. Therefore, the use of YAC cloning vehicles permits inclusion of a substantial portion of the transgene region. A further advantage is that sequences can be deleted or inserted onto the YAC by utilizing high frequency homologous recombination in yeast. This provides for facile engineering of the YAC transgenes.

Another strategy of incorporating large segments of human nucleic acid into mammals, such as occurs for the creation of human antibodies is known as the "minilocus approach". The "minilocus approach" is directed to facsimile reproduction of the locus for the gene of interest (such as an immunoglobulin) through inclusion of individual genes which comprise the locus. For example, when the locus is an immunoglobulin, the component genes may be one or more VH genes, one or more DH genes, one or more JH genes, a mu constant region, a second constant region can be formed into a single construct for insertion into the animal. Examples of this approach are described in U.S. Pat. No. 5,545,807 to Surani et al., U.S. Pat. Nos. 5,545,806, 5,625,825, 5,625,126, 5,633,425, 5,661,016, 5,770,429, 5,789,650 and 5,814,318 each to Lonberg and Kay, U.S. Pat. No. 5,591,669 to Krimpenfort and Berns, U.S. Pat. Nos. 5,612,205, 5,721,367, 5,789,215 to Berns et al. and U.S. Pat. No. 5,643,763 to Choi and Dunn, European Patent No. 0 546 073 B1 and International Patent Application Nos. WO 92/03918, WO 92/22645, WO 92/22647, WO 92/22670, WO 93/12227, WO 94/00569, WO 94/25585, WO 96/14436, WO 97/13852 and 98/24884. Additional examples appear in Taylor et al., *Nucleic Acids Res.* 20: 6287-6295 (1992), Chen et al., *Inter. Immunol.* 5: 647-656 (1993), Tuaillon et al., *J. Immunol.* 154: 6453-6465 (1995), Choi et al., *Nature Genetics* 4: 117-123 (1993), Lonberg et al., *Nature* 368: 856-859 (1994), Taylor et al., *Internat. Immunol.* 6: 579-591 (1994), Tuaillon et al., *J. Immunol.* 154: 6453-6465 (1995) and Fishwild et al., *Nature Biotech.* 14: 845-851 (1996).

Yet another strategy for introducing human nucleic acid into mammalian cells is termed "microcell fusion". In microcell fusion, portions or whole human chromosomes can be introduced into mice as described in European Patent No. EP 0 843 961 A1. Because this approach results in a transgene comprising a substantial amount of genetic material, when a particular locus comprises many genes, there is typically not a great degree of control over the profile of expression of each particular gene. Another difficulty with microcell fusion is that the transchromosomes are mitotically and meiotically unstable. For example, when the transgene was an immunoglobulin locus, the transchromosomes encoding human IgH, IgK or both were lost with a frequency approaching 80%.

I. Uses of GLM-R Polynucleotide and Polypeptides Encoded Thereby for Disorders, Related to the Over or Under Abundance of Monocytes or Macrophages.

The invention is also directed to the use of GLM-R DNA, polypeptides encoded therefrom, including peptide fragments thereof and antibodies directed thereagainst and peptide fragments for various particular uses related to the diagnosis and treatment disorders related to the over or under abundance of monocytes or macrophages.

Such uses include, for example: (1) prognostic and diagnostic evaluation disorders related to the over or under abundance of monocytes or macrophages and the identification of individuals at risk for developing such disorders; (2) methods for the treatment of disorders related to the over or under abundance of monocytes or macrophages; (3) identification of compounds which modulate the expression of the GLM-R DNA or activity of GLM-R polypeptide (4). More specifically, such uses on an individual include, the detection of the presence of a GLM-R mutant, or the detection of either over- or under-expression of GLM-R polypeptide relative to wild type expression levels, non-diseased organisms having genetic profile which correlates with a diseased state, or the susceptibility toward disorders related to the over or under abundance of monocytes or macrophages.

The methods described herein may be performed, for example, by utilizing pre-packaged diagnostic kits comprising at least one specific GLM-R nucleic acid or anti-GLM-R polypeptide described herein, which may be used to screen and diagnose individuals exhibiting body weight disorder abnormalities, and then screen such individuals having a predisposition to developing a disorder related to the over or under abundance of monocytes or macrophages.

In the detection of GLM-R mutants, any nucleated cell from the individual in question can be used as a source for genomic nucleic acid. In the detection of GLM-R expression, any cell type or tissue in which the GLM-R DNA is expressed may be utilized, such as, for example, tissues or cells shown herein to express the GLM-R DNA. Examples of both nucleic acid-based as well as peptide-based detection techniques are described below.

(1) Detection of GLM-R Nucleic Acid

Mutations or polymorphisms within the GLM-R DNA can be detected through a number of techniques. Nucleic acid from any nucleated cell can be used as the starting point for such assay techniques, and may be isolated according to standard nucleic acid preparation procedures which are well known to those of skill in the art.

Genomic DNA may be used in hybridization or amplification assays of biological samples to detect abnormalities involving GLM-R gene structure, including point mutations, insertions, deletions and chromosomal rearrangements. Such assays may include, but are not limited to, Southern analyses, single stranded conformation polymorphism analyses (SSCP), and PCR analyses.

Diagnostic methods for the detection of GLM-R gene-specific mutations can involve for example, contacting and incubating nucleic acids obtained from a sample, e.g., derived from a patient sample or other appropriate cellular source with one or more labeled nucleic acid reagents including recombinant DNA molecules, cloned genes or degenerate variants thereof, under conditions favorable for the specific annealing of these reagents to their complementary sequences within or flanking the GLM-R gene. Preferably, the lengths of such nucleic acid reagents can be at least 15 to 30 nucleotides.

After incubation, all non-annealed nucleic acids are removed from the nucleic acid:GLM-R molecule hybrid. The presence of nucleic acids that have hybridized, if any such molecules exist, is then detected. Using such a detection scheme, the nucleic acid from the cell type or tissue of interest can be immobilized, for example, to a solid support such as a membrane, or a plastic surface such as that on a microtiter plate or polystyrene beads. In this case, after incubation, non-annealed, labeled nucleic acid reagents are easily removed. Detection of the remaining, annealed, labeled GLM-R nucleic acid reagents is accomplished using standard techniques well-known to those in the art. The GLM-R DNA sequences to which the nucleic acid reagents have annealed can be compared to the annealing pattern expected from a normal GLM-R DNA sequence in order to determine whether a GLM-R DNA mutation is present.

In a preferred embodiment, GLM-R gene mutations or polymorphisms can be detected by using a microassay of GLM-R nucleic acid sequences immobilized to a substrate or "gene chip" (see, e.g. Cronin, et al., *Human Mutation* 7:244-255)(1996).

Alternative diagnostic methods for the detection of GLM-R gene specific nucleic acid molecules, in patient samples or other appropriate cell sources, may involve their amplification, e.g., by PCR (the experimental embodiment set forth in U.S. Pat. No. 4,683,202), followed by the analysis of the amplified molecules using techniques well known to those of skill in the art, such as, for example, those listed above. The resulting amplified sequences can be compared to those that would be expected if the nucleic acid being amplified contained only normal copies of the GLM-R gene in order to determine whether a GLM-R gene mutation exists.

Among those GLM-R nucleic acid sequences which are preferred for such amplification-related diagnostic screening analyses are oligonucleotide primers which amplify GLM-R exon sequences. The sequences of such oligonucleotide primers are, therefore, preferably derived from GLM-R intron sequences so that the entire exon, or coding region, can be analyzed as discussed below. Primer pairs useful for amplification of GLM-R exons are preferably derived from adjacent introns. Appropriate primer pairs can be chosen such that each of the 25 GLM-R exons are amplified.

Primers for the amplification of GLM-R exons can be routinely designed by one of ordinary skill in the art by utilizing the coding and unstranslated sequences of GLM-R shown in FIG. 1. Additional GLM-R nucleic acid sequences which are preferred for such amplification-related analyses are those which will detect the presence of a GLM-R polymorphism. Such polymorphisms include ones which represent mutations associated with disorders related to the over or under abundance of monocytes or macrophages.

Further, well-known genotyping techniques can be performed to type polymorphisms that are in close proximity to mutations in the GLM-R gene itself, including mutations associated with disorders related to the over or under abundance of monocytes or macrophages. Such polymorphisms can be used to identify individuals in families likely to carry mutations in the GLM-R gene. If a polymorphism exhibits linkage disequilibrium with mutations in the GLM-R gene, the polymorphism can also be used to identify individuals in the general population who are likely to carry such mutations.

Polymorphisms that can be used in this way include restriction fragment length polymorphisms (RFLPs), which involve sequence variations in restriction enzyme target sequences, single-base polymorphisms, and simple sequence length polymorphisms (SSLPs). For example, U.S. Pat. No. 5,075,217 describes a DNA marker based on length polymorphisms in blocks of (dC-dA)n-(dG-dT)n short tandem repeats. The average separation of (dC-dA)n-(dG-dT)n blocks is estimated to be 30,000-60,000 bp. Markers that are so closely spaced exhibit a high frequency co-inheritance, and are extremely useful in the identification of genetic mutations, such as, for example, mutations within the GLM-R gene, and the diagnosis of diseases and disorders related to mutations in the GLM-R gene.

Also, U.S. Pat. No. 5,364,759 describes a DNA profiling assay for detecting short tri and tetra nucleotide repeat sequences. The process includes extracting the DNA of interest, such as the GLM-R gene, amplifying the extracted DNA, and labelling the repeat sequences to form a genotypic map of the individual's DNA.

A GLM-R probe could additionally be used to directly identify RFLPs. Further, a GLM-R probe or primers derived from the GLM-R sequence could be used to isolate genomic clones such as YACs, BACs, PACs, cosmids, phage, or plasmids.

The DNA contained in these clones can be screened for single-base polymorphisms or SSLPs using standard hybridization or sequencing procedures. The level of GLM-R gene expression can also be assayed. For example, RNA from a cell type or tissue known, or suspected, to express the GLM-R gene, such as muscle, brain, kidney, testes, heart, liver, lung, skin, hypothalamus, spleen, and adipose tissue may be isolated and tested utilizing hybridization or PCR techniques such as are described, above. The isolated cells can be derived from cell culture or from a patient. The analysis of cells taken from culture may be a necessary step in the assessment of cells to be used as part of a cell-based gene therapy technique or, alternatively, to test the effect of compounds on the expression of the GLM-R gene. Such analyses may reveal both quantitative and qualitative aspects of the expression pattern of the GLM-R gene, including activation or inactivation of GLM-R gene expression.

In one embodiment of such a detection scheme, a cDNA molecule is synthesized from an RNA molecule of interest (e.g., by reverse transcription of the RNA molecule into cDNA). All or part of the resulting cDNA is then used as the template for a nucleic acid amplification reaction, such as a PCR amplification reaction, or the like. The nucleic acid reagents used as synthesis initiation reagents (e.g., primers) in the reverse transcription and nucleic acid amplification steps of this method are chosen from among the GLM-R gene nucleic acid reagents described herein.

The preferred lengths of such nucleic acid reagents are at least 9-30 nucleotides. For detection of the amplified product, the nucleic acid amplification may be performed using radioactively or non-radioactively labeled nucleotides. Alternatively, enough amplified product may be made such that the product may be visualized by standard ethidium bromide staining or by utilizing any other suitable nucleic acid staining method.

As an alternative to amplification techniques, standard Northern analyses can be performed to determine the level of mRNA expression of the GLM-R gene, if a sufficient quantity of the appropriate cells can be obtained.

Additionally, it is possible to perform such GLM-R gene expression assays "in situ", i.e., directly upon tissue sections (fixed and/or frozen) of patient tissue obtained from biopsies or resections, such that no nucleic acid purification is necessary. Nucleic acid reagents such as those described herein may be used as probes and/or primers for such in situ procedures (see, for example, Nuovo, G. J., 1992, "PCR In Situ Hybridization: Protocols and Applications", Raven Press, NY).

(2) Detection of GLM-R Gene Products

GLM-R gene products, including both native sequence, variants, and polypeptide fragments thereof, may be detected using antibodies which are directed against such GLM-R gene products. Such anti-GLM-R antibodies may be used as diagnostics and prognostics for disorders related to the over or under abundance of monocytes or macrophages. Such methods may be used to detect abnormalities in the level of GLM-R gene expression or of GLM-R gene product synthesis, or abnormalities in the structure, temporal expression, and/or physical location of GLM-R gene product. The antibodies and immunoassay methods described herein have, for example, important in vitro applications in assessing the efficacy of treatments for disorders related to the over or under abundance of monocytes or macrophages. Antibodies, or fragments of antibodies, such as those described below, may be used to screen potentially therapeutic compounds in vitro to determine their effects on GLM-R gene expression and GLM-R gene product production. The compounds that have beneficial effects on disorders related to the over or under abundance of monocytes or macrophages, can thereby be identified, and a therapeutically effective dose determined.

In vitro immunoassays may also be used, for example, to assess the efficacy of cell-based gene therapy for disorders related to the over or under abundance of monocytes or macrophages. Antibodies directed against GLM-R gene products may be used in vitro to determine, for example, the level of GLM-R gene expression achieved in cells genetically engineered to produce GLM-R gene product. In the case of intracellular GLM-R gene products, such an assessment is done, preferably, using cell lysates or extracts. Such analysis will allow for a determination of the number of transformed cells necessary to achieve therapeutic efficacy in vivo, as well as optimization of the gene replacement protocol.

The tissue or cell type to be analyzed will generally include those that are known, or suspected, to express a GLM-R gene. The protein isolation methods employed herein may, for example, be such as those described in Harlow and Lane (1988, "Antibodies: A Laboratory Manual", Cold Spring Harbor Laboratory Press, Cold Spring Harbor, N.Y.). The isolated cells can be derived from cell culture or from a patient. The analysis of cells taken from culture may be a necessary step in the assessment of cells to be used as part of a cell-based gene therapy technique or, alternatively, to test the effect of compounds on the expression of the GLM-R gene.

Preferred diagnostic methods for the detection of GLM-R gene products, conserved variants or peptide fragments thereof, may involve, for example, immunoassays wherein the GLM-R gene products or conserved variants or peptide fragments are detected by their interaction with an anti-GLM-R gene product-specific antibody.

For example, antibodies, or fragments of antibodies, such as those described, above, may be used to quantitatively or qualitatively detect the presence of GLM-R gene products or conserved variants or peptide fragments thereof. This can be accomplished, for example, by immunofluorescence techniques employing a fluorescently labeled antibody coupled with light microscopic, flow cytometric, or fluorimetric detection. Such techniques are especially preferred for GLM-R gene products that are expressed on the cell surface.

The antibodies (or fragments thereof) useful in the present invention may, additionally, be employed histologically, as in immunofluorescence or immunoelectron microscopy, for in situ detection of GLM-R gene products, conserved variants or peptide fragments thereof. In situ detection may be accomplished by removing a histological specimen from a patient, and applying thereto a labeled antibody that binds to a GLM-R polypeptide. The antibody (or fragment) is preferably applied by overlaying the labeled antibody (or fragment) onto a biological sample. Through the use of such a procedure, it is possible to determine not only the presence of the GLM-R gene product, conserved variants or peptide fragments, but also its distribution in the examined tissue. Using the present invention, those of ordinary skill will readily recognize that any of a wide variety of histological methods (such as staining procedures) can be modified in order to achieve in situ detection of a GLM-R gene product.

Immunoassays for GLM-R gene products, conserved variants, or peptide fragments thereof will typically comprise: (1) incubating a sample, such as a biological fluid, a tissue extract, freshly harvested cells, or lysates of cells in the presence of a detectably labeled antibody capable of identifying GLM-R gene products, conserved variants or peptide fragments thereof; and (2) detecting the bound antibody by any of a number of techniques well-known in the art.

The biological sample may be brought in contact with and immobilized onto a solid phase support or carrier, such as nitrocellulose, that is capable of immobilizing cells, cell particles or soluble proteins. The support may then be washed with suitable buffers followed by treatment with the detectably labeled GLM-R gene product specific antibody.

The solid phase support may then be washed with the buffer a second time to remove unbound antibody. The amount of bound label on the solid support may then be detected by conventional means.

"Solid phase support or carrier" means any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

One method for detectably labeling an GLM-R gene product-specific antibody is through linkage to a readily detectable enzyme, such as an enzyme immunoassay (EIA) (Voller, A., "The Enzyme Linked Immunosorbent Assay (ELISA)II, *Diagnostic Horizons* 2: 1-7, Microbiological Associates Quarterly Publication, Walkersville, Md.) (1978); Voller, A. et al., *J. Clin. Pathol.* 31, 507-520 (1978); Butler, J. E., *Meth. Enzymol.* 73: 482-523 (1981); Maggio, E. (ed.), *Enzyme Immunoassay*, CRC Press, Boca Raton, Fla. (1980); Ishikawa, E., et al. (eds.), *Enzyme Immunoassay*, Kgaku Shoin, Tokyo (1981). The enzyme which is bound to the antibody will react with an appropriate substrate, preferably a chromogenic substrate, in such a manner as to produce a chemical moiety that can be detected, for example, by spectrophotometric, fluorimetric or by visual means. Enzymes that can be used to detectably label the antibody include, but are not limited to, malate dehydrogenase, staphylococcal nuclease, delta-5-steroid isomerase, yeast alcohol dehydrogenase, α-glycerophosphate, dehydrogenase, triose phosphate isomerase, horseradish peroxidase, alkaline phosphatase, asparaginase, glucose oxidase, β-galactosidase, ribonuclease, urease, catalase, glucose-6-phosphate dehydrogenase, glucoamylase and acetylcholinesterase. The detection can be accomplished by colorimetric methods that employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect GLM-R gene products through the use of a radioimmunoassay (RIA) (see, for example, Weintraub, B., Principles of Radioimmunoassays, Seventh Training Course on Radioligand Assay Techniques, The Endocrine Society, March, 1986). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}Eu$, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

(3) Screening Assays for Compounds that Interact with GLM-R Nucleic Acid or Gene Product The following assays are designed to identify compounds that bind to an GLM-R gene product, compounds that bind to proteins, or portions of proteins that interact with am GLM-R gene product, compounds that interfere with the interaction of an GLM-R gene product with proteins and compounds that modulate the activity of the GLM-R gene (i.e., modulate the level of GLM-R gene expression and/or modulate the level of GLM-R gene product activity). Assays may additionally be utilized that identify compounds that bind to GLM-R gene regulatory sequences (e.g., promoter sequences; see e.g., Platt, *J. Biol. Chem.* 269: 28558-28562 (1994), which is incorporated herein by reference in its entirety, and that can modulate the level of GLM-R gene expression. Such compounds may include, but are not limited to, small organic molecules, such as ones that are able to cross the blood-brain barrier, gain to and/or entry into an appropriate cell and affect expression of the GLM-R gene or some other gene involved in the body weight regulatory pathway, or intracellular proteins.

Methods for the identification of such proteins are described, below. Such proteins may be involved in disorders related to the over or under abundance of monocytes or macrophages. Furthermore, among these compounds are compounds that affect the level of GLM-R gene expression and/or GLM-R gene is product activity and that can be used in the therapeutic treatment of disorders related to the over or under abundance of monocytes or macrophages.

Compounds may include, but are not limited to, peptides such as, for example, soluble peptides, including but not limited to, Ig-tailed fusion peptides, and members of random peptide libraries; (see, e.g., Lam et al., *Nature* 354: 82-84 (1991); Houghten et al., *Nature* 354: 84-86 (1991), and combinatorial chemistry-derived molecular library made of D- and/or L-configuration amino acids, phosphopeptides (including, but not limited to members of random or partially degenerate, directed phosphopeptide libraries; see, e.g., Songyang et al., *Cell* 72: 767-778 (1993), antibodies (including, but not limited to, polyclonal, monoclonal, humanized, anti-idiotypic, chimeric or single chain antibodies, and Fab, F(ab'), and Fab expression library fragments, and epitope-binding fragments thereof), and small organic or inorganic molecules.

Compounds identified via assays such as those described herein may be useful, for example, in elaborating the biological function of the GLM-R gene product and for ameliorating disorders related to the over or under abundance of monocytes or macrophages.

(a) In vitro Screening Assays for Compounds that Bind to GLM-R Gene Product

In vitro systems may be designed to identify compounds capable of binding the GLM-R gene products of the invention. Compounds identified may be useful, for example, in modulating the activity of unimpaired and/or mutant GLM-R gene products, in elaborating the biological function of the GLM-R gene product, in screens for identifying compounds that disrupt normal GLM-R gene product interactions, or may in themselves disrupt such interactions.

The principle of the assays used to identify compounds that bind to the GLM-R gene product involves preparing a reaction mixture of the GLM-R gene product and the test compound under conditions and for a time sufficient to allow the two components to interact and bind, thus forming a complex that can be removed and/or detected in the reaction mixture. These assays can be conducted in a variety of ways. For example, one method to conduct such an assay involves anchoring a GLM-R gene product or a test substance onto a solid support and detecting GLM-R gene product/test compound complexes formed on the solid support at the end of the reaction. In one embodiment of such a method, the GLM-R gene product may be anchored onto a solid support, and the test compound, which is not anchored, may be labeled, either directly or indirectly.

In practice, microtiter plates are conveniently utilized as the solid support. The anchored component may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the previously non-immobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for GLM-R gene product or the test compound to anchor any complexes formed in solution, and a labeled antibody specific for the other component of the possible complex to detect anchored complexes.

(b) Assays for Proteins that Interact with the GLM-R Gene Product

Any method suitable for detecting protein-protein interactions may be employed for identifying GLM-R gene product-protein interactions. Among the traditional methods that may be employed are co-immunoprecipitation, cross-linking and co-purification through gradients or chromatographic columns. Utilizing procedures such as these allows for the identification of proteins that interact with GLM-R gene products. Such proteins can include, but are not limited, the GLM-R gene product. Once isolated, such a protein can be identified and can be used in conjunction with standard techniques, to identify proteins it interacts with. For example, at least a portion of the amino acid sequence of a protein that interacts with the GLM-R gene product can be ascertained using techniques well known to those of skill in the art, such as via the Edman degradation technique (see, e.g., Creighton, "Proteins: Structures and Molecular Principles," W.H. Freeman & Co., N.Y., pp. 34-49 (1983). The amino acid sequence obtained may be used as a guide for the generation of oligonucleotide mixtures that can be used to screen for gene sequences encoding such proteins. Screening may be accomplished, for example, by standard hybridization or PCR techniques. Techniques for the generation of oligonucleotide mixtures and the screening are well-known. (See, e.g., Ausubel, supra, and 1990, "PCR Protocols: A Guide to Methods and Applications," Innis et al., eds. Academic Press, Inc., New York).

Additionally, methods may be employed that result in the simultaneous identification of genes that encode a protein which interacts with a GLM-R gene product. These methods include, for example, probing expression libraries with labeled GLM-R gene product, using GLM-R gene product in a manner similar to the well known technique of antibody probing of Xgt11 libraries. One method that detects protein interactions in vivo, the two-hybrid system, is described in detail for illustration only and not by way of limitation. One version of this system has been described (Chien, et al., Proc. Natl. Acad. Sci. USA 88: 9578-9582 (1991) and is commercially available from Clontech (Palo Alto, Calif.).

Briefly, utilizing such a system, plasmids are constructed that encode two hybrid proteins: one consists of the DNA-binding domain of a transcription activator protein fused to the GLM-R gene product and the other consists of the transcription activator protein's activation domain fused to an unknown protein that is encoded by a cDNA that has been recombined into this plasmid as part of a cDNA library. The DNA-binding domain fusion plasmid and the cDNA library are transformed into a strain of the yeast Saccharomyces cerevisiae that contains a reporter gene (e.g., HBS or lacZ) whose regulatory region contains the transcription activator's binding site. Either hybrid protein alone cannot activate transcription of the reporter gene: the DNA-binding domain hybrid cannot because it does not provide activation function and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodologies may be used to screen activation domain libraries for proteins that interact with the "bait" gene product. By way of example, and not by way of limitation, GLM-R gene products may be used as the bait gene product. Total genomic or cDNA sequences are fused to the DNA encoding an activation domain.

This library and a plasmid encoding a hybrid of a bait GLM-R gene product fused to the DNA-binding domain are co-transformed into a yeast reporter strain, and the resulting transformants are screened for those that express the reporter gene. For example, a bait GLM-R gene sequence, such as the open reading frame of the GLM-R gene, can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with bait GLM-R gene product are to be detected can be made using methods routinely practiced in the art. According to the particular system described herein, for example, the cDNA fragments can be inserted into a vector such that they are translationally fused to the transcriptional activation domain of GAL4. Such a library can be co-transformed along with the bait GLM-R gene-GAL4 fusion plasmid into a yeast strain that contains a lacZ gene driven by a promoter that contains GAL4 activation sequence.

A cDNA encoded protein, fused to a GAL4 transcriptional activation domain that interacts with bait GLM-R gene product will reconstitute an active GAL4 protein and thereby drive expression of the HIS3 gene. Colonies that express HIS3 can be detected by their growth on petri dishes containing semi-solid agar based media lacking histidine.

The cDNA can then be purified from these strains, and used to produce and isolate the bait GLM-R gene product-interacting protein using techniques routinely practiced in the art.

(c) Assays for Compounds that Interfere with GLM-R Gene Product Macromolecule Interaction The GLM-R gene products may, in vivo, interact with one or more macromolecules, such as proteins. For example, the GLM-R gene-products may, in vivo, interact with the GLM-R gene products. Other macromolecules which interact with the GLM-R gene products may include, but are not limited to, nucleic acid molecules and those proteins identified via methods such as those described herein. For purposes of this discussion, the macromolecules are referred to herein as "binding partners". Compounds that disrupt GLM-R gene product binding to a binding partner may be useful in regulating the activity of the GLM-R gene product, especially mutant GLM-R gene products. Such compounds may include, but are not limited to molecules such as peptides, and the like.

The basic principle of an assay system used to identify compounds that interfere with the interaction between the GLM-R gene product and a binding partner or partners involves preparing a reaction mixture containing the GLM-R gene product and the binding partner under conditions and for a time sufficient to allow the two to interact and bind, thus forming a complex. In order to test a compound for inhibitory activity, the reaction mixture is prepared in the presence and absence of the test compound. The test compound may be initially included in the reaction mixture, or may be added at a time subsequent to the addition of GLM-R gene product and its binding partner. Control reaction mixtures are incubated without the test compound or with a compound which is known not to block complex formation. The formation of any complexes between the GLM-R gene product and the binding partner is then detected. The formation of a complex in the control reaction, but not in the reaction mixture containing the test compound, indicates that the compound interferes with the interaction of the GLM-R gene product and the binding partner. Additionally, complex formation within reaction mixtures containing the test compound and normal GLM-R gene product may also be compared to complex formation within reaction mixtures containing the test compound and a mutant GLM-R gene product. This comparison may be important in those cases wherein it is desirable to identify compounds that disrupt interactions of mutant but not normal GLM-R gene product.

The assay for compounds that interfere with the interaction of the GLM-R gene products and binding partners can be conducted in a heterogeneous or homogeneous format. Heterogeneous assays involve anchoring either the GLM-R gene product or the binding partner onto a solid support and detecting complexes formed on the solid support at the end of the reaction. In homogeneous assays, the entire reaction is carried out in a liquid phase. In either approach, the order of addition of reactants can be varied to obtain different information about the compounds being tested. For example, test compounds that interfere with the interaction between the GLM-R gene products and the binding partners, e.g., by competition, can be identified by conducting the reaction in the presence of the test substance; i.e., by adding the test substance to the reaction mixture prior to or simultaneously with the GLM-R gene product and interactive intracellular binding partner. Alternatively, test compounds that disrupt preformed complexes, e.g., compounds with higher binding constants that displace one of the components from the complex, can be tested by adding the test compound to the reaction mixture after complexes have been formed. The various formats are described briefly below.

In a heterogeneous assay system, either the GLM-R gene product or the interactive binding partner, is anchored onto a solid surface, while the non-anchored species is labeled, either directly or indirectly. In practice, microtiter plates are conveniently utilized. The anchored species may be immobilized by non-covalent or covalent attachments. Non-covalent attachment may be accomplished simply by coating the solid surface with a solution of the GLM-R gene product or binding partner and drying. Alternatively, an immobilized antibody specific for the species to be anchored may be used to anchor the species to the solid surface. The surfaces may be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, may be directly labeled or indirectly labeled with a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex formation or that disrupt preformed complexes can be identified.

In an alternate embodiment of the invention, a homogeneous assay can be used. In this approach, a preformed complex of the GLM-R gene product and the interactive binding partner is prepared in which either the GLM-R gene product or its binding partners is labeled, but the signal generated by the label is quenched due to complex formation (see, e.g., U.S. Pat. No. 4,109,496 by Rubenstein which utilizes this approach for immunoassays). The addition of a test substance that competes with and displaces one of the species from the preformed complex will result in the generation of a signal above background. In this way, test substances that disrupt GLM-R gene product/binding partner interaction can be identified.

In another embodiment of the invention, these same techniques can be employed using peptide fragments that correspond to the binding domains of the GLM-R gene product and/or the binding partner (in cases where the binding partner is a protein), in place of one or both of the full length proteins. Any number of methods routinely practiced in the art can be used to identify and isolate the binding sites. These methods include, but are not limited to, mutagenesis of the gene encoding one of the proteins and screening for disruption of binding in a co-immunoprecipitation assay. Compensating mutations in the gene encoding the second species in the complex can then be selected. Sequence analysis of the genes encoding the respective proteins will reveal the mutations that correspond to the region of the protein involved in interactive binding. Alternatively, one protein can be anchored to a solid surface using methods described in this Section above, and allowed to interact with and bind to its labeled binding partner, which has been treated with a proteolytic enzyme, such as trypsin. After washing, a short, labeled peptide comprising the binding domain may remain associated with the solid material, which can be isolated and identified by amino acid sequencing. Also, once the gene coding for the segments is engineered to express peptide fragments of the protein, it can then be tested for binding activity and purified or synthesized.

For example, and not by way of limitation, a GLM-R gene product can be anchored to a solid material as described, above, in this Section by making a GST-1 fusion is protein and allowing it to bind to glutathione agarose beads. The binding partner can be labeled with a radioactive isotope, such as $^{35}S$, and cleaved with a proteolytic enzyme such as trypsin. Cleavage products can then be added to the anchored GST-1 fusion protein and allowed to bind. After washing away unbound peptides, labeled bound material, representing the binding partner binding domain, can be eluted, purified, and analyzed for amino acid sequence by well-known methods. Peptides so identified can be produced synthetically or produced using recombinant DNA technology.

(d) Assays for the Identification of Compounds Useful in the Treatment of Body Weight Disorders Compounds, including but not limited to binding compounds identified via assay techniques such as those described previously can be tested for the ability to treat symptoms of body weight disorders. It should be noted that the assays described herein can identify compounds that affect GLM-R activity by either affecting GLM-R gene expression or by affecting the level of GLM-R gene product activity. For example, compounds may be identified that are involved in another step in the pathway in which the GLM-R gene and/or GLM-R gene product is involved, such as, for example, a step which is either "upfield" or "downfield" of the step in the pathway mediated by the GLM-R gene. Such compounds may, by affecting this same pathway, modulate the effect of GLM-R on the development of body weight disorders. Such compounds can be used as part of a therapeutic method for the treatment of the disorder.

Described below are cell-based and animal model-based assays for the identification of compounds exhibiting such an ability to ameliorate symptoms of body weight disorders. First, cell-based systems can be used to identify compounds that may act to ameliorate symptoms of body weight disorders. Such cell systems can include, for example, recombinant or non-recombinant cell, such as cell lines, that express the GLM-R gene.

In utilizing such cell systems, cells that express GLM-R may be exposed to a compound suspected of exhibiting an ability to ameliorate body weight disorder symptoms, at a sufficient concentration and for a sufficient time to elicit such an amelioration of such symptoms in the exposed cells. After exposure, the cells can be assayed to measure alterations in the expression of the GLM-R gene, e.g., by assaying cell lysates for GLM-R mRNA transcripts (e.g., by Northern analysis) or for GLM-R gene products expressed by the cell; compounds that modulate expression of the GLM-R gene are good candidates as therapeutics.

In addition, animal-based systems or models for a mammalian body weight disorder, for example, transgenic mice containing a human or altered form of GLM-R gene, may be used to identify compounds capable of ameliorating symptoms of the disorder. Such animal models may be used as test substrates for the identification of drugs, pharmaceuticals, therapies and interventions. For example, animal models may be exposed to a compound suspected of exhibiting an ability to ameliorate symptoms, at a sufficient concentration and for a sufficient time to elicit such an amelioration of body weight disorder symptoms. The response of the animals to the exposure may be monitored by assessing the reversal of the symptoms of the disorder.

With regard to intervention, any treatments that reverse any aspect of body weight disorder-like symptoms should be considered as candidates for human therapeutic intervention in such a disorder.

(4) Compounds and Methods for the Treatment of Disorders Related to the Over or Under Abundance of Monocytes or Macrophages Described below are methods and compositions whereby disorders related to the over or under abundance of monocytes or macrophages, may be treated. Such methods can comprise, for example administering compounds which modulate the expression of a mammalian GLM-R gene and/or the synthesis or activity of a mammalian GLM-R gene product, so that symptoms of the disorders related to the over or under abundance of monocytes or macrophages are ameliorated. Alternatively, in those instances whereby the disorders related to the over or under abundance of monocytes or macrophages results from GLM-R gene mutations, such methods can comprise supplying the mammal with a nucleic acid molecule encoding an unimpaired GLM-R gene product such that an unimpaired GLM-R gene product is expressed and symptoms of the disorder are ameliorated. In another embodiment of methods for the treatment of mammalian body weight disorders resulting from GLM-R gene mutations, such methods can comprise supplying the mammal with a cell comprising a nucleic acid molecule that encodes an unimpaired GLM-R gene product such that the cell expresses the unimpaired GLM-R gene product, and symptoms of the disorder are ameliorated.

Alternatively, symptoms of disorders related to the over or under abundance of monocytes or macrophages, may be ameliorated by increasing the level of GLM-R gene expression and/or GLM-R gene product activity.

(a) Inhibitory Antisense, Ribozyme and Triple Helix Approaches

In another embodiment, symptoms of disorders related to the over or under abundance of monocytes or macrophages may be ameliorated by decreasing the level of GLM-R gene expression and/or GLM-R gene product activity by using GLM-R gene sequences in conjunction with well-known antisense, gene "knock-out," ribozyme and/or triple helix methods to decrease the level of GLM-R gene expression. Among the compounds that may exhibit the ability to modulate the activity, expression or synthesis of the GLM-R gene, including the ability to ameliorate the symptoms of a mammalian body weight disorder, are antisense, ribozyme, and triple helix molecules. Such molecules may be designed to reduce or inhibit either unimpaired, or if appropriate, mutant target gene activity. Techniques for the production and use of such molecules are well known to those of skill in the art.

Antisense RNA and DNA molecules act to directly block the translation of mRNA by hybridizing to targeted mRNA and preventing protein translation. Antisense approaches involve the design of oligonucleotides that are complementary to a target gene mRNA. The antisense oligonucleotides will bind to the complementary target gene mRNA transcripts and prevent translation. Absolute complementarily, although preferred, is not required.

A sequence "complementary" to a portion of an RNA, as referred to herein, means a sequence having sufficient complementarily to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarily and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

In one embodiment, oligonucleotides complementary to non-coding regions of the GLM-R gene could be used in an antisense approach to inhibit translation of endogenous GLM-R mRNA. Antisense nucleic acids should be at least six nucleotides in length, and are preferably oligonucleotides ranging from 6 to about 50 nucleotides in length. In specific aspects the oligonucleotide is at least nucleotides, at least 17 nucleotides, at least 25 nucleotides or at least 50 nucleotides.

Regardless of the choice of target sequence, it is preferred that in vitro studies are first performed to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., *Proc. Natl. Acad. Sci. U.S.A.* 86: 6553-6556 (1989); Lemaitre et al., *Proc. Natl. Acad. Sci. U.S.A.* 84, 648-652 (1987); PCT Publication No. WO88/09810, published Dec. 15, 1988) or the blood-brain barrier (see e.g., PCT Publication No. WO89/10134, published Apr. 25, 1988), hybridization-triggered cleavage agents (see, e.g., Krol et al, *BioTechniques* 6: 958-976 (1988) or intercalating agents (see e.g., Zon, *Pharm. Res.* 5: 539-549 (1988). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethyl-aminomethyluracil, dihydrouracil, beta-D-galactosylqueosine, inosine, NG-isopentenyladenine, 1-methylguanine, 1-methylinosine, 2,2-dimethyl guanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid-methylester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide may also comprise at least one modified sugar moiety selected from the group including but not limited to arabinose, 2-fluoroarabinose, xylulose, and hexose. Alternatively, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof. Alternatively still, the antisense oligonucleotide is an α-anomeric oligonucleotide. An α-anomeric oligonucleotide forms specific double-stranded hybrids with complementary RNA in which, contrary to the usual ~-units, the strands run parallel to each other (Gautier et al., *Nucl. Acids Res.* 15: 6625-6641 (1987). The oligonucleotide is a 2'-O-methylribonucleotide (Inoue et al., *Nucl. Acids Res.* 15: 6131-6148 (1987), or a chimeric RNA-DNA analogue (Inoue et al, *FEBS Lett.* 215: 327-330 (1987).

Oligonucleotides of the invention may he synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al., *Nucl Acids Res.* 16: 3209 (1988), methylphosphonate oligonucleotides can be prepared by use of controlled pore glass polymer supports (Sarin et al., *Proc. Natl. Acad. Sci. U.S.A.* 85: 7448-7451 (1988), etc.

While antisense nucleotides complementary to the target gene coding region sequence could be used, those complementary to the transcribed, untranslated region are most preferred.

Antisense molecules should be delivered to cells that express the target gene in vivo. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systemically.

However, it is often difficult to achieve intracellular concentrations of the antisense sufficient to suppress translation of endogenous mRNAs. Therefore a preferred approach utilizes' a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous target gene transcripts and thereby prevent translation of the target gene mRNA. For example, a vector can be introduced e.g., such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, *Nature* 290: 304-310 (1981), the promoter contained in the 3' long terminal repeat of Rous sarcoma virus (Yamamoto, et al., *Cell* 22: 787-797 (1980), the herpes thymidine kinase promoter (Wagner et al., *Proc. Natl. Acad. Sci. U.S.A.* 78: 1441-1445 (1961), the regulatory sequences of the metallothionein gene (Brinster et al., *Nature* 296: 39-42 (1982), etc. Any type of plasmid, cosmid, YAC or viral vector can be used to prepare the recombinant DNA construct which can be introduced directly into the tissue site. Alternatively, viral vectors can be used that selectively infect the desired tissue, in which case administration may be accomplished by another route (e.g., systemically). Ribozyme molecules designed to catalytically cleave target gene mRNA transcripts can also be used to prevent translation of target gene mRNA and, therefore, expression of target gene product. (See e.g., PCT International Publication WO90/11364, published Oct. 4, 1990; Sarver et al., *Science* 247: 1222-1225 (1990).

Ribozymes are enzymatic RNA molecules capable of catalyzing the specific cleavage of RNA. (For a review, see Rossi *Current Biology* 4: 469-471 (1994). The mechanism of ribozyme action involves sequence specific hybridization of the ribozyme molecule to complementary target RNA, followed by an endonucleolytic cleavage event. The composition of ribozyme molecules must include one or more sequences complementary to the target gene mRNA, and must include the well known catalytic sequence responsible for mRNA cleavage. For this sequence, see, e.g., U.S. Pat. No. 5,093,246, which is incorporated herein by reference in its entirety.

While ribozymes that cleave mRNA at site specific recognition sequences can be used to destroy target gene mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is, well known in the art and is described more fully in Myers, *Molecular Biology and Biotechnology: A Comprehensive Desk Reference*, VCH Publishers, New York, (see especially FIG. 4, page 833 (1995) and in Haseloff and Gerlach, *Nature* 334: 585-591 (1988), which is incorporated herein by reference in its entirety.

Preferably the ribozyme is engineered so that the cleavage recognition site is located near the 5' end of the target gene mRNA, i.e., to increase efficiency and minimize the intracellular-accumulation of non-functional mRNA transcripts.

The ribozymes of the present invention also include RNA endoribonucleases (hereinafter "Cech-type ribozymes") such as the one that occurs naturally in *Tetrahymena thermophila* (known as the IVS, or L-19 IVS RNA) and that has been extensively described by Thomas Cech and collaborators (Zaug et al., *Science* 224: 574-578 (1984); Zaug and Cech, *Science* 231: 470-475 (1986); Zaug et al., *Nature* 324: 429-433 (1986); published International patent application No. WO 88/04300 by University Patents Inc.; Been and Cech, *Cell* 47: 207-216 (1986). The Cech-type ribozymes have an eight base pair active site which hybridizes to a target RNA sequence whereafter cleavage of the target RNA takes place. The invention encompasses those Cech-type ribozymes which target eight base-pair active site sequences that are present in the target gene.

As in the antisense approach, the ribozymes can be composed of modified oligonucleotides (e.g., for improved stability, targeting, etc.) and should be delivered to cells that express the target gene in vivo. A preferred method of delivery involves using a DNA construct "encoding" the ribozyme under the control of a strong constitutive pol III or pol II promoter, so that transfected cells will produce sufficient quantities of the ribozyme to destroy endogenous target gene messages and inhibit translation. Because ribozymes unlike antisense molecules, are catalytic, a lower intracellular concentration is required for efficiency.

Endogenous target gene expression can also be reduced by inactivating or "knocking out" the target gene or its promoter using targeted homologous recombination (e.g., see Smithies et al., *Nature* 317: 230-234 (1985); Thomas and Capecchi, *Cell* 51: 503-512 (1987); Thompson et al, *Cell* 5: 313-321 (1989); each of which is incorporated by reference herein in its entirety). For example, a mutant, non-functional target gene (or a completely unrelated DNA sequence) flanked by DNA homologous to the endogenous target gene (either the coding regions or regulatory regions of the target gene) can be used, with or without a selectable marker and/or a negative selectable marker, to transfect cells that express the target gene in vivo. Insertion of the DNA construct, via targeted homologous recombination, results in inactivation of the target gene. Such approaches are particularly suited in the agricultural field where modifications to ES (embryonic stem) cells can be used to generate animal offspring with an inactive target gene (e.g., see Thomas and Capecchi, 1987 and Thompson, 1989, supra). However this approach can be adapted for use in humans provided the recombinant DNA constructs are directly administered or targeted to the required site in vivo using appropriate viral vectors.

Alternatively, endogenous target gene expression can be reduced by targeting deoxyribonucleotide sequences complementary to the regulatory region of the target gene (i.e., the target gene promoter and/or enhancers) to form triple helical structures that prevent transcription of the target gene in target cells in the body. (See generally, Helene, *Anticancer Drug Des.*, 6 (6): 569-584 (1991); Helene et al., *Ann. N.Y. Acad. Sci.*, 660: 27-36 (1992); and Maher, *Bioassays* 14(12): 807-815 (1992).

Nucleic acid molecules to be used in triplex helix formation for the inhibition of transcription should be single stranded and composed of deoxynucleotides. The base composition of these oligonucleotides must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and CGC' triplets across the three associated strands of the resulting triple helix. The pyrimidine-rich molecules provide base complementarily to a purine-rich region of a single strand of the duplex in a parallel orientation to that strand. In addition, nucleic acid molecules may be chosen that are purine-rich, for example, contain a stretch of G residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

In instances wherein the antisense, ribozyme, and/or triple helix molecules described herein are utilized to inhibit mutant gene expression, it is possible that the technique may so efficiently reduce or inhibit the transcription (triple helix) and/or translation (antisense, ribozyme) of mRNA produced by normal target gene alleles that the possibility may arise wherein the concentration of normal target gene product present may be lower than is necessary for a normal phenotype. In such cases, to ensure that substantially normal levels of target gene activity are maintained, therefore, nucleic acid molecules that encode and express target gene polypeptides exhibiting normal target gene activity may, be introduced into cells via gene therapy methods such as those described, below, that do not contain sequences susceptible to whatever antisense, ribozyme, or triple helix treatments are being utilized.

Alternatively, in instances whereby the target gene encodes an extracellular protein, it may be preferable to co-administer normal target gene protein in order to maintain the requisite level of target gene activity.

Anti-sense RNA and DNA, ribozyme, and triple helix molecules of the invention may be prepared by any method known in the art for the synthesis of DNA and RNA molecules, as discussed above. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

(b) Gene Replacement Therapy

The GLM-R gene nucleic acid sequences described herein can be utilized for the treatment of a disorders related to the over or under abundance of monocytes or macrophages. Such treatment can be in the form of gene replacement therapy. Specifically, one or more copies of a normal GLM-R gene or a portion of the GLM-R gene that directs the production of a GLM-R gene product exhibiting normal GLM-R gene function, may be inserted into the appropriate cells within a patient, using vectors that include, but are not limited to adenovirus, adeno-associated virus, and retrovirus vectors, in addition to other particles that introduce DNA into cells, such as liposomes.

Because the GLM-R gene is expressed in the brain, such gene replacement therapy techniques should be capable delivering GLM-R gene sequences to these cell types within patients. Thus, in one embodiment, techniques that are well known to those of skill in the art (see, e.g., PCT Publication No. WO89/10134, published Apr. 25, 1988) can be used to enable GLM-R gene sequences to cross the blood-brain barrier readily and to deliver the sequences to cells in the brain. With respect to delivery that is capable of crossing the blood-brain barrier, viral vectors such as, for example, those described above, are preferable.

In another embodiment, techniques for delivery involve direct administration of such GLM-R gene sequences to the site of the cells in which the GLM-R gene sequences are to be expressed.

Additional methods that may be utilized to increase the overall level of GLM-R gene expression and/or GLM-R gene product activity include using target homologous recombination methods, to modify the expression characteristic of an endogenous GLM-R gene in a cell or microorganism by inserting a heterologous DNA regulatory element such that the inserted regulatory element is operatively linked with the endogenous GLM-R gene in question. Targeted homologous recombination can he thus used to activate transcription of an endogenous GLM-R gene that is "transcriptionally silent", i.e., is not normally expressed, or to enhance the expression of an endogenous GLM-R gene that is normally expressed.

Further, the overall level of GLM-R gene expression and/or GLM-R gene product activity may be increased by the introduction of appropriate GLM-R-expressing cells, preferably autologous cells, into a patient at positions and in numbers that are sufficient to ameliorate body weight disorder symptoms. Such cells may be either recombinant or non-recombinant.

Among the cells that can he administered to increase the overall level of GLM-R gene expression in a patient are normal cells, preferably brain cells, that express the GLM-R gene. Alternatively, cells, preferably autologous cells, can be engineered to express GLM-R gene sequences, and may then be introduced into a patient in positions appropriate for the amelioration of a symptom of disorders related to the over or under abundance of monocytes or macrophages. Alternatively, cells that express an unimpaired GLM-R gene and that are from a MHC matched individual can be utilized, and may include, for example, brain cells. The expression of the GLM-R gene sequences is controlled by the appropriate gene regulatory sequences to allow such expression in the necessary cell types. Such gene regulatory sequences are well known to the skilled artisan. Such cell-based gene therapy techniques are well known to those skilled in the art, see e.g., U.S. Pat. No. 5,399,349. When the cells to be administered are non-autologous cells, they can be administered using well known techniques that prevent a host immune response against the introduced cells from developing. For example, the cells may be introduced in an encapsulated form which, while allowing for an exchange of components with the immediate extracellular environment, does not allow the introduced cells to be recognized by the host immune system.

Additionally, compounds, such as those identified via techniques such as those described herein, that are capable of modulating GLM-R gene product activity can be administered using standard techniques that are well known to those of skill in the art. In instances in which the compounds to be administered are to involve an interaction with brain cells, the administration techniques should include well known ones that allow for a crossing of the blood-brain barrier.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Manassas, Va.

Example 1

Isolation of GLM-R cDNAs

The extracellular domain (ECD) sequences (including the secretion signal sequence, if any) from about 950 known secreted proteins from the Swiss-Prot public database were used to search sequence databases. The databases included public databases (e.g., GenBank). In this instance, genomic DNA sequence from GenBank (i.e., AC008857) was analyzed using the gene prediction program GENSCAN, licensed from Stanford University. GENSCAN analysis predicts gene coding regions, creating sequences which can be subjected to the ECD search. The search was performed using the computer program BLAST or BLAST2 [Altschul et al., *Methods in Enzymology*, 266:460-480 (1996)] as a comparison of the ECD protein sequences to a 6 frame translation of the sequences. Those comparisons resulting in a BLAST score of 70 (or in some cases, 90) or greater that did not encode known proteins were clustered and assembled into consensus DNA sequences with the program "phrap" (Phil Green, University of Washington, Seattle, Wash.) if necessary.

From the consensus sequence, oligonucleotides were synthesized: 1) to identify by PCR a cDNA library that contained the sequence of interest, and 2) for use as probes to isolate a clone of the full-length coding sequence for PRO21073. Forward and reverse PCR primers generally range from 20 to 30 nucleotides and are often designed to give a PCR product of about 100-1000 bp in length. The probe sequences are typically 40-55 bp in length. In some cases, additional oligonucleotides are synthesized when the consensus sequence is greater than about 1-1.5 kbp. In order to screen several libraries for a full-length clone, DNA from the libraries was screened by PCR amplification, as per Ausubel et al., *Current Protocols in Molecular Biology*, supra, with the PCR primer pair. A positive library was then used to isolate clones encoding the gene of interest using the probe oligonucleotide and one of the primer pairs.

The PCR primers (forward and reverse) were:

forward PCR primer

5'-GTCAAGGAGTCAAAGTTCTGGAGTGACTGG-3' (SEQ ID NO:3)

reverse PCR primer

5'-CGCACATCGCAGAGCTATGACATATTC-3' (SEQ ID NO:4)

Additionally, a synthetic oligonucleotide hybridization probe was constructed from the consensus DNA172257 sequence which had the following nucleotide sequence:

hybridization probe

5'-CGTACAACCTCACGGGGCTGCAGCCTTTTACAG-3' (SEQ ID NO:5)

A pool of 50 different human cDNA libraries from various tissues was used in cloning. The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., *Science*, 253:1278-1280 (1991)) in the unique XhoI and NotI sites.

DNA sequencing of the clones isolated as described above gave the full-length DNA sequence for a full-length GLM-R nucleic acid (designated herein as DNA173920-2924, FIG. 1, SEQ ID NO:1) and the derived full length PRO21073 polypeptide.

The full length clone identified above contained a single open reading frame with an apparent translational initiation site at nucleotide positions 63-65 and a stop signal at nucleotide positions 2259-2261 (FIG. 1, SEQ ID NO:1). The predicted polypeptide precursor is 732 amino acids long, has a calculated molecular weight of approximately 82954 daltons and an estimated pI of approximately 7.15. Analysis of the full-length PRO21073 sequence shown in FIG. 2 (SEQ ID NO:2) evidences the presence of a variety of important polypeptide domains as shown in FIG. 2, wherein the locations given for those important polypeptide domains are approximate as described above. Clone DNA173920-2924 was deposited with ATCC on May 16, 2000 and is assigned ATCC Deposit No. 1874-PTA.

The GLM-R (PRO21073) sequence of FIG. 3A has features characteristic of type I cytokine receptors. A predicted signal peptide of 19 amino acid residues is followed by a cytokine receptor homology domain (residue 20-227) with two pairs of conserved cysteine residues and a WSDWS signature motif. Three modules with homology to fibronectin type III domains (residues 228-324, 325-420, 421-516) complete the extracellular domain, and a single transmembrane region (residues 517-539) connects to an intracellular domain of 193 amino acids (residues 540-732). Within the cytoplasmic tyrosine kinases of the Jak family, and four tyrosine residues that may serve as docking sites for downstream signaling molecules with SH2 domains are present.

Example 2

Use of GLM-R Polynucleotides as Hybridization Probes

The following method describes use of a nucleotide sequence encoding SRT as a hybridization probe.

DNA comprising the coding sequence of full-length or mature SRT is employed as a probe to screen for homologous DNAs (such as those encoding naturally-occurring variants of SRT) in human tissue cDNA libraries or human tissue genomic libraries.

Hybridization and washing of filters containing either library DNAs is performed under the following high stringency conditions. Hybridization of radiolabeled SRT-derived probe to the filters is performed in a solution of 50% formamide, 5×SSC, 0.1% SDS, 0.1% sodium pyrophosphate, 50 mM sodium phosphate, pH 6.8, 2× Denhardt's solution, and 10% dextran sulfate at 42° C. for 20 hours. Washing of the filters is performed in an aqueous solution of 0.1×SSC and 0.1% SDS at 42° C.

DNAs having a desired sequence identity with the DNA encoding full-length native sequence SRT can then be identified using standard techniques known in the art.

Example 3

Expression of GLM-R in *E. coli*

This example illustrates preparation of an unglycosylated form of GLM-R by recombinant expression in *E. coli*.

The DNA sequence encoding GLM-R is initially amplified using selected PCR primers. The primers should contain restriction enzyme sites which correspond to the restriction enzyme sites on the selected expression vector. A variety of expression vectors may be employed. An example of a suitable vector is pBR322 (derived from *E. coli*; see Bolivar et al., *Gene* 2:95 (1977)) which contains genes for ampicillin and tetracycline resistance. The vector is digested with restriction enzyme and dephosphorylated. The PCR amplified sequences are then ligated into the vector. The vector will preferably include sequences which encode for an antibiotic resistance gene, a trp promoter, a polyhis leader (including the first six STII codons, polyhis sequence, and enterokinase cleavage site), the GLM-R coding region, lambda transcriptional terminator, and an argU gene.

The ligation mixture is then used to transform a selected *E. coli* strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized GLM-R protein can then be purified using a metal chelating column under conditions that allow tight binding of the protein.

GLM-R may be expressed in *E. coli* in a poly-His tagged form, using the following procedure. The DNA encoding GLM-R is initially amplified using selected PCR primers. The primers will contain restriction enzyme sites which correspond to the restriction enzyme sites on the selected expression vector, and other useful sequences providing for efficient and reliable translation initiation, rapid purification on a metal chelation column, and proteolytic removal with enterokinase. The PCR-amplified, poly-His tagged sequences are then ligated into an expression vector, which is used to transform an *E. coli* host based on strain 52 (W3110 fuhA(tonA) lon galE rpoHts(htpRts) clpP(lacIq). Transformants are first grown in LB containing 50 mg/ml carbenicillin at 30° C. with shaking until an O.D.600 of 3-5 is reached. Cultures are then diluted 50-100 fold into CRAP media (prepared by mixing 3.57 g $(NH_4)_2SO_4$, 0.71 g sodium citrate.$2H_2O$, 1.07 g KCl, 5.36 g Difco yeast extract, 5.36 g Sheffield hycase SF in 500 mL water, as well as 110 mM MPOS, pH 7.3, 0.55% (w/v) glucose and 7 mM MgSO$_4$) and grown for approximately 20-30 hours at 30° C. with shaking. Samples are removed to verify expression by SDS-PAGE analysis, and the bulk culture is centrifuged to pellet the cells. Cell pellets are frozen until purification and refolding.

E. coli paste from 0.5 to 1 L fermentations (6-10 g pellets) is resuspended in 10 volumes (w/v) in 7 M guanidine, 20 mM Tris, pH 8 buffer. Solid sodium sulfite and sodium tetrathionate is added to make final concentrations of 0.1M and 0.02 M, respectively, and the solution is stirred overnight at 4° C. This step results in a denatured protein with all cysteine residues blocked by sulfitolization. The solution is centrifuged at 40,000 rpm in a Beckman Ultracentifuge for 30 min. The supernatant is diluted with 3-5 volumes of metal chelate column buffer (6 M guanidine, 20 mM Tris, pH 7.4) and filtered through 0.22 micron filters to clarify. The clarified extract is loaded onto a 5 ml Qiagen Ni-NTA metal chelate column equilibrated in the metal chelate column buffer. The column is washed with additional buffer containing 50 mM imidazole (Calbiochem, Utrol grade), pH 7.4. The protein is eluted with buffer containing 250 mM imidazole. Fractions containing the desired protein are pooled and stored at 4° C. Protein concentration is estimated by its absorbance at 280 nm using the calculated extinction coefficient based on its amino acid sequence.

The proteins are refolded by diluting the sample slowly into freshly prepared refolding buffer consisting of: 20 mM Tris, pH 8.6, 0.3 M NaCl, 2.5 M urea, 5 mM cysteine, 20 mM glycine and 1 mM EDTA. Refolding volumes are chosen so that the final protein concentration is between 50 to 100 micrograms/ml. The refolding solution is stirred gently at 4° C. for 12-36 hours. The refolding reaction is quenched by the addition of TFA to a final concentration of 0.4% (pH of approximately 3). Before further purification of the protein, the solution is filtered through a 0.22 micron filter and acetonitrile is added to 2-10% final concentration. The refolded protein is chromatographed on a Poros R1/H reversed phase column using a mobile buffer of 0.1% TFA with elution with a gradient of acetonitrile from 10 to 80%. Aliquots of fractions with A280 absorbance are analyzed on SDS polyacrylamide gels and fractions containing homogeneous refolded protein are pooled. Generally, the properly refolded species of most proteins are eluted at the lowest concentrations of acetonitrile since those species are the most compact with their hydrophobic interiors shielded from interaction with the reversed phase resin. Aggregated species are usually eluted at higher acetonitrile concentrations. In addition to resolving misfolded forms of proteins from the desired form, the reversed phase step also removes endotoxin from the samples.

Fractions containing the desired folded GLM-R polypeptide are pooled and the acetonitrile removed using a gentle stream of nitrogen directed at the solution. Proteins are formulated into 20 mM Hepes, pH 6.8 with 0.14 M sodium chloride and 4% mannitol by dialysis or by gel filtration using G25 Superfine (Pharmacia) resins equilibrated in the formulation buffer and sterile filtered.

Example 4

Expression of GLM-R in Mammalian Cells

This example illustrates preparation of a potentially glycosylated form of GLM-R by recombinant expression in mammalian cells.

The vector, pRK5 (see EP 307,247, published Mar. 15, 1989), is employed as the expression vector. Optionally, the GLM-R DNA is ligated into pRK5 with selected restriction enzymes to allow insertion of the GLM-R DNA using ligation methods such as described in Sambrook et al., supra. The resulting vector is called pRK5-GLM-R.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 μg pRK5-GLM-R DNA is mixed with about 1 μg DNA encoding the VA RNA gene [Thimmappaya et al., Cell 31:543 (1982)] and dissolved in 500 μl of 1 mM Tris-HCl, 0.1 mM EDTA, 0.227 M CaCl$_2$. To this mixture is added, dropwise, 500 μl of 50 mM HEPES (pH 7.35), 280 mM NaCl, 1.5 mM NaPO$_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 μCi/ml $^{35}$S-cysteine and 200 μCi/ml $^{35}$S-methionine. After a 12-hour incubation, the conditioned medium is collected, concentrated on a spin filter, and loaded onto a 15% SDS gel. The processed gel may be dried and exposed to film for a selected period of time to reveal the presence of GLM-R polypeptide. The cultures containing transfected cells may undergo further incubation (in serum free medium) and the medium is tested in selected bioassays.

In an alternative technique, GLM-R may be introduced into 293 cells transiently using the dextran sulfate method described by Somparyrac et al., Proc. Natl. Acad. Sci., 12:7575 (1981). 293 cells are grown to maximal density in a spinner flask and 700 μg pRK5-GLM-R DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 μg/ml bovine insulin and 0.1 μg/ml bovine transferrin. After about four days, the conditioned media is centrifuged and filtered to remove cells and debris. The sample containing expressed GLM-R can then be concentrated and purified by any selected method, such as dialysis and/or column chromatography.

In another embodiment, GLM-R can be expressed in CHO cells. The pRK5-GLM-R can be transfected into CHO cells using known reagents such as CaPO$_4$ or DEAE-dextran. As described above, the cell cultures can be incubated, and the medium replaced with culture medium (alone) or medium containing a radiolabel such as $^{35}$S-methionine. After determining the presence of GLM-R polypeptide, the culture medium may be replaced with serum free medium. Preferably, the cultures are incubated for about 6 days, and then the conditioned medium is harvested. The medium containing the expressed GLM-R can then be concentrated and purified by any selected method.

Epitope-tagged GLM-R may also be expressed in host CHO cells. The GLM-R may be subcloned out of the pRK5 vector. The subclone insert can undergo PCR to fuse in frame with a selected epitope tag such as a poly-his tag into a Baculovirus expression vector. The poly-his tagged GLM-R insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged GLM-R can then be concentrated and purified by any selected method, such as by $Ni^{2+}$-chelate affinity chromatography.

GLM-R may also be expressed in CHO and/or COS cells by a transient expression procedure or in CHO cells by another stable expression procedure.

Stable expression in CHO cells is performed using the following procedure. The proteins are expressed as an IgG construct (immunoadhesin), in which the coding sequences for the soluble forms (e.g. extracellular domains) of the respective proteins are fused to an IgG1 constant region sequence containing the hinge, CH2 and CH2 domains and/or is a poly-His tagged form.

Following PCR amplification, the respective DNAs are subcloned in a CHO expression vector using standard techniques as described in Ausubel et al., *Current Protocols of Molecular Biology*, Unit 3.16, John Wiley and Sons (1997). CHO expression vectors are constructed to have compatible restriction sites 5' and 3' of the DNA of interest to allow the convenient shuttling of cDNA's. The vector used expression in CHO cells is as described in Lucas et al., *Nucl. Acids Res.* 24:9 (1774-1779 (1996), and uses the SV40 early promoter/enhancer to drive expression of the cDNA of interest and dihydrofolate reductase (DHFR). DHFR expression permits selection for stable maintenance of the plasmid following transfection.

Twelve micrograms of the desired plasmid DNA is introduced into approximately 10 million CHO cells using commercially available transfection reagents Superfect® (Quiagen), Dosper® or Fugene® (Boehringer Mannheim). The cells are grown as described in Lucas et al., supra. Approximately $3 \times 10^{-7}$ cells are frozen in an ampule for further growth and production as described below.

The ampules containing the plasmid DNA are thawed by placement into water bath and mixed by vortexing. The contents are pipetted into a centrifuge tube containing 10 mLs of media and centrifuged at 1000 rpm for 5 minutes. The supernatant is aspirated and the cells are resuspended in 10 mL of selective media (0.2 µm filtered PS20 with 5% 0.2 µm diafiltered fetal bovine serum). The cells are then aliquoted into a 100 mL spinner containing 90 mL of selective media. After 1-2 days, the cells are transferred into a 250 mL spinner filled with 150 mL selective growth medium and incubated at 37° C. After another 2-3 days, 250 mL, 500 mL and 2000 mL spinners are seeded with $3 \times 10^5$ cells/mL. The cell media is exchanged with fresh media by centrifugation and resuspension in production medium. Although any suitable CHO media may be employed, a production medium described in U.S. Pat. No. 5,122,469, issued Jun. 16, 1992 may actually be used. A 3 L production spinner is seeded at $1.2 \times 10^6$ cells/mL. On day 0, the cell number pH is determined. On day 1, the spinner is sampled and sparging with filtered air is commenced. On day 2, the spinner is sampled, the temperature shifted to 33° C., and 30 mL of 500 g/L glucose and 0.6 mL of 10% antifoam (e.g., 35% polydimethylsiloxane emulsion, Dow Corning 365 Medical Grade Emulsion) taken. Throughout the production, the pH is adjusted as necessary to keep it at around 7.2. After 10 days, or until the viability dropped below 70%, the cell culture is harvested by centrifugation and filtering through a 0.22 µm filter. The filtrate was either stored at 4° C. or immediately loaded onto columns for purification.

For the poly-His tagged constructs, the proteins are purified using a Ni-NTA column (Qiagen). Before purification, imidazole is added to the conditioned media to a concentration of 5 mM. The conditioned media is pumped onto a 6 ml Ni-NTA column equilibrated in 20 mM Hepes, pH 7.4, buffer containing 0.3 M NaCl and 5 mM imidazole at a flow rate of 4-5 ml/min. at 4° C. After loading, the column is washed with additional equilibration buffer and the protein eluted with equilibration buffer containing 0.25 M imidazole. The highly purified protein is subsequently desalted into a storage buffer containing 10 mM Hepes, 0.14 M NaCl and 4% mannitol, pH 6.8, with a 25 ml G25 Superfine (Pharmacia) column and stored at −80° C.

Immunoadhesin (Fc-containing) constructs are purified from the conditioned media as follows. The conditioned medium is pumped onto a 5 ml Protein A column (Pharmacia) which had been equilibrated in 20 mM Na phosphate buffer, pH 6.8. After loading, the column is washed extensively with equilibration buffer before elution with 100 mM citric acid, pH 3.5. The eluted protein is immediately neutralized by collecting 1 ml fractions into tubes containing 275 µL of 1 M Tris buffer, pH 9. The highly purified protein is subsequently desalted into storage buffer as described above for the poly-His tagged proteins. The homogeneity is assessed by SDS polyacrylamide gels and by N-terminal amino acid sequencing by Edman degradation.

Example 5

Expression of GLM-R in Yeast

The following method describes recombinant expression of GLM-R in yeast.

First, yeast expression vectors are constructed for intracellular production or secretion of GLM-R from the ADH2/GAPDH promoter. DNA encoding GLM-R and the promoter is inserted into suitable restriction enzyme sites in the selected plasmid to direct intracellular expression of GLM-R. For secretion, DNA encoding GLM-R can be cloned into the selected plasmid, together with DNA encoding the ADH2/GAPDH promoter, a native GLM-R signal peptide or other mammalian signal peptide, or, for example, a yeast alpha-factor or invertase secretory signal/leader sequence, and linker sequences (if needed) for expression of GLM-R.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant GLM-R can subsequently be isolated and purified by removing the yeast cells from the fermentation medium by centrifugation and then concentrating the medium using selected cartridge filters. The concentrate containing GLM-R may further be purified using selected column chromatography resins.

Example 6

Expression of GLM-R in Baculovirus-Infected Insect Cells

The following method describes recombinant expression of GLM-R in Baculovirus-infected insect cells.

The sequence coding for GLM-R is fused upstream of an epitope tag contained within a baculovirus expression vector. Such epitope tags include poly-his tags and immunoglobulin tags (like Fc regions of IgG). A variety of plasmids may be employed, including plasmids derived from commercially available plasmids such as pVL1393 (Novagen). Briefly, the sequence encoding GLM-R or the desired portion of the coding sequence of GLM-R such as the sequence encoding the extracellular domain of a transmembrane protein or the sequence encoding the mature protein if the protein is extracellular is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BaculoGold™ virus DNA (Pharmingen) into *Spodoptera frugiperda* ("Sf9") cells (ATCC CRL 1711) using lipofectin (commercially available from GIBCO-BRL). After 4-5 days of incubation at 28° C., the released viruses are harvested and used for further amplifications. Viral infection and protein expression are performed as described by O'Reilley et al., *Baculovirus expression vectors: A Laboratory Manual*, Oxford: Oxford University Press (1994).

Expressed poly-his tagged GLM-R can then be purified, for example, by $Ni^{2+}$-chelate affinity chromatography as follows. Extracts are prepared from recombinant virus-infected Sf9 cells as described by Rupert et al., *Nature*, 362:175-179 (1993). Briefly, Sf9 cells are washed, resuspended in sonication buffer (25 mL Hepes, pH 7.9; 12.5 mM $MgCl_2$; 0.1 mM EDTA; 10% glycerol; 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% glycerol, pH 7.8) and filtered through a 0.45 μm filter. A $Ni^{2+}$-NTA agarose column (commercially available from Qiagen) is prepared with a bed volume of 5 mL, washed with 25 mL of water and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% glycerol, pH 6.0), which elutes nonspecifically bound protein. After reaching $A_{280}$ baseline again, the column is developed with a 0 to 500 mM Imidazole gradient in the secondary wash buffer. One mL fractions are collected and analyzed by SDS-PAGE and silver staining or Western blot with $Ni^{2+}$-NTA-conjugated to alkaline phosphatase (Qiagen). Fractions containing the eluted $His_{10}$-tagged GLM-R are pooled and dialyzed against loading buffer.

Alternatively, purification of the IgG tagged (or Fc tagged) GLM-R can be performed using known chromatography techniques, including for instance, Protein A or protein G column chromatography.

Example 7

Preparation of Antibodies that Bind GLM-R

This example illustrates preparation of monoclonal antibodies which can specifically bind GLM-R.

Techniques for producing the monoclonal antibodies are known in the art and are described, for instance, in Goding, supra. Immunogens that may be employed include purified GLM-R, fusion proteins containing GLM-R, and cells expressing recombinant GLM-R on the cell surface. Selection of the immunogen can be made by the skilled artisan without undue experimentation.

A construct encoding the extracellular domain of human GLM-R fused to an octahistidine tag was derived by recombinant PCR and cloned into a modified version of the pVL1393 baculovirus expression vector (BD Pharmingen, San Diego, Calif.). GLM-R-$His_8$ was expressed in High-five insect cells (Invitrogen, Carlsbad, Calif.) and purified by Nickel-nitrile-triacetic and affinity column. Monoclonal antibodies against GLM-R-$His_8$ were raised in balb/c mice in a manner similar to that described below.

Mice, such as Balb/c, are immunized with the GLM-R immunogen emulsified in complete Freund's adjuvant and injected subcutaneously or intraperitoneally in an amount from 1-100 micrograms. Alternatively, the immunogen is emulsified in MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect anti-GLM-R antibodies.

After a suitable antibody titer has been detected, the animals "positive" for antibodies can be injected with a final intravenous injection of GLM-R. Three to four days later, the mice are sacrificed and the spleen cells are harvested. The spleen cells are then fused (using 35% polyethylene glycol) to a selected murine myeloma cell line such as P3X63AgU.1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against GLM-R. Determination of "positive" hybridoma cells secreting the desired monoclonal antibodies against GLM-R is within the skill in the art.

The positive hybridoma cells can be injected intraperitoneally into syngeneic Balb/c mice to produce ascites containing the anti-GLM-R monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Example 8

Purification of GLM-R Polypeptides Using Specific Antibodies

Native or recombinant GLM-R polypeptides may be purified by a variety of standard techniques in the art of protein purification. For example, pro-GLM-R polypeptide, mature GLM-R polypeptide, or pre-GLM-R polypeptide is purified by immunoaffinity chromatography using antibodies specific for the GLM-R polypeptide of interest. In general, an immunoaffinity column is constructed by covalently coupling the anti-GLM-R polypeptide antibody to an activated chromatographic resin.

Polyclonal immunoglobulins are prepared from immune sera either by precipitation with ammonium sulfate or by purification on immobilized Protein A (Pharmacia LKB Biotechnology, Piscataway, N.J.). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated SEPHAROSE™ (Pharmacia LKB Biotechnology). The antibody is coupled to the resin, the resin is blocked, and the derivative resin is washed according to the manufacturer's instructions.

Such an immunoaffinity column is utilized in the purification of GLM-R polypeptide by preparing a fraction from cells containing GLM-R polypeptide in a soluble form. This preparation is derived by solubilization of the whole cell or of a subcellular fraction obtained via differential centrifugation by the addition of detergent or by other methods well known in the art. Alternatively, soluble GLM-R polypeptide containing a signal sequence may be secreted in useful quantity into the medium in which the cells are grown.

A soluble GLM-R polypeptide-containing preparation is passed over the immunoaffinity column, and the column is washed under conditions that allow the preferential absorbance of GLM-R polypeptide (e.g., high ionic strength buffers in the presence of detergent). Then, the column is eluted under conditions that disrupt antibody/GLM-R polypeptide binding (e.g., a low pH buffer such as approximately pH 2-3, or a high concentration of a chaotrope such as urea or thiocyanate ion), and GLM-R polypeptide is collected.

Example 9

Drug Screening

This invention is particularly useful for screening compounds by using GLM-R polypeptides or binding fragment thereof in any of a variety of drug screening techniques. The GLM-R polypeptide or fragment employed in such a test may either be free in solution, affixed to a solid support, borne on a cell surface, or located intracellularly. One method of drug screening utilizes eukaryotic or prokaryotic host cells which are stably transformed with recombinant nucleic acids expressing the GLM-R polypeptide or fragment. Drugs are screened against such transformed cells in competitive binding assays. Such cells, either in viable or fixed form, can be used for standard binding assays. One may measure, for example, the formation of complexes between GLM-R polypeptide or a fragment and the agent being tested. Alternatively, one can examine the diminution in complex formation between the GLM-R polypeptide and its target cell or target receptors caused by the agent being tested.

Thus, the present invention provides methods of screening for drugs or any other agents which can affect a GLM-R polypeptide-associated disease or disorder. These methods comprise contacting such an agent with an GLM-R polypeptide or fragment thereof and assaying (I) for the presence of a complex between the agent and the GLM-R polypeptide or fragment, or (ii) for the presence of a complex between the GLM-R polypeptide or fragment and the cell, by methods well known in the art. In such competitive binding assays, the GLM-R polypeptide or fragment is typically labeled. After suitable incubation, free GLM-R polypeptide or fragment is separated from that present in bound form, and the amount of free or uncomplexed label is a measure of the ability of the particular agent to bind to GLM-R polypeptide or to interfere with the GLM-R polypeptide/cell complex.

Another technique for drug screening provides high throughput screening for compounds having suitable binding affinity to a polypeptide and is described in detail in WO 84/03564, published on 13 Sep. 1984. Briefly stated, large numbers of different small peptide test compounds are synthesized on a solid substrate, such as plastic pins or some other surface. As applied to a GLM-R polypeptide, the peptide test compounds are reacted with GLM-R polypeptide and washed. Bound GLM-R polypeptide is detected by methods well known in the art. Purified GLM-R polypeptide can also be coated directly onto plates for use in the aforementioned drug screening techniques. In addition, non-neutralizing antibodies can be used to capture the peptide and immobilize it on the solid support.

This invention also contemplates the use of competitive drug screening assays in which neutralizing antibodies capable of binding GLM-R polypeptide specifically compete with a test compound for binding to GLM-R polypeptide or fragments thereof. In this manner, the antibodies can be used to detect the presence of any peptide which shares one or more antigenic determinants with GLM-R polypeptide.

Example 10

Rational Drug Design

The goal of rational drug design is to produce structural analogs of biologically active polypeptide of interest (i.e., an GLM-R polypeptide) or of small molecules with which they interact, e.g., agonists, antagonists, or inhibitors. Any of these examples can be used to fashion drugs which are more active or stable forms of the GLM-R polypeptide or which enhance or interfere with the function of the GLM-R polypeptide in vivo (c.f., Hodgson, *Bio/Technology*, 9: 19-21 (1991)).

In one approach, the three-dimensional structure of the GLM-R polypeptide, or of an GLM-R polypeptide-inhibitor complex, is determined by x-ray crystallography, by computer modeling or, most typically, by a combination of the two approaches. Both the shape and charges of the GLM-R polypeptide must be ascertained to elucidate the structure and to determine active site(s) of the molecule. Less often, useful information regarding the structure of the GLM-R polypeptide may be gained by modeling based on the structure of homologous proteins. In both cases, relevant structural information is used to design analogous GLM-R polypeptide-like molecules or to identify efficient inhibitors. Useful examples of rational drug design may include molecules which have improved activity or stability as shown by Braxton and Wells, *Biochemistry*, 31:7796-7801 (1992) or which act as inhibitors, agonists, or antagonists of native peptides as shown by Athauda et al., *J. Biochem.*, 113:742-746 (1993).

It is also possible to isolate a target-specific antibody, selected by functional assay, as described above, and then to solve its crystal structure. This approach, in principle, yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced peptides. The isolated peptides would then act as the pharmacore.

By virtue of the present invention, sufficient amounts of the GLM-R polypeptide may be made available to perform such analytical studies as X-ray crystallography. In addition, knowledge of the GLM-R polypeptide amino acid sequence provided herein will provide guidance to those employing computer modeling techniques in place of or in addition to x-ray crystallography.

Example 11

Isolation of GLM-R cDNAs and Cloning of hGH-R/GLM-R Chimeric Receptor

As reported in Example 1, cDNA encoding full length human GLM-R was subsequently cloned from a pooled tissue cDNA library. Murine GLM-R was obtained by a combination of cross-species library screening, and polymerase chain reaction (PCR) from a murine spleen library.

Murine GLM-R, a slightly shorter homolog with 716 amino acid residues, was cloned from a spleen library and shows 59.1% identity and 67.5% identity to the human molecule (FIG. 3B). All hallmark features except the second pair of cysteines and two cytoplasmic tyrosine residues are conserved between the two sequences. The lack of the cysteines in the murine protein does not appear to be due to alternative mRNA splicing, since analysis of murine genomic sequences did not reveal the presence of an alternative exon with those features (not shown).

As shown in FIG. 3C, human GLM-R is most homologous to the IL-6 signal transducer chain, gp130 [Hibi et al., Cell 63(6): 1149-57 (1990)], at 24.73% identity, followed by GCSF-R at 23.94% identity [Larsen et al., J. Exp. Med. 172(6): 1559-70 (1990)], and IL-12b2 at 20.09% identity [Presky, D. H. et al., Proc. Natl. Acad. Sci. USA 93(24): 14002-7 (1996)]. Interestingly, analysis of genomic sequences indicated that GLM-R and gp130 are separated by only 24 kilobases (kb) on human chromosome 5, and by 19 kb in a synthetic region on mouse chromosome 13. In light of the relatively low level of sequence conservation, this chromosomal localization pattern further confirms that mGLM-R and hGLM-R are true homologues.

Primers for the PCR were designated based on sequences obtained by data mining in the murine genomic database (Celera). Two clones stemming from independent PCR reactions were sequenced and confirmed to match with each other and the mRNA sequence predicted from genomic DNA using Genscan software. Burge, C. and Karlin, S. J., *Mol. Biol.* 268 (1): 78-94 (1997). A cDNA encoding a chimerica molecule, consisting of the extracellular domain of human GH-R and the intracellular domain of human GLM-R was obtained by recombinant PCR, [Ho, S. N. et al., *Gene* 77(1): 51-9 (1989)] using the partially complementary primers 5'-CTTTTCGAAACAGCAAAGGAAACCCAA-CAAATTGACTCA-3'(sense) (SEQ ID NO:6) and 5'-GGGTTTCCTTTGCTGTTTCGAAAAGAGAAAAAC-3' (antisense) (SEQ ID NO:7). This construct was cloned under the control of a CMV promoter into the expression vector pRK5tkneo.

To gain insight into the potential function of this receptor, we next sought to determine the expression pattern of GLM-R. The abundance of this transcript was generally so low that we were unable to reliably detect it by northern blot analysis in any organ (not shown). Supporting low expression levels is an absence of human expressed sequence tags (EST) corresponding to GLM-R in the public databases. We therefore analyzed GLM-R expression in a comprehensive panel of human total RNAs by real time quantitative PCR (Taqman™), using primers located in exon 11 (FIG. 4A). Highest levels of GLM-R transcript were detected in testis, prostate, thymus, bone marrow and trachea. GLM-R amplification product from testis RNA became detectable after 25 cycles of PCR (thymus, 26 cycles; prostate, 27 cycles), whereas rpl-19 amplification product was detectable after 18 cycles (thymus, 17 cycles; prostate, 18 cycles). Therefore, GLM-R expression in testis was roughly $2^7$=128 fold lower than rpl-19 expression (thymus, prostate, $2^9$=512 fold lower). Using a similar calculation, it can be determined that in most tissues, GLM-R is expressed at $10^3$ to $10^4$ fold lower levels than rpl-19.

Because type I cytokine receptors frequently play a role in blood cell development and function, and because GLM-R expression levels were comparably high in thymus and bone marrow, we were interested in the expression of GLM-R on blood cell subsets. To this end, peripheral blood mononuclear cells (PBMC) subsets were isolated from healthy human volunteers by Ficoll density gradient centrifugation followed by magnetic bead separation. Taqman™ PCR was then performed on RNA isolated from those cell fractions, using primers located in exon 11 of human GLM-R (FIG. 4B). Again, the absolute levels of GLM-R expression were very low, but CD14 positive and, to a lesser extent, CD56 positive cells displayed significantly higher expression than CD4, CD8, or CD19 positive cells. This expression pattern was confirmed by FACS analysis with monoclonal antibodies raised against the extracellular domain of GLM-R. GLM-R protein was only detectable at low to moderate levels on CD14 positive cells, and was barely detectable on CD56 positive cells. No GLM-R was expressed on CD4, CD8, or CD19 positive cells. Similar results were obtained from 4 independent blood donors, and a representative set of histograms is shown in FIG. 4. Compatible with the monocyte-specific expression of GLM-R, we found high levels of GLM-R transcripts in two monocytic human cell lines, THP-1 and U937 (FIG. 4D), whereas all other cell lines tested did not express GLM-R. Finally, we found that GLM-R was induced between 56 and 91 fold in freshly isolated human monocytes after 4 hours of stimulation with a combination of 1 µg/ml lipopolysaccharide (LPS) and 100 ng/ml interferon-γ (IFN-γ) (FIG. 4E). Again, GLM-R induction was confirmed at the protein level by FACS (not shown). Upregulation of GLM-R was not observed upon activation of T- or B-cells with appropriate stimuli, suggesting that this is a phenomenon restricted to monocytes (not shown).

Figure 5:
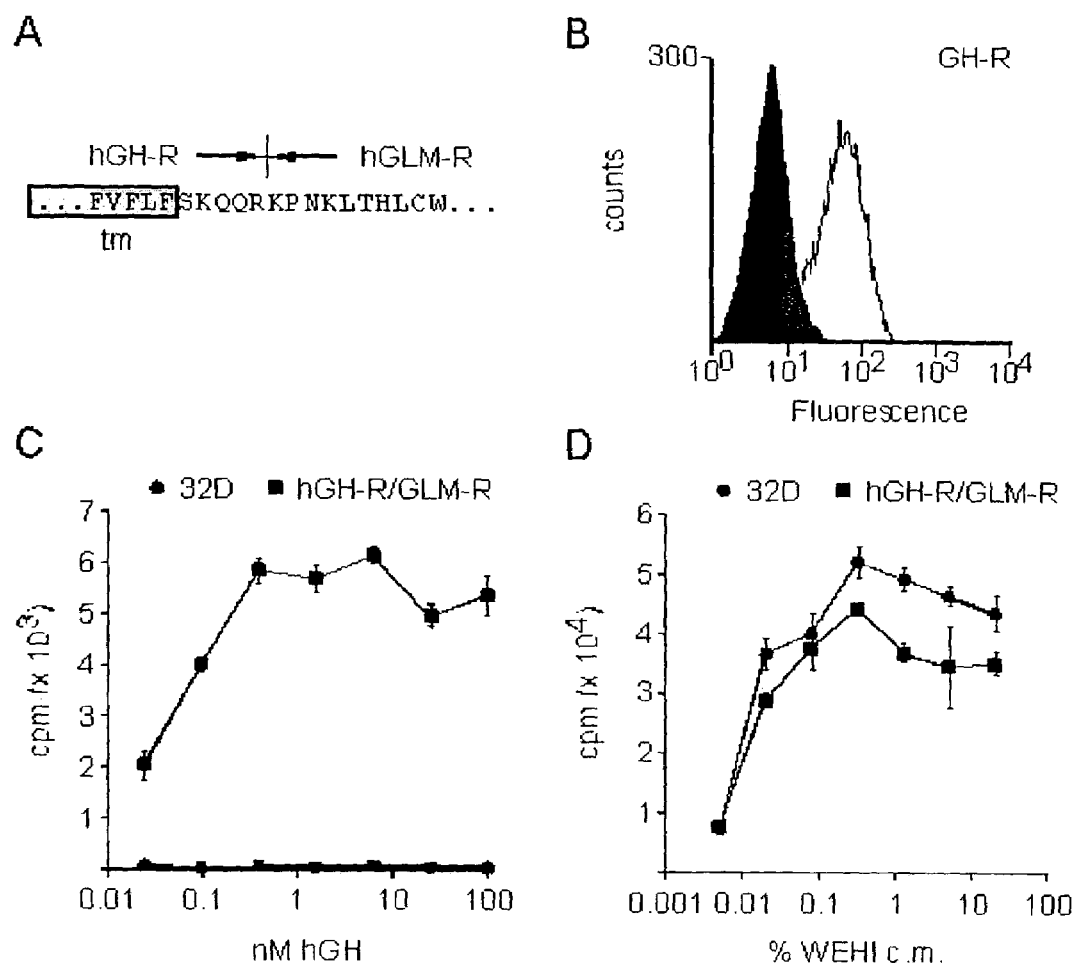
FIG. 5 depicts the results of introducing a chimeric hGH-R/GLM-R chimeric receptor into 32D cells and proliferation assay.

To address whether GLM-R is capable of transmitting a signal upon activation, we constructed a chimeric molecule consisting of the extracellular and transmembrane domains of human GH (hGH) receptor, joined to the cytoplasmic region of human GLM-R (FIG. 5A). This construct was stably transfected into IL-3 dependent murine 32D cells [Greenberger, J. S. et al., *Proc. Natl. Acad. Sci. USA* 80(10): 2931-5 (1983)], and three clones staining positive with an anti-hGH-R antibody were used for further analysis (FIG. 5B). All clones gave comparable results in subsequent assays.

First, we examined whether the hGH-R/GLM-R chimera could signal for proliferation when stimulated with hGH (FIG. 5C). We found that only hGH-R/GLM-R transfected cells were able to proliferate in a dose dependent manner in response to hGH, while both transfected and parental cells proliferated comparably in IL-3 (FIG. 5D).

Figure 6:
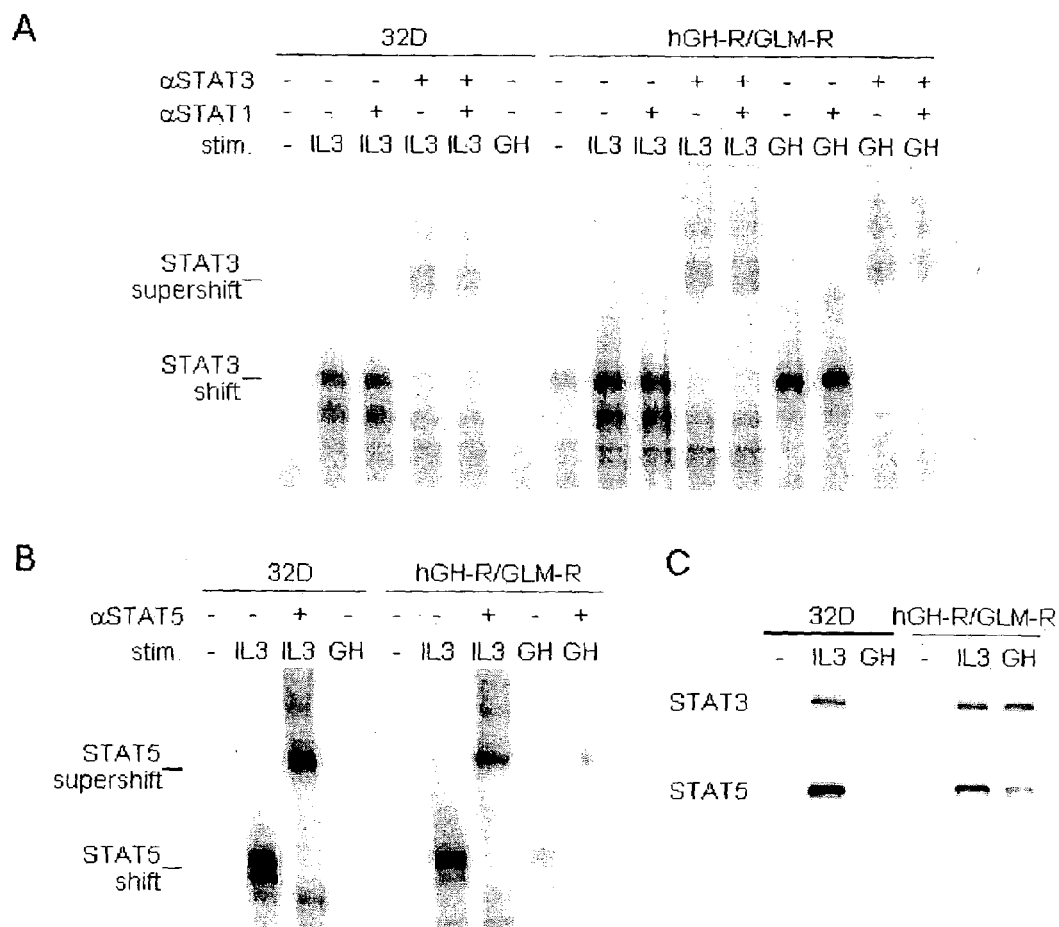
FIG. 6 shows STAT activation by an hGH-R/GLM-R chimera.

The Jak/STAT pathway is critical to transmit the signal generated by cytokine receptors, Ihle, J. N., *Nature* 377 (6550): 591-4 (1995), and STAT proteins were previously shown to transmit many of the specific effects of cytokines. Ihle, J. N., *Curr. Opin. Cell Biol.* 13 (2): 211-7 (2001). To analyze which of the STAT proteins are activated upon stimulation of the chimeric receptor with hGH, an electrophoretic mobility shift analysis (EMSA) was performed. A mutated form of the serum inducible element of the fos promoter (m67) [Wagnerm B. J. et al., *Embo. J.* 9(13): 4477-84 (1990)] was used to test for STAT-1, STAT-3, and STAT-4 activation, and the mammary gland factor response element of the β-casein gene (PCAS) [Schmitt-Ney et al., *Mol. Cell Biol.* 11(7): 3745-55 (1991)] was used to test for STAT-5 and STAT-6 activation. Upon hGH stimulation, hGH-R/GLM-R transfected cells displayed formation of a strong complex on the m67 probe, while parental cells did not respond. This complex was completely supershifted with an antibody against STAT-3 (FIG. 6A). A less intense yet clearly identifiable complex was present when extracts were incubated with the βCAS probe, and this complex was supershifted completely with an antibody against STAT-5 (FIG. 6B). STAT-3 and STAT-5 were also activated upon stimulation with IL-3 in both parental and transfected cells, as described previously [Mu, S. et al., *Blood* 86(12): 4532-4543; Pallard, C. et al., *J. Biol. Chem.* 270(27): 15942-5 (1995)] (23,24) (FIGS. 6A and 6B). To exclude the presence of interferon stimulated gene factor 3, a complex containing activated STAT-1 and STAT-2, extracts were also tested on the interferon stimulated response element (ISRE) (25) probe [Reich, N. et al., *Proc. Natl. Acad Sci. USA* 84(18): 6394-8 (1987)], but did nor observe any hGH specific gelshifts (not shown). Thus, no STAT molecules other than STAT-3 and STAT-5 are activated by hGH-R/GLM-R under these conditions. Specific activation of STAT-3 and STAT-5 upon activation of hGH-R/GLM-R was confirmed by phosphotyrosine-immunoprecipitation followed by western blot with antibodies specific for STAT-3 and STAT-5 (FIG. 6C).

Example 12

Quantitative PCR Analysis of GLM-R Expression

Total RNA from human organs was obtained from Clontech (Palo Alto, Calif.), and total RNA from cell lines or sorted cells was isolated using the Rneasy kit and DNAse I (Qiagen, Valencia, Calif.). Taqman™ quantitative RT-PCR using a sequence detector 7700 instrument was carried out according to the instructions of the manufacturer (Applied Biosystems, Foster City, Calif.). For each sample, duplicate test reactions and a control reaction into which no reverse transcriptase had been added were analyzed for expression of GLM-R mRNA and a housekeeper mRNA, rpl-19. If a signal was observed in the control reaction due to contamination with genomic DNA, it was subtracted from the signal in the test reaction. Arbitrary expression units were calculated by dividing GLM-R expression by rpl-19 expression. Probes and primers were designed using Primer Express software (Applied Biosystems, Foster City, Calif.). The primer triplets were 5'-CCTGGAGTCCCTGAAACGAA-3' (sense)(SEQ ID NO:8), 5'-GTTGGTTCCCCCAGCACTG-3' (antisense)(SEQ ID NO:9), 5'-CTCTTACATTGTTCAG-GTCATGGCCAGCA-3' (probe)(SEQ ID NO:10) for human GLM-R, and 5'-GATGCCGGAAAAACACCTTG-3' (sense)(SEQ ID NO:11), 5'-TGGCTGTACCCTTCCGCTT-3' (antisense)(SEQ ID NO:12), 5'-CCTATGCCCATGTGC-CTGCCCTT-3' (probe)(SEQ ID NO:13) for human rpl-19.

Example 13

Isolation of Blood Cell Subsets, FACS Analysis and Activation of Monocytes

Heparinized blood was obtained with informed consent from healthy volunteers. 35 ml of a 1:2 dilution of blood in phosphate buffered saline (PBS) were layered over 15 ml Ficoll-Hypaque (ICN Biomedicals, Costa Mesa, Calif.) and centrifuged for 30 minutes at 500×g. Interphase peripheral blood mononuclear cells (PBMC) were recovered and washed once with PBS. For RNA isolation, leukocyte subsets were separated using paramagnetic beads coupled to various marker antibodies according to the instructions of the manufacturer (Milteny, Auburn, Calif.). For FACS analysis, PBMC were incubated for 30 minutes on ice in a buffer containing 10 µg/ml total human IgG and 5 µg/ml murine IgG1 (Sigma, St. Louis, Mo.) to prevent Fc-receptor mediated binding of GLM-R antibodies. Cells were then stained with 1 µg per million cells of biotinylated anti-GLM-R (IgG1) or biotinylated isotype control antibody for 15 minutes, followed by two washes with the same buffer. In a second round of staining, cells were simultaneously incubated with streptavidin-coupled phycoerythrin (strep-PE) and various marker antibodies directly coupled to either fluorescin-isothiocyanate or Cychrome (BD Pharmingen, San Diego, Calif.). Fluorescence was detected using an Epics-XL flow cytometry system (Beckman Coulter Inc., Fullerton, Calif.). For stimulation experiments, isolation of monocytes from PBMC was performed by a depletion strategy employing paramagnetic beads coupled to antibodies against CD3, CD7, CD19, CD45RA, CD56, and IgE (Milteny, Auburn, Calif.). We chose this approach to avoid activation of monocytes by ligation of the CD14 antigen, which would occur in a positive selection approach. These monocytes were stimulated in RPMI supplemented with 10% bovine calf serum, penicillin-streptomycin, and L-glutamine (Invitrogen, Carlsbad, Calif.) at $2.5 \times 10^6$ cells/ml with 1 µg/ml LPS (Sigma, St. Louis, Mo.) and 100 ng/ml IFNγ (R&D Systems, Minneapolis, Minn.) for 4 hours.

Example 14

Culture and Transfection of 32D Cells 32D cells were maintained in RPMI supplemented with 10% bovine calf serum, L-Glutamine and Penicillin-Streptomycin (Invitrogen, Carlsbad, Calif.). Conditioned medium from WEHI-3B cells was used as a source of IL-3 and added to the culture at 5 to 10% final concentration. Cells were transfected by electroporation and bulk selected in 0.4 mg/ml G418 (Invitrogen, Carlsbad, Calif.) for 10 days. G418-resistant cells were then stained with a monoclonal antibody against hGH-R (Genentech, South San Francisco, Calif.), and single positive cells were sorted by FACS into individual wells of 96-well plates. After one week of expansion, clones were re-examined by FACS for hGH-R surface expression and by proliferation assay for factor dependence. Three clones with significant hGH-R expression and low background proliferation were selected for further experiments.

Example 15

Proliferation Assay

Cells were starved for 20 hours in complete medium without growth factors at a density of $5 \times 10^5$ cells/ml. Subsequently, $5 \times 10^4$ cells per well were seeded into 96 well plates containing different concentrations of hGH or WEHI-3B conditioned medium in triplicates. Cells were allowed to proliferate for 22 hours with addition of 1 µCi $^3$H-thymidine per well during the last six hour of the incubation period. Thymidine incorporation was determined using a Top Count liquid scintillation counter according to the manufacturers instructions (Packard Instruments, Meriden, Conn.).

Example 16

Analysis of STAT Activation $10^7$ cells per condition were washed free of IL-3 and starved for 6 hours in RPMI supplemented with 10% bovine calf serum. Purified recombinant hGH (Genentech Inc., South San Francisco, Calif.) or murine IL-3 (R&D Systems, Minneapolis, Minn.) were added to final concentrations of 100 ng/ml and 10 ng/ml, respectively. After 15 minutes at 37° C., cells were quick-chilled in icewater and washed once with ice-cold PBS. EMSA was performed as described in Levy et al., Genes Dev. 3(9): 1362-71 (1989), and gelshifts were detected with the oligonucleotide probes m67 5'-CATTTCCCGTAAATCAT-3' (SEQ ID NO:14) [Wagner, B. J. et al., Embo J. 9(13):4477-84 (1990)], and βCAS 5'-GATTTCTAGGAATTCAATCC-3' (SEQ ID NO:15) [Schmitt-Ney, M. et al., Mol. Cell Biol. 11(7): 3745-55 (1991)]. For supershift experiments, polyclonal anti-STAT-1 (sc-464X), anti-STAT-3 (sc-482X) and anti STAT-5 (sc-835X) (all Santa Cruz Biotechnology, Santa Cruz, Calif.) were used. For western blot analysis, cells were lysed in a buffer containing 50 mM Tris pH 7.5, 150 mM NaCl, 2 mM EDTA, 2 mM EGTA, 0.1% SDS, 1% Triton X-100, 2 mM NaVO$_4$, and complete™ protease inhibitors (Roche Molecular Biochemicals, Indianapolis, Ind.). After 20 minutes on ice, the lysates were centrifuged at 20000×g at 2° C., and the supernatants were used for immunoprecipitation. Precipitation of tyrosine phosphorylated proteins was carried out using a 1:1 mixture of 4G10-agarose (Upstate Biotechnology Inc., Lake Placid, N.Y.) and PY20-agarose (BD transduction labs, Lexington, Ky.). After washing 3× with lysis buffer, the immunoprecipitated proteins were separated by SDS-PAGE and transferred to nitrocellulose by western blot. STAT-3 was detected by sc-482, and STAT-5 was detected by sc-835 (Santa Cruz Biotechnology, Santa Cruz, Calif.) and enhanced chemiluminescence reagents (Amersham Pharmacia Biotech, Piscataway, N.J.).

Example 17

Tissue Expression Distribution

Oligonucleotide probes were constructed from the PRO21073 polypeptide-encoding nucleotide sequence shown in FIG. 1 for use in quantitative PCR amplification reactions. The oligonucleotide probes were chosen so as to give an approximately 200-600 base pair amplified fragment from the 3' end of its associated template in a standard PCR reaction. The oligonucleotide probes were employed in standard quantitative PCR amplification reactions with cDNA libraries isolated from different human adult and/or fetal tissue sources and analyzed by agarose gel electrophoresis so as to obtain a quantitative determination of the level of expression of the PRO21073 polypeptide-encoding nucleic acid in the various tissues tested. Knowledge of the expression pattern or the differential expression of the PRO21073 polypeptide-encoding nucleic acid in various different human tissue types provides a diagnostic marker useful for tissue typing, with or without other tissue-specific markers, for determining the primary tissue source of a metastatic tumor, disease diagnosis, and the like. These assays provided the following results.

| DNA Molecule | |
|---|---|
| | Tissues w/ Significant Expression |
| DNA173920-2924 | Highly expressed in testis, HUVEC, prostate and uterus. Expressed in cartilage, heart, bone marrow and spleen. |
| | Tissues w/o Significant Expression |
| DNA173290-2924 | Not expressed in colon tumor, placenta, adrenal gland and aortic endothelial cells. |

The following materials have been deposited with the American Type Culture Collection, 10801 University Blvd., Manassas, Va. 20110-2209, USA (ATCC):

| Material | ATCC Dep. No. | Deposit Date |
|---|---|---|
| DNA173920-2924 | 1874-PTA | May 16, 2000 |

This deposit was made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposit will be made available by ATCC under the terms of the Budapest Treaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 8860G 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

What is claimed is:

1. An isolated nucleic acid molecule which comprises (a) a nucleic acid encoding a GLM-R polypeptide that (i) is expressed in activated monocytes and preferentially phosphorylates STAT3 and (ii) has at least 95% sequence identity to the sequence of amino acid residues from 1 or 20 to 732 of FIG. 2 (SEQ ID NO:2), or (b) the complement of the nucleic acid molecule of (a).

2. The isolated nucleic acid molecule of claim 1 comprising the sequence of nucleotide positions from 63 or 120 to 2258 of FIG. 1 (SEQ ID NO:1).

3. The isolated nucleic acid molecule of claim 1 comprising the nucleotide sequence of FIG. 1 (SEQ ID NO:1).

4. The isolated nucleic acid molecule of claim 1 comprising a nucleotide sequence that encodes the sequence of amino acid residues from 1 or 20 to 732 of FIG. 2 (SEQ ID NO:2).

5. An isolated nucleic acid molecule which comprises (a) a nucleic acid encoding a GLM-R polypeptide that (i) is expressed in activated monocytes and preferentially phosphorylates STAT3 and (ii) has at least 95% sequence identity to (a) the polypeptide encoded by the human protein cDNA deposited with the ATCC on May 16, 2000 under ATCC Deposit No. 1874-PTA (DNA173920-2924), or (b) the complement of the nucleic acid molecule of (a).

6. The isolated nucleic acid molecule of claim 5 comprising a nucleic acid encoding the polypeptide encoded by the human protein cDNA deposited with the ATCC on May 16, 2000 under ATCC Deposit No. 1874-PTA (DNA173920-2924).

7. An isolated nucleic acid molecule which comprises (a) a nucleic acid encoding a GLM-R polypeptide that (i) is expressed in activated monocytes and preferentially phosphorylates STAT3 and (ii) has at least 95% sequence identity to the sequence of amino acid residues from X to 732 of FIG. 2 (SEQ ID NO:2) or (b) the complement of the nucleic acid molecule of (a), wherein X is any amino acid residue from 15 to 24 of FIG. 2 (SEQ ID NO:2).

8. A nucleic acid molecule deposited with the ATCC under accession number 1874-PTA (DNA173920-2924).

9. A vector comprising the nucleic acid molecule of any one of claims 1 to 6, or 7.

10. The vector of claim 9, wherein said nucleic acid molecule is operably linked to control sequences recognized by a host cell transformed with the vector.

11. An isolated host cell comprising the vector of claim 10.

12. The host cell of claim 11, wherein said cell is a CHO cell.

13. The host cell of claim 11, wherein said cell is an *E. coli*.

14. The host cell of claim 11, wherein said cell is a yeast cell.

15. A process for producing a GLM-R polypeptide comprising culturing the host cell of claim 11 under conditions suitable for expression of said GLM-R polypeptide and recovering said GLM-R polypeptide from the cell culture.

* * * * *